(12) United States Patent
Gallagher et al.

(10) Patent No.: US 8,604,075 B2
(45) Date of Patent: *Dec. 10, 2013

(54) METHODS AND COMPOSITIONS FOR IMPROVING COGNITIVE FUNCTION

(75) Inventors: Michela Gallagher, Baltimore, MD (US); Rebecca Haberman, Baltimore, MD (US); Ming Teng Koh, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 13/287,531

(22) Filed: Nov. 2, 2011

(65) Prior Publication Data

US 2012/0046336 A1    Feb. 23, 2012

Related U.S. Application Data

(63) Continuation of application No. 12/580,464, filed on Oct. 16, 2009.

(60) Provisional application No. 61/105,847, filed on Oct. 16, 2008, provisional application No. 61/152,631, filed on Feb. 13, 2009, provisional application No. 61/175,536, filed on May 5, 2009.

(51) Int. Cl.
*A61K 31/4015* (2006.01)

(52) U.S. Cl.
USPC ............................................. 514/424

(58) Field of Classification Search
USPC ............................ 514/423, 424; 548/550
See application file for complete search history.

(56) References Cited

U.S. PATENT DOCUMENTS

| | | | |
|---|---|---|---|
| 4,118,396 A | 10/1978 | Pifferi et al. | |
| 4,145,347 A | 3/1979 | L'Italien et al. | |
| 4,173,569 A | 11/1979 | Banfi et al. | |
| 4,221,789 A | 9/1980 | Rodriguez et al. | |
| 4,372,960 A | 2/1983 | L'Italien | |
| 4,476,308 A | 10/1984 | Aschwanden et al. | |
| 4,558,070 A | 12/1985 | Bauer et al. | |
| 4,595,695 A | 6/1986 | Ladkani et al. | |
| 4,650,878 A | 3/1987 | Aschwanden et al. | |
| 4,654,370 A | 3/1987 | Marriott, III et al. | |
| 4,668,687 A | 5/1987 | Yevich et al. | |
| 4,678,801 A | 7/1987 | Kurono et al. | |
| 4,696,943 A | 9/1987 | Gobert et al. | |
| 4,837,223 A | 6/1989 | Gobert et al. | |
| 4,837,224 A | 6/1989 | Gobert et al. | |
| 4,895,873 A | 1/1990 | Schäfer | |
| 4,913,906 A | 4/1990 | Friedman et al. | |
| 4,939,126 A | 7/1990 | Kurono et al. | |
| 4,943,639 A | 7/1990 | Gobert et al. | |
| 5,017,613 A | 5/1991 | Aubert et al. | |
| 5,019,398 A | 5/1991 | Daste | |
| 5,034,402 A | 7/1991 | Aschwanden et al. | |
| 5,049,586 A | 9/1991 | Ortega et al. | |
| 5,061,725 A | 10/1991 | Giannessi et al. | |
| 5,162,573 A | 11/1992 | Chiesi et al. | |
| 5,439,930 A | 8/1995 | Seredenin et al. | |
| 5,440,023 A | 8/1995 | Cheng et al. | |
| 5,447,952 A | 9/1995 | Wulfert et al. | |
| 5,856,569 A | 1/1999 | Santaniello et al. | |
| 5,886,023 A | 3/1999 | Otomo et al. | |
| 6,131,106 A | 10/2000 | Steele, Jr. | |
| 6,610,326 B2 | 8/2003 | Chen et al. | |
| 6,620,802 B1 * | 9/2003 | Schatzberg et al. | ........... 514/178 |
| 7,090,985 B2 | 8/2006 | Lynch et al. | |
| 7,244,747 B2 | 7/2007 | Kenda et al. | |
| 7,544,705 B2 | 6/2009 | Farina et al. | |
| 7,557,137 B2 | 7/2009 | Decicco et al. | |
| 7,678,808 B2 | 3/2010 | Barlow et al. | |
| 7,858,611 B2 | 12/2010 | Barlow et al. | |
| 2004/0063776 A1 | 4/2004 | Ueda et al. | |
| 2004/0116505 A1 | 6/2004 | Krauss et al. | |
| 2004/0116506 A1 | 6/2004 | Krusz | |
| 2004/0204388 A1 | 10/2004 | Lynch et al. | |
| 2006/0063707 A1 | 3/2006 | Baudry et al. | |
| 2007/0135514 A1 | 6/2007 | Lynch et al. | |
| 2007/0244143 A1 | 10/2007 | Barlow et al. | |
| 2007/0298098 A1 | 12/2007 | Jenkins et al. | |
| 2008/0014264 A1 | 1/2008 | Goffin et al. | |

(Continued)

FOREIGN PATENT DOCUMENTS

AU    08/904016    8/2008
AU    08/904021    8/2008

(Continued)

OTHER PUBLICATIONS

Levetiracetam American journal of health-system pharamcy vol. 57 Aug. 15, 2000 p. 1484.*
French et al., "Levetiracetam overall safety profile," Epilepsia, 42(S7):151 (2001).
Gaudenzi et al., "[Levetiracetam therapy in patients with epilepsy and dementia]," Bollettino—Lega Italiana contro l'Epilessia, 125-126:215-216 (2004) (English Abstract only).
Glien et al., "Effects of the novel antiepileptic drug levetiracetam on spontaneous recurrent seizures in the rat pilocarpine model of temporal lobe epilepsy," Epilepsia, 43(4):350-357 (2002).
Klatte et al., "The quality of life with levetiracetam in benign rolandic epilepsy," Epilepsia, 49 (S7):220, P2.108 (2008) (Abstract).
Kopp et al., "Cognitive side affects of levetiracetam in monotherapy: comparison with carbamazepine and valproate," Epilepsia, 48(S3):39-40 (2007) (Abstract).

(Continued)

*Primary Examiner* — Jennifer M Kim
(74) *Attorney, Agent, or Firm* — Ropes & Gray LLP; James F. Haley, Jr.; Qianru Li

(57) ABSTRACT

This invention relates to treating age-related cognitive impairment. This invention in particular relates to the use of inhibitors of synaptic vesicle protein 2A (SV2A), such as levetiracetam, seletracetam, and brivaracetam, in improving cognitive function in subjects that exhibit age-related cognitive impairment or are at risk thereof, including, without limitation, subjects having or at risk for Mild Cognitive Impairment (MCI), Age-related Cognitive Decline (ARCD) or Age-Associated Memory Impairment (AAMI).

18 Claims, 3 Drawing Sheets

(56) References Cited

U.S. PATENT DOCUMENTS

| | | |
|---|---|---|
| 2008/0045583 A1 | 2/2008 | Delmarre et al. |
| 2008/0076820 A1 | 3/2008 | Otomo et al. |
| 2008/0081832 A1 | 4/2008 | Kenda et al. |
| 2008/0242698 A1 | 10/2008 | Flor et al. |
| 2009/0074854 A1 | 3/2009 | Caron et al. |
| 2009/0131508 A1 | 5/2009 | Verdru |
| 2009/0176740 A1 | 7/2009 | Phillips, II |
| 2010/0087422 A1 | 4/2010 | Bird |
| 2010/0099735 A1 | 4/2010 | Gallagher et al. |
| 2010/0125096 A1 | 5/2010 | Farina et al. |
| 2010/0216734 A1 | 8/2010 | Barlow et al. |

FOREIGN PATENT DOCUMENTS

| | | |
|---|---|---|
| EP | 162036 | 11/1985 |
| EP | 0165919 | 12/1985 |
| EP | 0381959 | 8/1990 |
| EP | 1731149 | 12/2006 |
| GB | 1039113 | 8/1966 |
| GB | 1309692 | 3/1973 |
| WO | WO 01/39779 | 6/2001 |
| WO | WO 01/62726 | 8/2001 |
| WO | WO 02/094787 | 11/2002 |
| WO | WO 03/032981 | 4/2003 |
| WO | WO 2004/087658 | 10/2004 |
| WO | WO 2005/108358 | 11/2005 |
| WO | WO 2005/121082 | 12/2005 |
| WO | WO 2006/128692 | 12/2006 |
| WO | WO 2006/128693 | 12/2006 |
| WO | WO 2007/065595 | 6/2007 |
| WO | WO 2007/104035 | 9/2007 |
| WO | WO 2008/095221 | 8/2008 |
| WO | WO 2008/132139 | 11/2008 |
| WO | WO 2009/038412 | 3/2009 |
| WO | WO 2009/109547 | 9/2009 |
| WO | WO 2010/006929 | 1/2010 |
| WO | WO 2010/015029 | 2/2010 |
| WO | WO 2010/057870 | 5/2010 |
| WO | WO 2010/086315 | 8/2010 |
| WO | WO 2010/089372 | 8/2010 |
| WO | WO 2011/015349 | 2/2011 |

OTHER PUBLICATIONS

Meo et al., "Use of levetiracetam monotherapy in patients with post-traumatic epilepsy: Preliminary data," Epilepsia, 47(S4):162, P2135 (2006) (Abstract).

Shorvon et al., "Multicenter double-blind, randomized, placebo-controlled trial of levetiracetam as add-on therapy in patients with refractory partial seizures. European Levetiracetam Study Group," Epilepsia, 41(9):1179-1186 (2000).

UCB Keppra® Injectable Formulation Label Approved on Sep. 12, 2007.

UCB Keppra® Label Approved on Apr. 23, 2009.

UCB Keppra® XR Label Approved on Apr. 23, 2009.

Agam et al., "Levetiracetam does not interfere with attention to novel and targeted stimuli: An psychophysiological study," Neurology, 68(12), S1, P06.051 (2007) (Abstract).

Brandt et al., "Prophylactic treatment with levetiracetam after status epilepticus: lack of effect on epileptogenesis, neuronal damage, and behavioral alterations in rats," Neuropharmacology, 53(2):207-221 (2007).

Brown et al., "Impact of levetiracetam on mood and cognition during prednisone therapy," European Psychiatry, 22(7):448-452 (2007).

Cicolin et al., "[Levetiracetam and cognitive functions: A single blind, crossover, placebo controlled study in healthy volunteers]," Bolletinno Lega Italiana contro l'Epilessia, No. 113-114:79-81 (2001) (English Abstract only).

Cumbo et al., "Levetiracetam, lamotrigine, and phenobarbital in patients with epileptic seizures and Alzheimer's disease," Epilepsy & Behavior, 17(4):461-466 (2010).

Cumbo, "Effects of levetiracetam, phenobarbital and lamotrigine on neuropsychological performance and mood in patients with alzheimer's disease and epilepsy," Epilepsia, 50(S4):101-102 (2009).

Detrait et al., "Brivaracetam does not alter spatial learning and memory in both normal and amygdala-kindled rats," Epilepsy Research, 91(1):74-83 (2010).

Detrait et al., "Brivaracetam does not impair cognitive performance of rats in the morris water maze test," Epilepsia, 49(S7):111, P1.253 (2008) (Abstract).

Detrait et al., "Brivaracetam does not impair cognitive performance in normal and kindled rats," Epilepsia, 50(S10):96, P450 (2009) (Abstract).

Dinapoli et al., "Quality of life and seizure control in patients with brain tumor-related epilepsy treated with levetiracetam monotherapy: preliminary data of an open-label study," Neurological Sciences, 30(4):353-359 (2009).

Edelbroek et al., "Evaluation of the pharmacokinetic and neuropsychometric parameters in chronic comedicated epileptic patients of three increasing dosages of a novel, antiepileptic drug, UCB L059 250-mg capsules per Os each dose for one week followed by two-weeks of placebo," Epilepsia, 34(S2):7 (1993) (Abstract).

Fritz et al., "Effects of add-on treatment with topiramate or levetiracetam on cognition and health related quality of life in patients with epilepsy," European Journal of Neurology, 12 (S2):121 P1341 (2005) (Abstract).

Fritz et al., "Effects of add-on treatment with topiramate or levetiracetam on cognition and health related quality of life for patients with epilepsy," Epilepsia, 46(S6):106-107 (2005) (Abstract).

Gevins et al., "Neuropsychological and neurophysiological effects of carbamazepine and levetiracetam," Epilepsia, 47(S4):157-158,P2112 (2006) (Abstract).

Gomer et al., "The influence of antiepileptic drugs on cognition: a comparison of levetiracetam with topiramate," Epilepsy & Behavior, 10(3):486-494 (2007).

Guido et al., "Event-related potential sin the evaluation of the effect of levetiracetam and carbamazepine on cognitive functions in newly diagnosed epilepsy patients; preliminary results of a randomized trial," Epilepsia, 48(S7):107, P244 (2007) (Abstract).

Guido et al., "Event-related potentials (ERPs) in the evaluation of the effect of levetiracetam and carbamazepine on cognitive functions in adult patients with newly diagnosed epilepsy," European Journal of Neurology, 15(S3):305 (2008) (Abstract).

Haber et al., "Cognitive effects of levetiracetam in patients treated for interactable epilepsy," Epilepsia, 47( S4):97-98, P1.197 (2006) (Abstract).

Huang et al., "Comparative cognitive effects of levetiracetam and topiramate in intractable epilepsy," Psychiatry and Clinical Neurosciences, 62(5):548-553 (2008).

Kong et al., "Effect of antiepileptic drugs on cognitive functions and expressions of glutamate receptor 2 and synaptophysin of the hippocampus in rats," Journal of Shandong University (Health Science), 48(7):14-18 (2010) (Chinese language, English Abstract).

Lamberty et al., "Absence of negative impact of levetiracetam on cognitive function and memory in normal and amygdala-kindled rats," Epilepsy & Behavior, 1:333-342 (2000).

Lamberty et al., "Cognitive performance is unaltered by levetiracetam (ucb L059) in the pilocarpine model of chronic epilepsy," Epilepsia, 39(S2):85 (1998) (Abstract).

Lamberty et al., "Lack of negative impact on cognitive function differentiates levetiracetam (UCB L059) from other antiepileptic drugs," Epilepsia, 39(S6):45, P2.053 (1998) (Abstract).

Leeman et al., "Cognitive effects of treatment of focal interictal discharges with levetiracetam," Epilepsia, 49(S7):136-137, P1.312 (2008) (Abstract).

Levisohn et al., "Neurocognitive effects of adjunctive levetiracetam in children with partial-onset seizures: a randomized, double-blind, placebo-controlled, noninferiority trial," Epilepsia 50(11):2377-2389 (2009).

Meador et al., "Cognitive and behavioral effects of carbamazepine and levetiracetam in healthy volunteers: S09.002: 2:15 pm," Neurology, 66(S2) p A72 (2006) (Abstract).

Meador et al., "Neurocognitive effects of brivaracetam, levetiracetam, and lorazepam," Epilepsia, 52(2):264-272 (2011).

Meador et al., "Neuropsychological and neurophysiologic effects of carbamazepine and levetiracetam," Neurology, 69(22):2076-2084 (2007).

(56) References Cited

OTHER PUBLICATIONS

Mechtler et al., "Efficacy of intravenous levetiracem in the treatment of status migrainosus," Headache, 48( S1):S45-S46, S16 (2008) (Abstract).
Minervini et al., "Mild cognitive impairment, focal epilepsy and levetiracetam," Epilepsia, 49(S7):110, P256 (2007) (Abstract).
Mintz et al., "Double-blind, placebo-controlled, non-inferiority study to evaluate the cognitive and neuropsychological effects of levetiracetam 20-60 mg/kg/day as adjunctive treatment versus placebo in pediatric patients with partial-onset seizures," Epilepsia, 48(S6):356, P3.292 (2007) (Abstract).
Neyens et al., "Cognitive effects of a new pyrrolidine derivative (levetiracetam) in patients with epilepsy," Prog. Neuro-Psychopharmacol. & Biol. Psychiat., 19(3):411-419 (1995).
Neyens et al., "Cognitive side effects of levetiracetam (UCB LO59) in epilepsy," Epilepsia, 35(S7):76 (1994) (Abstract).
Nghiemphu et al., "Levetiracetam monotherapy in patients with malignant glioma," Neuro-Oncology, p. 566, QL-11 (2007).
Rugino et al., "Levetiracetam in autistic children: an open-label study," Journal of Development and Behavioral Pediatrics, 23(4)225-230 (2002).
Sargentini-Maier et al., "The pharmacokinetics, CNS pharmacodynamics and adverse event profile of brivaracetam after single increasing oral doses in healthy males," British Journal of Clinical Pharmacology, 63(6):680-688 (2007).
Schoenberg et al., "Results of a randomized double-blind placebo controlled cross-over study of the cognitive and mood effects of levetiracetam in healthy older adults," Epilepsia, 48(S6):339, P3.246 (2007) (Abstract).
Shannon et al., "Effects of antiepileptic drugs on attention as assessed by a five-choice serial reaction time task in rats," Epilepsy Behavior, 7:620-628 (2005).
Shannon et al., "Effects of antiepileptic drugs on learning as assessed by a repeated acquisition of response sequences task in rats," Epilepsy Behavior, 10(1):16-25 (2007).
Shannon et al., "Effects of antiepileptic drugs on working memory as assessed by spatial alternation performance in rats," Epilepsy Behavior, 5(6):857-865 (2004).
Specchio et al., "Event-related potentials (erps) in the evaluation of the effect of levetiracetam and carbamazepine on cognitive functions in adult newly diagnosed epileptic patients. preliminary results of a randomized open trial," Epilepsia, 50(S4):98, T189 (2009) (Abstract).
Walker et al., "Early experience with UCB L059 in refractory epilepsy," European Congress Proceedings, 35(S7):76 (1994) (Abstract).
Wojda et al., "Isobolographic characterization of interactions of levetiracetam with the various antiepileptic drugs in the mouse 6Hz psychomotor seizure model," Epilepsy Research, 86(2-3):163-174 (2009).
Zhao et al., "Effect of levetiracetam on visual-spatial memory impairment following status epilepticus," Epilepsia, 47(S4):201 (2006) (Abstract).
Zhou et al., "Effect of levetiracetam on visual-spatial memory following status epilepticus," Epilepsy Research, 73(1):65-74 (2006).
Zou et al., "Effects of chronic treatment of levetiracetam on cognitive and motor recovery after experimental traumatic brain injury," Journal of Neurotrauma, 26:A67, P262 (2009) (Abstract).
Aeby et al., "Levetiracetam efficacy in epileptic syndromes with continuous spikes and waves during slow sleep: experience in 12 cases," Epilepsia, 46(12):1937-1942 (2005).
Altenmüller et al., "Termination of absence status epilepticus by low-dose intravenous levetiracetam—a case report," Epilepsia, 48(S6):336, P3.238 (2007) (Abstract).
Arcas et al., "Levetiracetamin children and adolescents with refractory epilepsy: A clinical experience," Epilepsia, 47(S3):179 Absp696 (2006) (Abstract).
Bootsma et al., "The effect of antiepileptic drugs on cognition: patient perceived cognitive problem of topiramate versus levetiracetam in clinical practice," Epilepsia, 47(S2):24-27 (2006).

Cercy et al., "Gelastic epilepsy and dysprosodia in a case of late-onset right frontal seizures," Epilepsy & Behavior, 16(2):360-365 (2009).
Chaisewikul et al., "Levetiracetam add-on for drug-resistant localization related (partial) epilepsy (review)," Cochrane Database of Systematic Reviews Issue 1 (2010).
Ciesielski et al., "Neuropsychological and psychiatric impact of add-on titration of pregabalin versus levetiracetam: A comparative study," Epilepsia, 47(S3):Absp518 (2006).
Ciesielski et al., "Neuropsychological and psychiatric impact of add-on titration of pregabalin versus levetiracetam: a comparative short-term study," Epilepsy & Behavior, 9(3):424-431 (2006).
Cramer et al., "Effect of levetiracetam on epilepsy-related quality of life. N132 Study Group," Epilepsia, 41(7):868-874 (2000).
Diaz Negrillo et al., "[Levetiracetam efficacy in patients with Lennox-Gastaut syndrome. Presentation of a case]," Neurologia, 26(5):285-290 (2011) (Spanish language article, English Abstract Only).
Dyzdarer et al., "Levetiracetam in the treatment of refractory epilepsy in children," Epilepsia, 50(S 4)244:AbsE720 (2009) (Abstract).
Ehtisham et al., "Cognitive outcomes following seizure prophylaxis for intracranial hemorrhages of different subtypes with levetiracetam versus phenytoin," Annals of Neurology, 64(S12):S30, M-110 (2008).
Fauser et al., "Effect of levetiracetam in limbic encephalitis: A case report," Epilepsia, 44(S 8):111-112 P298 (2003) (Abstract).
Feleppa et al., "Epileptogenic Kluver-Bucy syndrome (EKBS) treated with nasogastric levetiracetam (LVT) as adjunctive therapy: A case of excellent neurological recovery at 4 months after discharge," European Journal of Neurology, 14(S1):214 Absp2206 (2007) (Abstract).
French et al., "A systematic review of the safety profile of levetiracetam: a new antiepileptic drug," Epilepsy Research, 47(1-2):77-90 (2001).
Frings et al., "Early detection of behavioral side effects of antiepileptic treatment using handheld computers," Epilepsy & Behavior, 13(2):402-406 (2008).
Frings et al., "Effects of add-on treatment with levetiracetam on cognition in epilepsy patients," Epilepsia, 44, S 8, p. 111, P297 (2003) (Abstract).
Garcia-Penas et al., "Efficacy and safety of levetiracetam monotherapy for children with epilepsy," Epilepsia, 48(S7):150 Absp390 (2007) (Abstract).
Guo et al., "Effects of levetiracetam on quality of life in children with refractory epilepsy," Changjiang Daxue Xuebao, Ziran Kexueban, 8(1):151-155 (2011) (English Abstract only).
Helmstaedter et al., "Cognitive outcome of antiepileptic treatment with levetiracetam versus carbamazepine monotherapy: a non-interventional surveillance trial," Epilepsy & Behavior, 18(1-2):74-80 (2010).
Helmstaedter et al., "Positive and negative psychotropic effects of levetiracetam," Epilepsy & Behavior, 13(3):535-541 (2008).
Helmstaedter et al., "The effects of levetiracetam on cognition: a non-interventional surveillance study," Epilepsy & Behavior, 13(4):642-649 (2008).
Helmstaedter, "'Real life' cohort study on levetiracetam versus carbamazepine monotherapy: a controlled surveillance study," Epilepsia, 50(S10):100, P465 (2009) (Abstract).
Helmstaedter, "'Real life' cohort study on levetiracetam versus carbamazepine monotherapy—a controlled surveillance study on cognition," Epilepsia, 50(S6):47, P210 (2009) (Abstract).
Herranz et al., "Effectiveness and tolerability of levetiracetam in 43 children and adolescents with epilepsy," Revisa de neurologia, 37(11):1005-1008 (2003) (English Abstract only).
Herranz et al., "Levetiracetam: efficacy and tolerability in children and adolescents with epilepsy," Epilepsia, 44(S 8):152, P457 (2003) (Abstract).
Herranz et al., "Effectiveness and safety of levetiracetam in 133 children with medication resistant epileptic seizures," Revista de neurologia, 43(7):393-397 (2006) (English Abstract only).
Higgins et al., "Comparative study of five antiepileptic drugs on a translational cognitive measure in the rat: relationship to antiepileptic property," Psychopharmacology, 207(4):513-527 (2010).

(56) References Cited

OTHER PUBLICATIONS

Himi et al., "Levetiracetam prevents the attention deficit induced by bilateral carotid artery occlusion in mice," Journal of Pharmacological Sciences, 109(S1):226P (2009) (English Abstract only).

Ioannidis et al., "Transient epileptic amnesia in a memory clinic setting: A report of three cases," Epilepsy and Behavior, 20(2):414-417 (2011).

Junemann et al., "Cognitive performance in patients with focal and primary generalized epilepsy under levetiracetam or topiramate monotherapy: a prospective pseudo-randomized study," Epilepsia,50(S6):47, P209 (2009) (Abstract).

Koh et al., "Treatment strategies targeting excess hippocampal activity benefit aged rats with cognitive impairment," Neuropsychopharmacology, 35(4):1016-1025 (2010).

Kossoff et al., "A pilot study transitioning children onto levetiracetam monotherapy to improve language dysfunction associated with benign rolandic epilepsy," Epilepsy & Behavior, 11(4):514-517 (2007).

Lagae et al., "Clinical experience with levetiracetam in childhood epilepsy: an add-on and mono-therapy trial," Seizure, 14:66-71 (2005).

Lagae et al., "Effect of levetiracetam on behavior and alertness in children with refractory epilepsy," Epilepsia, 44(S9):92, P1.258 (2003) (Abstract).

Lindholm, "Levetiracetam levels correlating with successful treatment of epilepsy, headaches, cognitive effects, and adverse reactions in pediatric age group," Epilepsia, 43(S7):60 (2002) (Abstract).

Lippa et al., "Levetiracetam: a practical option for seizure management in elderly patients with cognitive impairment," American Journal of Alzheimer's Disease & Other Dementias, 25(2):149-154 (2010).

Lippa et al., "Levetiracetam: seizure management for elderly patients with cognitive impairment," Neurology, 70(11, S1) Absp02-185 (2008) (Abstract).

Lopez-Gongora et al., "Cognitive function and quality of life after six months treatment with levetiracetam (LEV)," Epilepsia, 46(S 6):156, P136 (2005) (Abstract).

López-Góngora et al., "Effect of levetiracetam on cognitive functions and quality of life: a one-year follow-up study," Epileptic Disord, 10(4):297-305 (2008).

Mecarelli et al., "Clinical cognitive, and neurophysiologic correlates of short-term treatment with carbamazepine, oxcarbazepine, and levetiracetam in healthy volunteers," Annual Pharmacotherapy, 38(11):1816-1822 (2004).

Minervini et al., "Mild cognitive impairment, focal epilepsy and levetiracetam," Epilepsia, 48:(S7):110, P256 (2007) (Abstract).

Mintz et al., "The underrecognized epilepsy spectrum: the effects of levetiracetam on neuropsychological functioning in relation to subclinical spike production," Journal of Child Neurology, 24(7):807-815 (2009).

Mintz et al., "The effects of levetiracetam on neuropsychological functioning in relation to "subclinical" spike production," Epilepsia, 47, S4, p. 112, 1.237 (2006) (Abstract).

Muscas et al., "[Efficacy and tolerability of Levetiracetam in epileptic patients with acquired progressive cognitive impairment]," Bollettino—Lega Italiana contro l'Epilessia, 129-130:233-234 (2005).

Palmer et al., "Correlation between behavioural adverse events and cognitive functions in epilepsy patients receiving levetiracetam," Epilepsia, 44(S8):172, P537 (2003) (Abstract).

Park et al., "Increased EEG current-source density in the high Beta frequency band induced by levetiracetam adjunctive therapy in refractory partial epilepsy," Journal of Clinical Neurology (Seoul, Korea) 5(4):178-185 (2009).

Piazzini et al., "Levetiracetam: an improvement of attention and of oral fluency in patients with partial epilepsy," Epilepsy Research, 68(3):181-188 (2005).

Quiske et al., "Add-on treatement with LEV and its influence on cognition," Epilepsia, 46(S6):311, P986 (2005).

Ravagnan et al., "ESES: 4 cases treated with levetiracetam," Bollettino—Lega Italiana contro l'Epilessia, 138:77-78 (2008) (English Abstract only).

Rudakova et al., "Levetiracetam (keppra) in the treatment of different epileptic syndromes in adults," Zhurnal nevrologii i psikhiatrii imeni S.S. Korsakova / Ministerstvo zdravookhraneniia i meditsinskoi promyshlennosti Rossiiskoi Federatsii, Vserossiiskoe obshchestvo nevrologov [i] Vserossiiskoe obshchestvo psikhiatrov, 109(10):25-29 (2009) (English Abstract only).

Ryzhkov et al., "Levetiracetam treatment in rare epileptic syndromes of early childhood: a case series," Epilepsia, 47(S3):180,P701 (2006) (Abstract).

Ryzhkov, "Advantages of levetiracetam as monotherapy in treating epileptic syndromes of early childhood, characterized by psychological disorders," European Journal of Neurology, 14(S1):90, P1224 (2007) (Abstract).

Salas-Puig et al., "Self-reported memory problems in everyday activities in patients with epilepsy treated with antiepileptic drugs," Epilepsy & Behavior, 14(4):622-627 (2009).

Tozzi et al., "[Levetiracetam in children and adolescents: Generalised vs partial seizures]," Bollettino—Lega Italiana contro l'Epilessia, 133-134:257-258 (2006) (English Abstract only).

Verloes et al., "Effects of nootropic drugs in a scopolamine-induced amnesia model in mice," Psychopharmacology, 95(2):226-230 (1988).

Vicenzini et al., "[Clinical and neuropsycological effects of carbamazepine, oxcarbazepine and levetiracetam in healthy volunteers]"—Bollettino—Lega Italiana contro l'Epilessia, 118:173-175 (2002) (Italian-English abstract only).

Von Stülpnagel et al., "Levetiracetam as add-on therapy in different subgroups of "benign" idiopathic focal epilepsies in childhood," Epilepsy & Behavior, 17(2):193-198 (2010).

Wheless et al., "Levetiracetam in refractory pediatric epilepsy," Journal of Child Neurology, 17(6):413-415 (2002).

Witt et al., "The impact of antiepileptic drug treatment on attention and executive functions," Epilepsia, 51(S4):20 (2010) (Abstract).

Witt, "The effects of levetiracetam on cognition—a noninterventional surveillance study," Epilepsia, 50(S4):227 (2009) (Abstract).

Wu et al., "Clinical efficacy and cognitive and neuropsycholoical effects of levetiracetam in epilepsy: an open-label multicenter study," Epilepsy & Behavior, 16(3):468-474 (2009) (Abstract).

Yang et al., "Adjunctive levetiracetam in children and adolescents aged 4-16 years with partial-onset seizures: A long-term, multicenter, noncomparative, open-label, follow-up study," Epilepsia, 50(S10):102, p471 (2009) (Abstract).

Yang et al., "Therapeutic effect of levetiracetam for epilepsy combined with electrical status epilepticus during sleep in children," Shiyong Erke Linchuang Zazhi, 25(12):937-939 (2010) (English Abstract only).

Zhou et al., "Cognitive and quality of life effects of levetiracetam as an add-on therapy for partial seizures," Epilepsia, 48(S7):70, P116 (2007) (Abstract).

Zhou et al., "Levetiracetam: an improvement of attention and of oral fluency in patients with partial epilepsy," Epilepsy & Behavior, 12:305-310 (2008).

Banfi et al., "Cyclic GABA-GABOB analogs. IV. Activity on learning and memory," Farmaco, Edizione Scientifica, 39(1):16-22 (1984).

Bartolini et al., "Aniracetam restores object recognition impaired by age, scopolamine, and nucleus basalis lesions," Pharmacol. Biochem. Behav., 53(2):277-283 (1996).

Bartolini et al., "Effect of scopolamine and nootropic drugs on rewarded alternation in a T-maze," Pharmacol. Biochem. Behav., 43(4):1161-1164 (1992).

Bhattacharya et al., "Latency of memory consolidation induced in mice by piracetam, a nootropic agent," Indian J. Exp. Biol., 31(11):898-901 (1993).

Bottini et al., "Oxiracetam in dementia: a double-blind, placebo-controlled study," Acta. Neurol. Scand., 86(3):237-241 (1992).

(56) References Cited

OTHER PUBLICATIONS

Butler et al., "Amnesia-reversal activity of a series of N-[(disubstituted-amino)alkyl]-2-oxo-1-pyrrolidineacetamides, including pramiracetam," Journal of Medicinal Chemistry, 27:684-691 (1984).
Cavoy et al., "Relationships between arousal and cognition-enhancing effects of oxiracetam," Pharmacol. Biochem. Behav., 47(2):283-287 (1994).
Claus et al., "Nootropic drugs in Alzheimer's disease: symptomatic treatment with pramiracetam," Neurology, 41(4):570-574 (1991).
Croisile et al., "Long-term and high-dose piracetam treatment of Alzheimer's disease," Neurology, 43(2):301-305 (1993).
De Vreese et al., "Memory training and drug therapy act differently on memory and metamemory functioning: evidence from a pilot study," Arch. Gerontol. Geriatr., 22(S 1):9-22 (1996).
Ennaceur et al., "A new one-trial test for neurobiological studies of memory in rats. II: Effects of piracetam and pramiracetam," Behav. Brain Research, 33(2):197-207 (1989).
Fedi et al., "Long-term efficacy and safety of piracetam in the treatment of progressive myoclonus epilepsy," Arch. Neurol., 58(5):781-786 (2001).
Firstova et al., "Effects of nootropic drugs on hippocampal and cortical BDNF levels in mice with different exploratory behavior efficacy," Eksperimental'naya i Klinicheskaya Farmakologiya, 72(6):3-6 (2009) (English Abstract only).
Gallai et al., "A clinical and neurophysiological trial on nootropic drugs in patients with mental decline," Acta. Neurol. (Napoli), 13(1):1-12 (1991).
Gamzu, "Animal behavioral models in the discovery of compounds to treat memory dysfunction," Annals of the New York Academy of Sciences, 444:370-393 (1985).
Ghelardini et al., "The novel nootropic compound DM232 (unifiram) ameliorates memory impairment in mice and rats," Drug Development Research, 56:23-32 (2002).
Green et al., "Treatment trial of oxiracetam in Alzheimer's disease," Arch. Neurol., 49(11):1135-1136 (1992).
Gualtieri et al., "Design and study of piracetam-like nootropics, controversial members of the problematic class of cognition-enhancing drugs," Current Pharmaceutical Design, 8(2):125-138 (2002).
Hlinak et al., "Kynurenic acid and 5,7-dichlorokynurenic acids improve social and object recognition in male rats," Psychopharmacology (Berl), 120(4):463-469 (1995).
Hlinak et al., "Oxiracetam prevented the scopolamine but not the diazepam induced memory deficits in mice," Behav. Brain Research, 133(2):395-399 (2002).
Israel et al., "Drug therapy and memory training programs: A double-blind randomized trial of general practice patients with age-associated memory impairment," International Psychogeriatrics, 6(2):155-170 (1994).
Lebrun et al., "Effects of S 18986-1, a novel cognitive enhancer, on memory performances in an object recognition task in rats," European Journal of Pharmacology, 401(2):205-212 (2000).
Magnani et al., "Oxiracetam antagonizes the disruptive effects of scopolamine on memory in the radial maze," Psychopharmacology (Berl), 106(2):175-178 (1992).
Maina et al., "Oxiracetam in the treatment of primary degenerative and multi-infarct dementia: a double-blind, placebo-controlled study," Neuropsychobiology, 21(3):141-145 (1989).
Maresova et al., "Pramiracetam and epileptic after-discharges in young rats after hypoxia," Act. Nerv. Super (Praha), 31(1):68-69 (1989).
Marini et al., "Placebo-controlled double-blind study of pramiracetam (CI-879) in the treatment of elderly subjects with memory impairment," Advances in Therapy 9(3):136-146 (1992).
Mauri et al., "Pramiracetam effects on scopolamine-induced amnesia in healthy volunteers," Arch. Gerontol. Geriatr., 18(2):133-139 (1994).
Mondadori et al., "Elevated corticosteroid levels block the memory-improving effects of nootropics and cholinomimetics," Psychopharmacology (Berl), 108(1-2):11-15 (1992).
Mondadori et al., "The GABAB receptor antagonist CGP 36,742 and the nootropic oxiracetam facilitate the formation of long-term memory," Behav. Brain Research, 77(1-2):223-225 (1996).
Mondadori et al., "The pharmacology of the nootropics; new insights and new questions," Behavioural Brain Research, 59(1-2):1-9 (1993).
Mondadori et al., "Delayed emergence of effects of memory-enhancing drugs: implications for the dynamics of long-term memory," Proceedings of the National Academy of Science USA, 91(6):2041-2045 (1994).
Murphy et al., "Chronic exposure of rats to cognition enhancing drugs produces a neuroplastic response identical to that obtained by complex environment rearing," Neuropsychopharmacology, 31(1):90-100 (2006).
Murray et al., "The effect of pramiracetam (CI-879) on the acquisition of a radial arm maze task," Psychopharmacology (Berl), 89(3):378-381 (1986).
Nakamoto et al., "Nootropic nefiracetam inhibits proconvulsant action of peripheral-type benzodiazepines in epileptic mutant EL mice," Annals New York Academy of Science, 1025:135-139 (2004).
Nikolova et al., "Effects of ACE-inhibitors on learning and memory processes in rats," Folia Med. (Plovdiv), 42(1):47-51 (2000).
Parnetti et al., "Neuropsychological results of long-term therapy with oxiracetam in patients with dementia of Alzheimer type and multi-infarct dementia in comparison with a control group," Neuropsychobiology, 22(2):97-100 (1989).
Perini et al., "Use of valproate in treatment of behavioural and psychological disturbances of dementia," European Neuropsychopharmacology, 15:S565, P.5.017 (Abstract).
Petkov et al., "Effect of CDP-choline on learning and memory processes in rodents," Methods Find Exp. Clin. Pharamcol., 14(8):593-605 (1992).
Pitsikas et al., "Effect of oxiracetam on scopolamine-induced amnesia in the rat in a spatial learning task," 43(3):949-951 (1992).
Platel et al., "Habituation of exploratory activity in mice: effects of combinations of piracetam and choline on memory processes," Pharmacol. Biochem. Behav., 21(2):209-212 (1984).
Poschel et al., "Pharmacologic therapeutic window of pramiracetam demonstrated in behavior, EEG, and single neuron firing rates," Experientia, 41(9):1153-1156 (1985).
Poschel et al., "Pharmacology of the cognition activator pramiracetam (CI-879)," Drugs under Experimental and Clinical Research, 9(12):853-872 (1983).
Preda et al., "Effects of acute doses of oxiracetam in the scopolamine model of human amnesia," Psychopharmacology (Berl), 110(4):421-426 (1993).
Pugsley et al., "Some neurochemical properties of pramiracetam (CI-879) a new cognition enhancing agent," Drug Development Research, 3(5):407-420 (1983).
Rao et al., "Effects of intrahippocampal aniracetam treatment on Y-maze avoidance learning performance and behavioral long-term potentiation in dentate gyrus in rat," Neuroscience Letters, 298(3):183-186 (2001).
Rozzini et al., "Treatment of cognitive impairment secondary to degenerative dementia. Effectiveness of oxiracetam therapy," Acta. Neurol. (Napoli), 15(1):44-52 (1993).
Saletu et al., "Pharmaco-EEG and Brain Mapping in Cognitive Enhancing Drugs," Clin. Neuropharamacol., 13(S 2):575-576 (1990).
Salimov et al., "Effect of chronic piracetam on age-related changes of cross-maze exploration in mice," Pharmacol. Biochem. Behav., 52(3):637-640 (1995).
Sansone et al., "Effects of oxiracetam, physostigmine, and their combination on active and passive avoidance learning in mice," Pharmacol. Biochem. Behav., 44(2):451-455 (1993).
Sara et al., "Piracetam facilitates retrieval but does not impair extinction of bar-pressing in rats," Psychopharmacology (Berl.), 61(1):71-75 (1979).
Sara, "Memory retrieval deficits: alleviation by etiracetam, a nootropic drug," Psychopharmacology, 68(3):235-241 (1980).
Villardita et al., "Clinical studies with oxiracetam in patients with dementia of Alzheimer type and multi-infarct dementia of mild to moderate degree," Neuropsychobiology, 25(1):24-28 (1992).

(56) References Cited

OTHER PUBLICATIONS

Waegemans et al., "Clinical efficacy of piracetam in cognitive impairment: a meta-analysis," Dement. Geriatr. Cogn. Disord., 13(4):217-224 (2002).
Wolthuis et al., "Behavioural effects of etiracetam in rats," Pharmacology Biochemistry & Behavior, 15:247-255 (1981).
Wolthuis, "Experiments with UCB 6215, a drug which enhances acquisition in rats: its effects compared with those of metamphetamine," Eur. J. Pharmacol., 16(3):283-297 (1971).
Yamada et al., "Prolongation of latencies for passive avoidance responses in rats treated with aniracetam or piracetam," Pharmacol. Biochem. Behav., 22(4):645-648 (1985).
Aarts et al., "Selective cognitive impairment during focal and generalized epileptiform EEG activity," Brain, 107(Pt. 1):293-308 (1984).
Boido et al., "Cortico-hippocampal hyperexcitability in synapsin I/II/III knockout mice: age-dependency and response to the antiepileptic drug levetiracetam," Neuroscience, 171(1):268-283 (2010).
Bridgman et al., "Memory during subclinical hippocampal seizures," Neurology, 39(6):853-856 (1989).
Campos-Castello, "Neuropsychology and epilepsy," Revista de Neurologia, 39(2):166-177 (2004) (English Abstract only).
Coras et al., "Low proliferation and differentiation capacities of adult hippocampal stem cells correlate with memory dysfunction in humans," Brain, 133(11):3359-3372 (2010).
Heidegger et al., "Effects of antiepileptic drugs on associative LTP-like plasticity in human motor cortex," European Journal of Neuroscience, 32:1215-1222 (2010).
Himi et al., "Levetiracetam prevents attentional deficits induced by bilateral common artery occlusion in mice," Epilepsia, 48(S6):323, 3.203 (2007) (Abstract).
Krakow et al., "Effects of antiepileptic drugs on cortical plasticity and motor learning: A double blind, placebo-controlled transcranial magnetic stimulation study," Epilepsia, 46(8):212-213 (2005).
Lamberty et al., "Behavioural phenotyping reveals anxiety-like features of SV2A deficient mice," Behavioural Brain Research, 198(2):329-333 (2009).
Lukyanetz et al., "Selective blockade of N-type calcium channels by levetiracetam," Epilepsia, 43(1):9-18 (2002).
Manthey et al., "Sulthiame but not levetiracetam exerts neurotoxic effect in the developing rat brain," Experimental Neurology, 193(2):497-503 (2005).
Martella et al., "Seletracetam (ucb 44212) inhibits high-voltage-activated Ca2+ currents and intracellular Ca2+ increase in rat cortical neurons in vitro," Epilepsia, 50(4):702-710 (2009).
Nagarkatti et al., "Levetiracetam inhibits both ryanodine and IP3 receptor activated calcium induced calcium release in hippocampal neurons in culture," 436(3):289-293 (2008).
Niespodziany et al., "Levetiracetam inhibits the high-voltage-activated Ca2+ current in pyramidal neurons of rat hippocampal slices," Neuroscience Letters, 306:5-8 (2001).
Paulson et al., "Effect of levetiracetam on hippocampal protein expression and cell proliferation in rats," Epilepsy Research, 90(1-2):110-120 (2010).
Provinciali et al., "Recognition impairment correlated with short bisynchronous epileptic discharges," 32(5):684-689 (1991).
Sohn et al., "Effect of levetiracetam on rapid motor learning in humans," Annals of Neurology, 50:S31-S32 (2001).
Sohn et al., "Effect of levetiracetam on rapid motor learning in humans," Archives of Neurology, 59:1909-1912 (2002).
Sugaya et al., "Levetiracetam suppresses development of spontaneous EEG seizures and aberrant neurogenesis following kainate-induced status epilepticus," Brain Research, 1352:187-199 (2010).
Veauthier et al., "Impact of levetiracetam add-on therapy on different EEG occipital frequencies in epileptic patients," Seizure: the journal of the British Epilepsy Association,18(6):392-395 (2009).
Abou-Khalil, "Benefit-risk assessment of levetiracetam in the treatment of partial seizures," Drug Safety, 28(10):871-890 (2005).
Abou-Khalil, "Levetiracetam in the treatment of epilepsy," Neuropsychiatric Disease and Treatment, 4(3):507-523 (2008).
Adam et al., "Symptomatic Treatment of Huntington Disease," The Journal of the American Society for Experimental NeuroTherapeutics 5(2):181-197 (2008).
Aldenkamp et al., "Newer antiepileptic drugs and cognitive issues," Epilepsia, 44(S4):21-29 (2003).
Asconapé, "Some common issues in the use of antiepileptic drugs," Seminars in Neurology, 22(1):27-39 (2002).
Béatrice Brunner et al., Neurocognitive effects of antiepileptic drugs frequently used in long term treatement of epilepsies: A review, Epileptologie, 25:118-130 (2008).
Bourgeois, "Determining the effects of antiepileptic drugs on cognitive function in pediatric patients with epilepsy," Journal of Child Neurology, 19(S1):S15-S24 (2004).
Carreno et al., "Cognitive disorders associated with epilepsy: Diagnosis and treatment," The Neurologist, 14(6S):S26-S34 (2008).
Chaisewikul et al., "Levetiracetam add-on for drug-resistant localization related (partial) epilepsy," Cochrane Collaboration, Issue 1, p. 1-25 (2010).
Cramer et al., "A systematic review of the behavioral effects of levetiracetam in adults with epilepsy, cognitive disorders, or an anxiety disorder during clinical trials," Epilepsy & behavior, 4(2):124-132 (2003).
Czubak et al., "Cognitive effects of GABAergic antiepileptic drugs," Arzneimittel-Forschung, 60:(1)1-11 (2010).
Frostl et al., "The families of cognition enhancers," Pharmacopsychiatry, 22(2):54-100 (1989).
Gamzu et al., "Drug improvement of cognition: Hope and reality," Psychiatrie et Psychobiologie, 3(No. SPEC. ISS B):115-123 (1988).
Gamzu et al., "Recent developments in 2-pyrrolidinone-containing nootropics," Drug Development Research, 18(3):177-189 (1989).
Genton et al., "Piracetam and levetiracetam: close structural similarities but different pharmacological and clinical profiles," Epileptic disorders, 2( 2):99-105 (2000) (Abstract).
Goldberg et al., "Cognitive side effects of anticonvulsants," Journal of Clinical Psychiatry, 62(S14):27-33 (2001).
Gouliaev et al., "Piracetam and other structurally related nootropics," Brain Research Review, 19(2):180-222 (1994).
Hamed, "The aspects and mechanisms of cognitive alterations in epilepsy: the role of antiepileptic medications," CNS Neuroscience & Therapeutics, 15(2):134-156 (2009).
Hermann et al., "Cognition across the lifespan: antiepileptic drugs, epilepsy, or both?" Epilepsy Behavior, 17:1-5 (2010).
Jelic et al., "Clinical trials in mild cognitive impairment: lessons for the future," J. Neurol. Neurosurg. Psychiatry., 77(4):429-438 (2006).
Jetter et al., "Epilepsy in the elderly," Seminars in Neurology, 28(3):336-341 (2008).
Kaindl et al., "Antiepileptic drugs and the developing brain," Cellular and Molecular Life Sciences, 63(4): 399-413 (2006).
Kalinin, "Suicidality and antiepileptic drugs. Is there a link?" Drug Safety, 30(2):123-142 (2007).
Kamada Kyousuke, "Are clinical features derived from evidences and experiences outside of Japan applicable to clinical practices in Japan? Comparisons of results among studies conducted in US, Europe, Asian Countries and Japan," Brain and nerve=Shinkei kenkyu no shinpo, 63(3):247-54 (2011) (English Abstract only).
Klitgaard et al., "Use of epileptic animals for adverse effect testing," Epilepsy Research, 50(1-2):55-65 (2002).
Lagae, "Cognitive side effects of anti-epileptic drugs. The relevance in childhood epilepsy," Seizure, 5(4):235-241 (2006).
Loring et al., "Neuropsychological and behavioral effects of antiepilepsy drugs," Neuropsychol Rev, 17(4):413-425 (2007).
Lyseng-Williamson, "Levetiracetam: a review of its use in epilepsy," Drugs, 71(4):489-514 (2011).
Maguire et al., "Epilepsy (generalised)," Neurological disorders, Clinical evidence, 6(1201):1-14 (2009).
Maguire et al., "Epilepsy (partial)," Neurological disorders,Clinical evidence, 5(1214):1-42 (2011).
Malik et al., "Towards better brain management: Nootropics," Current Medicinal Chemistry, 14:123-131 (2007).
Malykh et al., "Piracetam and piracetam-like drugs: from basic science to novel clinical applications to CNS disorders," Drugs, 70(3):287-312 (2010).

(56) References Cited

OTHER PUBLICATIONS

Meador, "Cognitive and memory effects of the new antiepileptic drugs," Epilepsy Research, 68(1):63-67 (2006).
Meador, "Cognitive effects of levetiracetam versus topiramate," Epilepsy Currents, 8(3):64-65 (2008).
Merlini et al., "Trends in searching for new cognition enhancing drugs," Progress in Neuro-Psychopharmacology and Biological Psychiatry, 13: S61-S75 (1989).
Mondadori et al., "The Effects of Nootropics on Memory: New Aspects for Basic Research," Pharmacopsychiatry, 22(S 2):102-106 (1989).
Mula et al., "Antiepileptic Drug-Induced Cognitive Adverse Effects Potential Mechanisms and Contributing Factors," CNS Drugs, 23(2):121-137 (2009).
Nicholson, "Pharmacology of nootropics and metabolically active compounds in relation to their use in dementia," Psychopharmacology, 101(No. 2):147-159 (1990).
Onuma Teiichi, "Cognitive Dysfunction and Antiepileptic Drugs," Brain and Nerve (Tokyo), 63( 4):379-383 (2011) (Abstract—Japanese and English translation ).
Sankar et al., "Mechanisms of action for the commonly used antiepileptic drugs: relevance to antiepileptic drug-associated neurobehavioral adverse effects," Journal of Child Neurology, 19 (S1):S6-S14 (2004).
Sarter et al., "Behavioral screening for cognition enhancers: From indiscriminate to valid testing: Part I," Psychopharmacology, 107:144-159 (1992).
Schmidt et al., "Strategies and new aspects in the pharmacology of drugs for the treatment of senile dementia," Drug Development Research, 14(3-4):251-262 (1988).
Schmitz et al., "Assessing the unmet treatment need in partial-onset epilepsy: looking beyond seizure control," Epilepsia, 51(11):2231-2240 (2010).
Shorvon, "Pyrrolidone derivatives," Lancet, 358(9296):1885-1892 (2001).
Stepien et al., "Profile of anticonvulsant activity and neuroprotective effects of novel and potential antiepileptic drugs—an update," Pharmacological Reports, 57(6):719-733 (2005).
Vecht et al., "Seizures in low- and high-grade gliomas: current management and future outlook," Expert Review Anticancer Therapy, 10(5):663-669 (2010).
Wang et al., "Effect of commonly used new antiepileptic drugs on cognition," Zhongguo Xinyao Yu Linchuang Zazhi, China 27(9):705-709 (2008) (English Abstract only).
Wheless, "Levetiracetam in the treatment of childhood epilepsy," Neuropsychiatric Disease and Treatment, 3(4):409-421 (2007).
Wilby et al., "Clinical effectiveness, tolerability and cost-effectiveness of newer drugs for epilepsy in adults: a systematic review and economic evaluation," Health Technology Assessment, Executive Summary—Newer drugs for epilepsy in adult, 9(15) (2005).
Winnicka et al., "Piracetam—An old drug with novel properties," Acta Pol.Pharm., Drug Research, 62(5):405-409 (2005).
Wu, "The effects of antiepileptic drugs on cognitive function," Erke Yaoxue Zazhi, China, 13(6):7-9 (2007) (English Abstract only).
Zaccara et al., "Central nervous system adverse effects of new antiepileptic drugs. A meta-analysis of placebo-controlled studies," Seizure, 17(5):405-421 (2008).
Bajjalieh et al., "SV2, a brain synaptic vesicle protein homologous to bacterial transporters," Science, 257(5074):1271-1273 (1992).
Chang et al., "SV2 renders primed synaptic vesicles competent for Ca2+-induced exocytosis," Journal of Neuroscience, 29(4):883-897 (2009).
Chappell et al., "A re-examination of the role of basal forebrain cholinergic neurons in spatial working memory," Neuropharmacology, 37(4-5):481-487 (1998).
Colombo et al., "Spatial memory is related to hippocampal subcellular concentrations of calcium-dependent protein kinase C isoforms in young and aged rats," Proceedings of the National Academy of Science USA, 94(25):14195-14199 (1997).

Crook et al., "Age-associated memory impairment: Proposed diagnostic criteria and measures of clinical change—Report of a National Institute of Mental Health workgroup," Developmental Neuropsychology, 2:261-276 (1986).
Custer et al., "Synaptic vesicle protein 2 enhances release probability at quiescent synapses," Journal of Neurosicence, 26(4):1303-1313 (2006).
De Smedt et al., "Levetiracetam: the profile of a novel anticonvulsant drug-part I: preclinical data," CNS Drug Review, 13(1):43-56 (2007).
Estimating the Safe Starting Dose in Clinical Trials for Therapeutics in Adult Healthy Volunteers, Dec. 2002, Center for Biologics Evaluation and Research.
Folstein et al., ""Mini-mental state". A practical method for grading the cognitive state of patients for the clinician," Journal of Psychiatric Research, 12(3):189-198 (1975).
Fuks et al., "Localization and photoaffinity labelling of the levetiracetam binding site in rat brain and certain cell lines," European Journal of Pharmacology, 478(1):11-19 (2003).
Gallagher et al., "Relationship of age-related decline across several behavioral domains," Neurobiology of Aging, 10(6):691-708 (1989).
Gallagher et al., "Severity of spatial learning impairment in aging: development of a learning index for performance in the Morris water maze," Behavioral Neuroscience, 107(4):618-626 (1993).
Gillard et al., "Binding characteristics of levetiracetam to synaptic vesicle protein 2A (SV2A) in human brain and in CHO cells expressing the human recombinant protein," European Journal of Pharmacology, 536(1-2):102-108 (2006).
Hassel et al., "Up-regulation of hippocampal glutamate transport during chronic treatment with sodium valproate," Journal of Neurochemistry, 77:1285-1292 (2001).
Kenda et al., "Discovery of 4-Substituted Pyrrolidone Butanamidesas New Agents with Significant Antiepileptic Activity," Journal of Medicinal Chemistry, 47(3):530-549 (2004).
Kluger et al., "Neuropsychological Prediction of Decline to Dementia in Nondemented Elderly," Journal of Geriatric Psychiatry and Neurology, 12:168-179 (1999).
Larrabee, "Age-Associated Memory Impairment: Definition and psychometric characteristics," Aging, Neuropsychology, and Cognition, 3:118-131 (1996).
Loscher, "Valproate: a reappraisal of its pharmacodynamic properties and mechanisms of action," Progress in Neurobiology, 58:31-59 (1999).
Lynch et al., "The synaptic vesicle protein SV2A is the binding site for the antiepileptic drug levetiracetam," Proceedings of the National Academy of Science USA, 101(26):9861-9866 (2004).
Nicolle et al., "In vitro autoradiography of ionotropic glutamate receptors in hippocampus and striatum of aged Long-Evans rats: relationship to spatial learning," Neuroscience, 74(3):741-756 (1996).
Nicolle et al., "Metabotropic Glutamate Receptor-Mediated Hippocampal Phosphoinositide Turnover Is Blunted in Spatial Learning-Impaired Aged Rats," Journal of Neuroscience, 19(21):9604-9610 (1999).
Noyer et al., "The novel antiepileptic drug levetiracetam (ucb L059) appears to act via a specific binding site in CNS membranes," 286(2):137-146 (1995).
Owens et al., "Pharmacology of Divalproex," Psychopharmacology Bulletin 37 Suppl 2:17-24. (2003).
Petersen et al., "Mild cognitive impairment, clinical characterization and outcome," Arch. Neurology, 56:303-308 (1999).
Rapp et al., "Preserved neuron number in the hippocampus of aged rats with spatial learning deficits," Proceedings of the National Academy of Science USA, 93(18):9926-9930(1996).
Robbins et al., "Cambridge Neuropsychological Test Automated Battery (CANTAB): a factor analytic study of a large sample of normal elderly volunteers," Dementia, 5(5):266-281 (1994).
Smith et al., "Age-associated memory impairment diagnoses: problems of reliability and concerns for terminology," 6(4):551-558 (1991).
Yang et al., "Prolonged exposure to levetiracetam reveals a presynaptic effect on neurotransmission," 48(10):1861-1869 (2007).

(56) References Cited

OTHER PUBLICATIONS

Youngjohn et al., "Stability of everyday memory in age-associated impairment: A longitudinal study," Neuropsychology, 7(3);406-416 (1993).
Cramer et al., "Tolerability of levetiracetam in elderly patients with CNS disorders," Epilepsy Research, 56(2-3):135-145 (2003).
Meehan et al., "Levetiracetam has an activity-dependent effect on inhibitory transmission," Epilepsia, **(*):1-8 (2012) (published online on Jan. 31, 2012).
Muscas et al., "[Efficacy and tolerability of Levetiracetam in epileptic patients with acquired progressive cognitive impairment]," Bollettino—Lega Italiana contro l'Epilessia, 129-130:233-234 (2005) (full text English translation).
Takahashi et al., "Case report of sodium valproate treatment of aggression associated with Alzheimer's disease," Brain and Nerve (Tokyo), 48(8):757-760 (1996) (English Abstract only).
Albert et al., "The diagnosis of mild cognitive impairment due to Alzheimer's disease: Recommendations from the National Institute on Aging—Alzheimer's Association workgroups," Alzheimer's & Dementia 1-10 (2011).
Bakker et al., "Reduction of hippocampal hyperactivity improves cognition in amnestic mild cognitive impairment," Neuron, 74(3): 467-474 (2012).
Bertolucci et al., "Proposta de uma versão brasileira para a escala adcs-cgic," Arq Neuropsiquiatr 61(3-B):881-890 (2003) (English Abstract only).
Fattouch et al., "Intravenous Levetiracetam as first-line treatment of status epilepticus in the elderly," Acta. Neurol. Scand., 121(6):418-421 (2010).
Halgren et al., "Recall deficits produced by afterdischarges in the human hippocampal formation and amygdale," Electroencephalogr. Clin. Neurophysiol., 61(5):375-380 (1985).
Irizaary et al., "Incidence of new-onset seizures in mild to moderate Alzheimer disease," Arch. Neurol., 69(3):368-372 (2012).
Ito et al., "A case series of epilepsy-derived memory impairment resembling Alzheimer disease," Alzheimer Dis. Assoc. Disord., 23(4):406-409 (2009).
Kasteleijn-Nolst Trenité et al., "On-line detection of transient neuropsychological disturbances during EEG discharges in children with epilepsy," Dev. Med. Child Neurol., 32(1):46-50 (1990).
Klitgaard et al., "Evidence for a unique profile of levetiracetam in rodent models of seizures and epilepsy," Eur. J. Pharmacol., 353(2-3):191-206 (1998).
Kooi et al., "Alterations in mental function and paroxysmal cerebral activity," AMA Arch. Neurol. Psychiarty, 78(3):264-271 (1957).
Liedorp et al., "Prevalence and clinical significance of epileptiform EEG discharges in a large memory clinic cohort," Dement. Geriatr. Cogn. Disord., 29(5):432-437 (2010).
Löscher et al., "Profile of ucb L059, a novel anticonvulsant drug, in models of partial and generalized epilepsy in mice and rats," Eur. J. Pharmacol., 232(2-3):147-158 (1993).
Mendez et al., "Seizures in Alzheimer's disease: clinicopathologic study," J. Geriatr. Psychiatry Neurol., 7(4):230-233 (1994).
Patsalos, "Pharmacokinetic profile of levetiracetam: toward ideal characteristics," Pharmacol. Ther., 85(2):77-85 (2000).
Patsalos, "Clinical pharmacokinetics of levetiracetam," Clin. Pharmacokinet., 43(11):707-724 (2004).
Rao et al., "Recurrent seizures in patients with dementia: frequency, seizure types, and treatment outcome," Epilepsy Behav., 14(1):118-120 (2008).
Sargentini-Maier et al., "Brivaracetam Disposition in Renal Impairment," J. Clin. Pharmacol., published online Jan. 10, 2012.
Sargentini-Maier et al., "Pharmacokinetics and metabolism of $^{14}$C-brivaracetam, a novel SV2A ligand, in healthy subjects," Drug Metab Dispos, 36(1):36-45 (2007).
Scarmeas et al., "Seizures in Alzheimer disease: who, when, and how common?" Arch. Neurol., 66(8):992-997 (2009).
Schneider et al., "Validity and reliability of the Alzheimer's Disease Cooperative Study—Clinical Global Impression of Change," The Alzheimer's Disease Cooperative Study, Alzheimer Dis. Assoc. Disord., 11 Suppl. 2:S22-S32 (1997).
Doheny et al., "Blood and cerebrospinal fluid pharmacokinetics of the novel anticonvulsant levetiracetam (ucb L059) in the rat," Epilepsy Research, 34: 161-168 (1999).
Gillard et al., "Binding characteristics of brivaracetam, a selective, high affinity SV2A ligand in rat, mouse and human brain: relationship to anti-convulsant properties," European Journal of Pharmacology, 664:36-44 (2011).

* cited by examiner

METHODS AND COMPOSITIONS FOR IMPROVING COGNITIVE FUNCTION

This application is a continuation of U.S. application Ser. No. 12/580,464, filed Oct. 16, 2009, which claims the benefit of U.S. Provisional Patent Application 61/105,847, filed Oct. 16, 2008, U.S. Provisional Application 61/152,631, filed Feb. 13, 2009, and U.S. Provisional Application 61/175,536, filed May 5, 2009, the contents of each of which applications are herein incorporated by reference in their entirety.

GOVERNMENT CONTRACT

The invention was made under a contract with an agency of the United States government. The Government contract number is AG009973.

FIELD OF THE INVENTION

This invention relates to methods and compositions for treating age-related cognitive impairment. In particular, it relates to the use of inhibitors of synaptic vesicle glycoprotein 2A (SV2A) in treating age-related cognitive impairment in a subject in need or at risk thereof, including, without limitation, subjects having or at risk for Mild Cognitive Impairment (MCI), Age-Associated Memory Impairment (AAMI) or Age Related Cognitive Decline (ARCD).

BACKGROUND OF THE INVENTION

Cognitive ability may decline as a normal consequence of aging. Moreover, a significant population of elderly adults experiences a decline in cognitive ability that exceeds what is typical in normal aging.

Such age-related loss of cognitive function is characterized clinically by progressive loss of memory, cognition, reasoning, and judgment. Mild Cognitive Impairment (MCI), Age-Associated Memory Impairment (AAMI), Age-Related Cognitive Decline (ARCD) or similar clinical groupings are among those related to such age-related loss of cognitive function. According to some estimates, there are more than 16 million people with AAMI in the U.S. alone (Barker et al., 1995), and MCI is estimated to affect 5.5-7 million in the U.S. over the age of 65 (Plassman et al., 2008) There is, therefore, a need for effective treatment for age-related cognitive impairment and to improve cognitive function in patients diagnosed with MCI, AAMI, ARCD and similar age-associated cognitive impairments or at risk of developing them.

SUMMARY OF THE INVENTION

In accordance with a first aspect of the present invention, there is provided a method for treating age-related cognitive impairment in a subject in need or at risk thereof, the method comprising the step of administering to said subject a therapeutically effective amount of a synaptic vesicle protein 2A (SV2A) inhibitor or a pharmaceutically acceptable salt thereof. In certain embodiments of the invention, the SV2A inhibitor is selected from the group of SV2A inhibitors referred to in International Patent Application WO 2001/062726, International Patent Application WO 2002/094787, International Patent Application WO 2004/087658, U.S. Pat. No. 7,244,747, International Patent Application WO 2007/065595, US Patent Application 2008/0081832, International Patent Application WO 2006/128692, International Patent Application WO 2006/128693, UK Patent No. 1,039,113, and UK Patent No. 1,309,692. In certain embodiments of the invention, the SV2A inhibitor is selected from the group of levetiracetam, brivaracetam, and seletracetam or pharmaceutically acceptable salts thereof. In certain embodiments of the invention, the SV2A inhibitor or a pharmaceutically acceptable salt thereof is administered every 12 or 24 hours at a dose of about 0.1 to 5 mg/kg, or about 1 to 2 mg/kg, or about 0.1 to 0.2 mg/kg, or about 0.01 to 2.5 mg/kg, or about 0.1-2.5 mg/kg, or about 0.4-2.5 mg/kg, or about 0.6-1.8 mg/kg, or about 0.04-2.5 mg/kg or about 0.06-1.8 mg/kg.

In accordance with a second aspect of the present invention, there is provided a method for treating age-related cognitive impairment in a subject in need or at risk thereof, the method comprising the step of administering to said subject an SV2A inhibitor or a pharmaceutically acceptable salt thereof in combination with valproate or an analog or a derivative or a pharmaceutically acceptable salt thereof. In certain embodiments of the invention, valproate is administered at a daily dose such that the subject maintains a blood total valproate level of 0.5 to 5 µg/ml plasma, and the SV2A inhibitor is administered at a daily dose of is 0.01 to 1 mg/kg. In certain embodiments of the invention, valproate is administered at a daily dose such that the subject maintains a blood total valproate level of 0.5 to 5 µg/ml plasma, and the SV2A inhibitor is administered at a daily dose of 0.001 to 1 mg/kg. In certain embodiments of the invention, the SV2A inhibitor is selected from the group of SV2A inhibitors referred to in International Patent Application WO 2001/062726, International Patent Application WO 2002/094787, International Patent Application WO 2004/087658, U.S. Pat. No. 7,244,747, International Patent Application WO 2007/065595, US Patent Application 2008/0081832, International Patent Application WO 2006/128692, International Patent Application WO 2006/128693, UK Patent No. 1,039,113, and UK Patent No. 1,309,692. In certain embodiments of the invention, the SV2A inhibitor is selected from the group of levetiracetam, brivaracetam, and seletracetam or pharmaceutically acceptable salts thereof In certain embodiments of the invention, the SV2A inhibitor or a pharmaceutically acceptable salt thereof and valproate or an analog or a derivative or a pharmaceutically acceptable salt thereof are administered simultaneously, sequentially, or as a single formulation.

In accordance with a third aspect of the present invention, there is provided a pharmaceutical composition for improving cognitive function in a subject with age-related cognitive impairment or at risk thereof, the composition comprising a SV2A inhibitor or a pharmaceutically acceptable salt thereof In certain embodiments of the invention, the SV2A inhibitor is present in an amount of 5-140 mg. In other embodiments of the invention, the SV2A inhibitor is present in an amount of 0.7-180 mg.

In accordance with a fourth aspect of the present invention, there is provided a pharmaceutical composition for improving cognitive function in a subject with age-related cognitive impairment or at risk thereof, the composition comprising a SV2A inhibitor or a pharmaceutically acceptable salt thereof and valproate or an analog or a derivative or a pharmaceutically acceptable salt thereof. In certain embodiments of the invention, the SV2A inhibitor is present in an amount of 3-50 mg. In other embodiments of the invention, the SV2A inhibitor is present in an amount of 0.07-50 mg.

In accordance with a fifth aspect of the present invention, there is provided a method for treating age-related cognitive impairment in a subject in need or at risk thereof, the method comprising the step of administering to said subject a therapeutically effective amount of levetiracetam or a pharmaceutically acceptable salt thereof. In certain embodiments of the invention, levetiracetam or a pharmaceutically acceptable salt thereof is administered every 12 or 24 hours at a daily dose of about 1-2 mg/kg. In certain embodiments of the invention, levetiracetam or a pharmaceutically acceptable salt thereof is administered every 12 or 24 hours at a daily dose of about 70-150 mg. In some embodiments of the invention, levetiracetam or a pharmaceutically acceptable salt thereof is administered every 12 or 24 hours at a daily dose of about 0.1-2.5 mg/kg. In some embodiments of the invention, levetiracetam or a pharmaceutically acceptable salt thereof is administered every 12 or 24 hours at a daily dose of about 7-180 mg. In some embodiments of the invention, levetiracetam or a pharmaceutically acceptable salt thereof is administered every 12 or 24 hours at a daily dose of about 0.4-2.5 mg/kg. In some embodiments of the invention, levetiracetam or a pharmaceutically acceptable salt thereof is administered every 12 or 24 hours at a daily dose of about 25-180 mg. In some embodiments of the invention, levetiracetam or a pharmaceutically acceptable salt thereof is administered every 12 or 24 hours at a daily dose of about 0.6-1.8 mg/kg. In some embodiments of the invention, levetiracetam or a pharmaceutically acceptable salt thereof is administered every 12 or 24 hours at a daily dose of about 40-130 mg.

In accordance with a sixth aspect of the present invention, there is provided a method for treating age-related cognitive impairment in a subject in need or at risk thereof, the method comprising the step of administering to said subject a therapeutically effective amount of brivaracetam or a pharmaceutically acceptable salt thereof. In certain embodiments of the invention, brivaracetam or a pharmaceutically acceptable salt thereof is administered every 12 or 24 hours at a daily dose of about 0.1-0.2 mg/kg. In certain embodiments of the invention, brivaracetam or a pharmaceutically acceptable salt thereof is administered every 12 or 24 hours at a daily dose of about 7-15 mg. In some embodiments of the invention, brivaracetam or a pharmaceutically acceptable salt thereof is administered every 12 or 24 hours at a daily dose of about 0.01-2.5 mg/kg. In some embodiments of the invention, brivaracetam or a pharmaceutically acceptable salt thereof is administered every 12 or 24 hours at a daily dose of about 0.7-180 mg. In some embodiments of the invention, brivaracetam or a pharmaceutically acceptable salt thereof is administered every 12 or 24 hours at a daily dose of about 0.04-2.5 mg/kg. In some embodiments of the invention, brivaracetam or a pharmaceutically acceptable salt thereof is administered every 12 or 24 hours at a daily dose of about 2.5-180 mg. In some embodiments of the invention, brivaracetam or a pharmaceutically acceptable salt thereof is administered every 12 or 24 hours at a daily dose of about 0.06-1.8 mg/kg. In some embodiments of the invention, brivaracetam or a pharmaceutically acceptable salt thereof is administered every 12 or 24 hours at a daily dose of about 4-130 mg.

In accordance with a seventh aspect of the present invention, there is provided a method for treating age-related cognitive impairment in a subject in need or at risk thereof, the method comprising the step of administering to said subject a therapeutically effective amount of seletracetam or a pharmaceutically acceptable salt thereof.

DETAILED DESCRIPTION OF THE INVENTION

Figure 1:
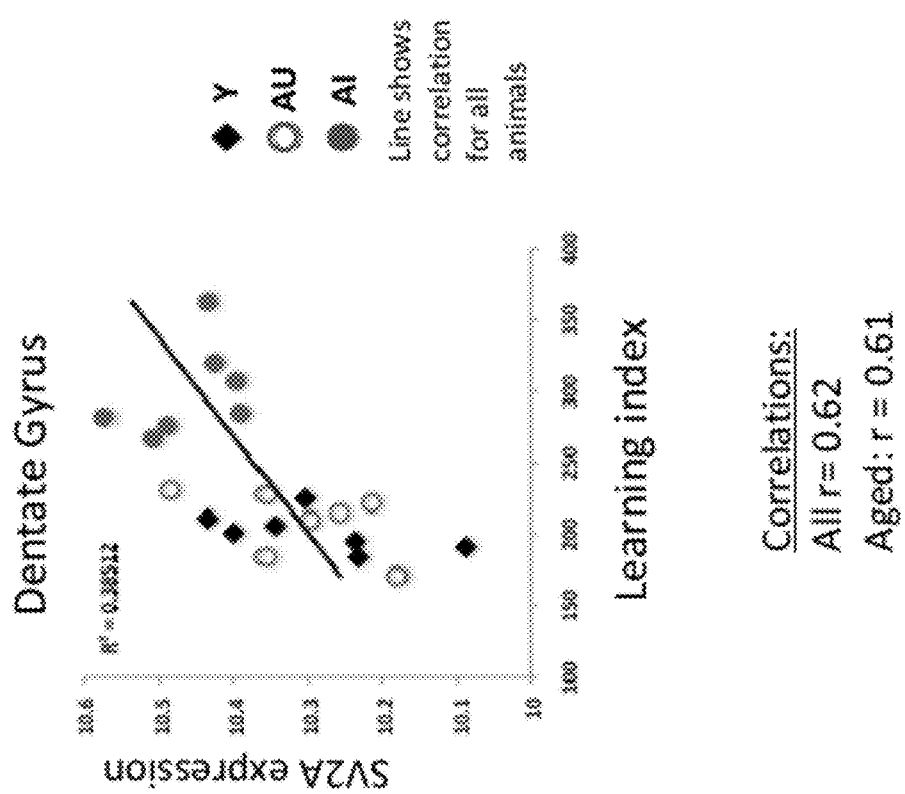
FIG. 1 depicts increased mRNA expression of the gene encoding SV2A in the dentate gyrus of the hippocampus of aged-impaired rats (AI) as compared to young rats (Y) and aged-unimpaired rats (AU). Normalized Affymetrix GeneChip probe set signal values (Y-axis), as a measure of mRNA expression, are plotted against learning indices of different rats, as a measure of cognitive impairment.

Unless otherwise defined herein, scientific and technical terms used in this application shall have the meanings that are commonly understood by those of ordinary skill in the art. Generally, nomenclature used in connection with, and techniques of, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present invention are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); Gilbert et al., "Developmental Biology, 6th ed.", Sinauer Associates, Inc., Sunderland, Mass. (2000).

Chemistry terms used herein are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to". "Including" and "including but not limited to" are used interchangeably.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents which are known with respect to structure, and those which are not known with respect to structure. The SV2A inhibitory activity of such agents may render them suitable as "therapeutic agents" in the methods and compositions of this invention.

A "patient", "subject", or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Cognitive function" or "cognitive status" refers to any higher order intellectual brain process or brain state, respectively, involved in learning and/or memory including, but not limited to, attention, information acquisition, information processing, working memory, short-term memory, long-term memory, anterograde memory, retrograde memory, memory retrieval, discrimination learning, decision-making, inhibitory response control, attentional set-shifting, delayed reinforcement learning, reversal learning, the temporal integration of voluntary behavior, and expressing an interest in one's surroundings and self-care.

In humans, cognitive function may be measured, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). See Folstein et al., *J Psychiatric Res* 12: 189-98, (1975); Robbins et al., Dementia 5: 266-81, (1994); Rey, L'examen clinique en psychologie, (1964); Kluger et al., *J Geriatr Psychiatry Neurol* 12:168-79, (1999).

In animal model systems, cognitive function may be measured in various conventional ways known in the art, including using a Morris Water Maze (MWM), Barnes circular maze, elevated radial arm maze, T maze or any other mazes in which the animals use spatial information. Other tests known in the art may also be used to assess cognitive function, such as novel object recognition and odor recognition tasks.

Cognitive function may also be measured using imaging techniques such as Positron Emission Tomography (PET), functional magnetic resonance imaging (fMRI), Single Photon Emission Computed Tomography (SPECT), or any other imaging technique that allows one to measure brain function. In animals, cognitive function may also be measured with electrophysiological techniques.

"Age-related cognitive impairment" or "cognitive impairment" refers to cognitive function in aged subjects that is not as robust as that expected in an age-matched normal subject (i.e. subjects with mean scores for a given age in a cognitive test) or as that expected in young adult subjects. In some cases, cognitive function is reduced by about 5%, about 10%, about 30%, or more, compared to cognitive function expected in an age-matched normal subject. In some cases, cognitive function is as expected in an age-matched normal subject, but reduced by about 5%, about 10%, about 30%, about 50% or more, compared to cognitive function expected in a young adult subject. Age-related impaired cognitive function may be associated with Mild Cognitive Impairment (MCI), Age-Associated Memory Impairment (AAMI), and Age-related Cognitive Decline (ARCD).

"Promoting" cognitive function refers to affecting age-related impaired cognitive function so that it more closely resembles the function of an aged-matched normal, unimpaired subject, or the function of a young adult subject. Cognitive function may be promoted to any detectable degree, but in humans preferably is promoted sufficiently to allow an impaired subject to carry out daily activities of normal life at the same level of proficiency as an aged-matched normal, unimpaired subject or as a young adult subject.

"Preserving" cognitive function refers to affecting normal or impaired cognitive function such that it does not decline or does not fall below that observed in the subject upon first presentation or diagnosis, or delays such decline.

"Improving" cognitive function includes promoting cognitive function and/or preserving cognitive function in a subject.

"Mild Cognitive Impairment" or "MCI" refers to a condition characterized by isolated memory impairment unaccompanied other cognitive abnormalities and relatively normal functional abilities. One set of criteria for a clinical characterization of MCI specifies the following characteristics: (1) memory complaint (as reported by patient, informant, or physician), (2) normal activities of daily living (ADLs), (3) normal global cognitive function, (4) abnormal memory for age (defined as scoring more than 1.5 standard deviations below the mean for a given age), and (5) absence of indicators of dementia (as defined by DSM-IV guidelines). Petersen et al., *Srch. Neurol.* 56: 303-308 (1999); Petersen, "Mild cognitive impairment: Aging to Alzheimer's Disease." Oxford University Press, N.Y. (2003).

Diagnosis of MCI usually entails an objective assessment of cognitive impairment, which can be garnered through the use of well-established neuropsychological tests, including the Mini Mental State Examination (MMSE), the Cambridge Neuropsychological Test Automated Battery (CANTAB) and individual tests such as Rey Auditory Verbal Learning Test (AVLT), Logical Memory Subtest of the revised Wechsler Memory Scale (WMS-R) and the New York University (NYU) Paragraph Recall Test. See Folstein et al., *J Psychiatric Res* 12: 189-98 (1975); Robbins et al., *Dementia* 5: 266-81 (1994); Kluger et al., *J Geriatric Psychiatry Neurol* 12:168-79 (1999).

"Age-Associate Memory Impairment (AAMI)" refers to a decline in memory due to aging. A patient may be considered to have AAMI if he or she is at least 50 years old and meets all of the following criteria: a) The patient has noticed a decline in memory performance, b) The patient performs worse on a standard test of memory compared to young adults, c) All other obvious causes of memory decline, except normal aging, have been ruled out (in other words, the memory decline cannot be attributed to other causes such as a recent heart attack or head injury, depression, adverse reactions to medication, Alzheimer's disease, etc.).

"Age-Related Cognitive Decline (ARCD)" refers to declines in memory and cognitive abilities that are a normal consequence of aging in humans (e.g., Craik & Salthouse, 1992). This is also true in virtually all mammalian species. Age-Associated Memory Impairment refers to older persons with objective memory declines relative to their younger years, but cognitive functioning that is normal relative to their age peers (Crook et al., 1986). Age-Consistent Memory Decline, is a less pejorative label which emphasizes that these are normal developmental changes (Crook, 1993; Larrabee, 1996), are not pathophysiological (Smith et al., 1991), and rarely progress to overt dementia (Youngjohn & Crook, 1993). The DSM-IV (1994) has codified the diagnostic classification of ARCD.

"Treating" a condition or patient refers to taking steps to obtain beneficial or desired results, including clinical results. Beneficial or desired clinical results include, but are not limited to, alleviation or amelioration of one or more symptoms associated with age-related cognitive impairment, delay or slowing of that impairment, amelioration, palliation or stabilization of that impairment, and other beneficial results, such as improvement of cognitive function or a reduced rate of decline of cognitive function in subjects with age-related cognitive impairment or at risk thereof.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitonealy, intravenously, subcutaneously, ocularly, sublingually, orally (by ingestion), intranasally (by inhalation), intraspinally, intracerebrally, and transdermally (by absorbtion, e.g., through a skin duct). A compound or agent can also appropriately be introduced by rechargable or biodegradable polymeric devices or other devices, e.g., patches and pumps, or formulations, which provide for the extended, slow or controlled release of the compound or agent. Administering can also be performed, for example, once, a plurality of times, and/or over one or more extended periods. In some aspects, the administration includes both direct administration, including self-administration, and indirect administration, including the act of prescribing a drug. For example, as used herein, a physician who instructs a patient to self-administer a drug, or to have the drug administered by another and/or who provides a patient with a prescription for a drug is administering the drug to the patient.

Appropriate methods of administering a substance, a compound or an agent to a subject will also depend, for example, on the age of the subject, whether the subject is active or inactive at the time of administering, whether the subject is cognitively impaired at the time of administering, the extent of the impairment, and the chemical and biological properties of the compound or agent (e.g. solubility, digestibility, bioavailability, stability and toxicity). Preferably, a compound or an agent is administered orally, e.g., to a subject by ingestion. In some embodiments, the orally administered compound or agent is in an extended release or slow release formulation, or administered using a device for such slow or extended release.

A "therapeutically effective amount" of a drug or agent is an amount of a drug or an agent that, when administered to a subject will have the intended therapeutic effect, e.g. improving cognitive function in a subject, e.g., a patient with age-related cognitive impairment or a patient at risk thereof. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, the nature and extent of the cognitive impairment, and the therapeutics or combination of therapeutics selected for administration, and the mode of administration. The skilled worker can readily determine the effective amount for a given situation by routine experimentation.

"Synaptic vesicle protein-2 (SV2)" is a family of synaptic vesicle proteins, which consists of three members, designated SV2A, SV2B, and SV2C. SV2A is the most widely distributed family member, being expressed ubiquitously in the brain. The proteins are integral membrane proteins and have a low-level homology (20-30%) to the twelve transmembrane family of bacterial and fungal transporter proteins that transport sugar, citrate, and xenobiotics (Bajjalieh et al., Science. 257: 1271-1273. (1992)). SV2 family proteins are present in the brain and endocrine cells, and further are present in all synaptic and endocrine vesicles. SV2 proteins are reported to play a role in normal synaptic function, and functions in a maturation step of primed vesicles that converts the vesicles into a Ca(2+)- and synaptotagmin-responsive state (Sudhof et al., 2009). Functionally, SV2 proteins are reported to enhance synaptic currents and increase the probability of transmitter release by maintaining the size of the readily releasable pool of vesicles (Custer et al., 2006).

"Inhibitor of SV2A" refers to any agent, substance or compound that binds to SV2A and reduces synaptic function by reducing pre-synaptic vesicle release (See, e.g., Noyer et al. 1995; Fuks et al. 2003; Lynch et al. 2004; Gillard et al. 2006; Custer et al., 2006; Smedt et al., 2007; Yang et al., 2007; and Example 8 of WO 2001/62726, all of which are specifically incorporated herein by reference.) A substance, or a compound or an agent is an inhibitor of SV2A even if it does not itself bind to SV2A, as long as it causes, or affects the ability of, another compound or agent to bind SV2A or reduce synaptic function by reducing pre-synaptic vesicle release. Inhibitors of SV2A, as used herein, include pharmaceutically acceptable salts and solvates of the inhibitors thereof.

Among the SV2A inhibitors useful for the methods and compositions of this invention, are those compounds or agents referred to in: i) International Patent Application WO 2001/062726; ii) International Patent Application WO 2002/094787; iii) International Patent Application WO 2004/087658; iv) U.S. Pat. No. 7,244,747; and v) International Patent Application WO 2007/065595. Applicants also refer to methods of preparing these compounds found in the documents cited above. Other synthetic methods may also be used. These methods are well known to those skilled in the art.

i) International Patent Application WO 2001/062726:

A compound having the formula I or a pharmaceutically acceptable salt thereof,

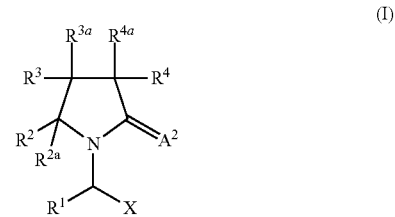

(I)

wherein X is —CA$^1$NR$^5$R$^6$ or —CA$^1$OR$^7$ or —CA$^1$-R$^8$ or CN;

A$^1$ and A$^2$ are independently oxygen, sulfur or —NR$^9$;

R$^1$ is hydrogen, alkyl, aryl or —CH$_2$—R$^{1a}$ wherein R$^{1a}$ is aryl, heterocycle, halogen, hydroxy, amino, nitro or cyano;

R$^2$, R$^3$ and R$^4$ are the same or different and each is independently hydrogen, halogen, hydroxy, thiol, amino, nitro, nitrooxy, cyano, azido, carboxy, amido, sulfonic acid, sulfonamide, alkyl, alkenyl, alkynyl, ester, ether, aryl, heterocycle, or an oxy derivative, thio derivative, amino derivative, acyl derivative, sulfonyl derivative or sulfinyl derivative;

R$^{2a}$, R$^{3a}$ and R$^{4a}$ are the same or different and each is independently hydrogen, halogen, alkyl, alkenyl, alkynyl or aryl;

R$^5$, R$^6$, R$^7$ and R$^9$ are the same or different and each is independently hydrogen, hydroxy, alkyl, aryl, heterocycle or an oxy derivative; and R$^8$ is hydrogen, hydroxy, thiol, halogen, alkyl, aryl, heterocycle or a thio derivative;

with the provisos that at least one of as R$^2$, R$^3$, R$^4$, R$^{2a}$, R$^{3a}$ and R$^{4a}$ is other than hydrogen; and that when the compound is a mixture of all possible isomers, X is —CONR$^5$R$^6$, A$^2$ is oxygen and R$^1$ is hydrogen, methyl, ethyl or propyl then substitution on the pyrollidine ring is other than mono-, di-, or tri-methyl or mono-ethyl; and that when R$^1$, R$^2$, R$^4$, R$^{2a}$, R$^{3a}$ and R$^{4a}$ are each hydrogen, A$^2$ is oxygen and X is CONR$^5$R$^6$ then R$^3$ is different from carboxy, ester, amido, substituted oxo-pyrrolidine, hydroxy, oxy derivative, amino, amino derivatives, methyl, naphthyl, phenyl optionally substituted by oxy derivatives or in the para position by an halogen atom.

In the definitions set forth below, unless otherwise stated, R$^{11}$ and R$^{12}$ are the same or different and each is independently amido, alkyl, alkenyl, alkynyl, acyl, ester, ether, aryl, aralkyl, heterocycle or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described below as substituents for alkyl.

The term "oxy derivative", as used herein is defined as including —O—R$^{11}$ wherein R$^{11}$ is as defined above except for "oxy derivative". Non-limiting examples are alkoxy, alkenyloxy, alkynyloxy, acyloxy, oxyester, oxyamido, alkylsulfonyloxy, alkylsulfinyloxy, arylsulfonyloxy, arylsulfinyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate.

The term "thio derivative" as used herein, is defined as including —S—R$^{11}$ groups wherein R$^{11}$ is as defined above except for "thio derivative". Non-limiting examples are alkylthio, alkenylthio, alkynylthio and arylthio.

The term "amino derivative" as used herein, is defined as including —NHR$^{11}$ or —NR$^{11}$R$^{12}$ groups wherein R$^{11}$ and R$^{12}$ are as defined above. Non-limiting examples are mono- or di-alkyl-, alkenyl-, alkynyl- and arylamino or mixed amino.

The term "acyl derivative" as used herein, represents a radical derived from carboxylic acid and thus is defined as including groups of the formula R$^{11}$—CO—, wherein R$^{11}$ is as defined above and may also be hydrogen. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "sulfonyl derivative" as used herein, is defined as including a group of the formula —SO$_2$—R$^{11}$, wherein R$^{11}$ is as defined above except for "sulfonyl derivative". Non-limiting examples are alkylsulfonyl, alkenylsulfonyl, alkynylsulfonyl and arylsulfonyl.

The term "sulfinyl derivative" as used herein, is defined as including a group of the formula —SO—R$^{11}$, wherein R$^{11}$ is as defined above except for "sulfinyl derivative". Non-limiting examples are alkylsulfinyl, alkenylsulfinyl, alkynylsulfinyl and arylsulfinyl.

The term "alkyl", as used herein, is defined as including saturated, monovalent hydrocarbon radicals having straight, branched or cyclic moieties or combinations thereof and containing 1-20 carbon atoms, preferably 1-6 carbon atoms for non-cyclic alkyl and 3-6 carbon atoms for cycloalkyl (in these two preferred cases, unless otherwise specified, "lower alkyl"). Alkyl moieties may optionally be substituted by 1 to 5 substituents independently selected from the group consisting of halogen, hydroxy, thiol, amino, nitro, cyano, thiocyanato, acyl, acyloxy, sulfonyl derivative, sulfinyl derivative, alkylamino, carboxy, ester, ether, amido, azido, cycloalkyl, sulfonic acid, sulfonamide, thio derivative, oxyester, oxyamido, heterocycle, vinyl, C1-5-alkoxy, C6-10-aryloxy and C6-10-aryl.

Preferred alkyl groups are methyl, ethyl, propyl, isopropyl, butyl, iso or ter-butyl, and 2,2,2-trimethylethyl each optionally substituted by at least one substituent selected from the group consisting of halogen, hydroxy, thiol, amino, nitro and cyano, such as trifluoromethyl, trichloromethyl, 2,2,2-trichloroethyl, 1,1-dimethyl-2,2-dibromoethyl, 1,1-dimethyl-2,2,2-trichloroethyl.

The term "alkenyl" as used herein, is defined as including both branched and unbranched, unsaturated hydrocarbon radicals having at least one double bond such as ethenyl (=vinyl), 1-methyl-1-ethenyl, 2,2-dimethyl-1-ethenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl, and the like and being optionally substituted by at least one substituent selected from the group consisting of halogen, hydroxy, thiol, amino, nitro, cyano, aryl and heterocycle such as mono- and di-halo vinyl where halo is fluoro, chloro or bromo.

The term "alkynyl" as used herein, is defined as including a monovalent branched or unbranched hydrocarbon radical containing at least one carbon-carbon triple bond, for example ethynyl, 2-propynyl (=propargyl), and the like and being optionally substituted by at least one substituent selected from the group consisting of halogen, hydroxy, thiol, amino, nitro, cyano, aryl and heterocycle, such as haloethynyl.

When present as bridging groups, alkyl, alkenyl and alkynyl represent straight- or branched chains, C1-12, preferably C1-4-alkylene or C2-12-, preferably C2-4-alkenylene or -alkynylene moieties respectively.

Groups where branched derivatives are conventionally qualified by prefixes such as "n", "sec", "iso" and the like (e.g., "n-propyl", "sec-butyl") are in the n-form unless otherwise stated.

The term "aryl" as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, thiol, amino, nitro, cyano, acyl, acyloxy, sulfonyl, sulfinyl, alkylamino, carboxy, ester, ether, amido, azido, sulfonic acid, sulfonamide, alkylsulfonyl, alkylsulfinyl, alkylthio, oxyester, oxyamido, aryl, C1-6-alkoxy, C6-10-aryloxy, C1-6-alkyl, C1-6-haloalkyl. Aryl radicals are preferably monocyclic containing 6-10 carbon atoms. Preferred aryl groups are phenyl and naphthyl each optionally substituted by 1 to 5 substituents independently selected from halogen, nitro, amino, azido, C1-6-alkoxy, C1-6-alkylthio, C1-6-alkyl, C1-6-haloalkyl and phenyl.

The term "halogen", as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —$NO_2$.

The term "nitrooxy", as used herein, represents a group of the formula —$ONO_2$.

The term "amino", as used herein, represents a group of the formula —$NH_2$.

The term "azido", as used herein, represents a group of the formula —$N_3$.

The term "carboxy", as used herein, represents a group of the formula —COOH.

The term "sulfonic acid", as used herein, represents a group of the formula —$SO_3H$.

The term "sulfonamide", as used herein, represents a group of the formula —$SO_2NH_2$.

The term "ester", as used herein is defined as including a group of formula —COO—$R^{11}$ wherein $R^{11}$ is as defined above except oxy derivative, thio derivative or amino derivative.

The term "ether" is defined as including a group selected from C1-50-straight or branched alkyl, or C2-50-straight or branched alkenyl or alkynyl groups or a combination of the same, interrupted by one or more oxygen atoms.

The term "amido" is defined as including a group of formula —$CONH_2$ or —$CONHR^{11}$ or —$CONR^{11}R^{12}$ wherein $R^{11}$ and $R^{12}$ are as defined above.

The term "heterocycle", as used herein is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl. Non-limiting examples of aromatic heterocycles are pyridyl, furyl, pyrrolyl, thienyl, isothiazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thieno(2,3-b)furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, phenanthridinyl, acridinyl, perimidinyl, phenanthrolinyl, phenothiazinyl, furazanyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl optionally substituted by alkyl or as described above for the alkyl groups. Non-limiting examples of non aromatic heterocycles are tetrahydrofuranyl, tetrahydropyranyl, piperidinyl, piperidyl, piperazinyl, imidazolidinyl, morpholino, morpholinyl, 1-oxaspiro(4.5)dec-2-yl, pyrrolidinyl, 2-oxo-pyrrolidinyl, sugar moieties (i.e. glucose, pentose, hexose, ribose, fructose, which may also be substituted) or the same which can optionally be substituted with any suitable group, including but not limited to one or more moieties selected from lower alkyl, or other groups as described above for the alkyl groups. The term "heterocycle" also includes bicyclic, tricyclic and tetracyclic, spiro groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1)heptanyl, 8-azabicyclo(3.2.1)octanyl.

In the above definitions it is to be understood that when a substituent such as $R^2$, $R^3$, $R^4$, $R^{2a}$, $R^{3a}$, $R^{4a}$, $R^5$, $R^6$, $R^7$, $R^8$ is attached to the rest of the molecule via a heteroatom or a carbonyl, a straight- or branched chain, C1-12-, preferably C1-4-alkylene or C2-12, preferably C2-4-alkenylene or -alkynylene bridge may optionally be interposed between the heteroatom or the carbonyl and the point of attachment to the rest of the molecule.

Preferred examples of X are —COO $R^7$ or —$CONR^5R^6$, wherein $R^5$, $R^6$ and $R^7$ are preferably hydrogen, C1-4-alkyl, phenyl or alkylphenyl.

Preferably X is carboxy or —$CONR^5R^6$, wherein $R^5$ and $R^6$ are preferably hydrogen, C1-4-alkyl, phenyl or alkylphenyl, especially —$CONH_2$.

Preferably $A^1$ and $A^2$ are each oxygen.

Preferably $R^1$ is hydrogen, alkyl, especially C1-12 alkyl, particularly lower alkyl or aryl especially phenyl.

Examples of preferred $R^1$ groups are methyl, ethyl, propyl, isopropyl, butyl, iso- or ter-butyl, 2,2,2-trimethylethyl each optionally attached via a methylene bridge or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

$R^1$ as ethyl is especially preferred.

Preferably $R^2$ and $R^{2a}$ are independently hydrogen, halogen or alkyl, especially lower alkyl.

Examples of preferred $R^2$ and $R^{2a}$ groups are independently hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

Especially at least one and most preferably both of $R^2$ and $R^{2a}$ are hydrogen.

Preferably $R^{3a}$, $R^4$ and $R^{4a}$ are independently hydrogen, alkyl, especially methyl or ethyl or aryl especially phenyl or aralkyl, especially benzyl.

Examples of preferred $R^{3a}$, $R^4$ and $R^{4a}$ groups are independently hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

Especially at least one and most preferably both of $R^4$ and $R^{4a}$ are hydrogen.

$R^{3a}$ is particularly hydrogen or alkyl, especially lower alkyl and is most preferably hydrogen.

Preferably $R^3$ is hydrogen, C1-12-alkyl, especially C1-6-alkyl, each optionally substituted by one or more substituents selected from hydroxy, halogen, cyano, thiocyanato or alkoxy and attached to the ring either directly or via a thio, sulfinyl, sulfonyl, carbonyl or oxycarbonyl group and optionally, a C1-4-alkylene bridge, particularly methylene; C2-6-alkenyl or -alkynyl, especially C2-3-alkenyl or -alkynyl each optionally substituted by one or more halogens; azido; cyano; amido; carboxy; triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl or piperazinyl each optionally substituted by one or more substituents selected from halogen, C1-6-alkyl and phenyl and attached to the ring either directly or via a carbonyl group or a C1-4-alkylene bridge, particularly methylene; naphthyl; or phenyl, phenylalkyl or phenylalkenyl each optionally substituted by one or more substituents selected from halogen, C1-6-alkyl, C1-6 haloalkyl, C1-6-alkoxy, C1-6-alkylthio, amino, azido, phenyl and nitro and each attached to the ring either directly or via an oxy, sulfonyl, sulfonyloxy, carbonyl or carbonyloxy group and optionally additionally a C1-4-alkylene bridge, particularly methylene.

Also, preferably, $R^3$ is C1-6-alkyl optionally substituted by one or more substituents selected from halogen, thiocyanato, azido, alkoxy, alkylthio, phenylsulfonyl; nitrooxy; C2-3-alkenyl or -alkynyl each optionally substituted by one or more halogens or by acetyl; tetrazolyl, pyridyl, furyl, pyrrolyl, thiazolyl or thienyl; or phenyl or phenylalkyl each optionally substituted by one or more substituents selected from halogen, C1-6-alkyl, C1-6 haloalkyl, C1-6-alkoxy, amino, azido, phenyl and nitro and each attached to the ring either directly or via a sulfonyloxy and optionally additionally a C1-4-alkylene bridge, particularly methylene.

Other examples of preferred $R^3$ groups are hydrogen, halogen or methyl, ethyl, propyl, isopropyl, butyl, iso or ter-butyl, 2,2,2-trimethylethyl or the same substituted by at least one halogen atom such as trifluoromethyl, trichloromethyl, 2,2,2-trichloroethyl, 1,1-dimethyl-2,2-dibromoethyl, 1,1-dimethyl-2,2,2-trichloroethyl.

$R^3$ is especially C1-4-alkyl optionally substituted by one or more substituents selected from halogen, thiocyanato or azido; C2-5-alkenyl or -alkynyl, each optionally substituted by one or more halogens; thienyl; or phenyl optionally substituted by one or more substituents selected from halogen, C1-6-alkyl, C1-6 haloalkyl or azido.

Further examples of preferred $R^3$ groups are C1-6 alkyl and C2-6 haloalkenyl.

Preferably $R^5$ and $R^6$ are independently hydrogen, methyl, ethyl, propyl, isopropyl, butyl, iso or ter-butyl, 2,2,2-trimethylethyl, especially hydrogen or methyl.

Especially at least one and most preferably both of $R^5$ and $R^6$ are hydrogen.

Preferably $R^7$ is hydrogen, methyl, ethyl, propyl, isopropyl, butyl, iso or tert-butyl, 2,2,2-trimethylethyl, methoxy, ethoxy, phenyl, benzyl or the same substituted by at least one halogen atom such as trifluoromethyl, chlorophenyl.

Preferably $R^7$ is hydrogen, methyl or ethyl especially hydrogen.

Preferably $R^8$ is hydrogen, methyl, ethyl, propyl, isopropyl, butyl, iso or ter-butyl, 2,2,2-trimethylethyl, phenyl, benzyl or the same substituted by at least one halogen atom such as trifluoromethyl, chlorobenzyl.

Preferably $R^8$ is hydrogen or methyl.

Combinations of one or more of these preferred compound groups are especially preferred.

A particular group of compounds of formula I (Compounds 1A) comprises those wherein, $A^2$ is oxygen;

X is —$CONR^5R^6$ or —$COOR^7$ or —CO—$R^8$ or CN;

$R^1$ is hydrogen or alkyl, aryl, halogen, hydroxy, amino, nitro, cyano;

$R^2$, $R^3$, $R^4$, are the same or different and each is independently hydrogen or halogen, hydroxy, amino, nitro, cyano, acyl, acyloxy, a sulfonyl derivative, a sulfinyl derivative, an amino derivative, carboxy, ester, ether, amido, sulfonic acid, sulfonamide, alkoxycarbonyl, a thio derivative, alkyl, alkoxy, oxyester, oxyamido, aryl, an oxy derivative, heterocycle, vinyl and $R^3$ may additionally represent C2-5 alkenyl, C2-5 alkynyl or azido each optionally substituted by one or more halogen, cyano, thiocyano, azido, cyclopropyl, acyl and/or phenyl; or phenylsulfonyloxy whereby any phenyl moiety may be substituted by one or more halogen, alkyl, haloalkyl, alkoxy, nitro, amino, and/or phenyl; most preferably methyl, ethyl, propyl, isopropyl, butyl, or isobutyl.

$R^{2a}$, $R^{3a}$ and $R^{4a}$ are hydrogen;

$R^5$, $R^6$, $R^7$ are the same or different and each is independently hydrogen, hydroxy, alkyl, aryl, heterocycle or oxy derivative; and $R^8$ is hydrogen, hydroxy, thiol, halogen, alkyl, aryl, heterocycle, alkylthio or thio derivative.

Within these Compounds 1A, $R^1$ is preferably methyl, ethyl, propyl, isopropyl, butyl, or isobutyl; most preferably methyl, ethyl or n-propyl.

$R^2$ and $R^4$ are preferably independently hydrogen or halogen or methyl, ethyl, propyl, isopropyl, butyl, isobutyl; and, most preferably, are each hydrogen.

$R^3$ is preferably C1-5 alkyl, C2-5 alkenyl, C2-05 alkynyl, cyclopropyl, azido, each optionally substituted by one or more halogen, cyano, thiocyano, azido, alkylthio, cyclopropyl, acyl and/or phenyl; phenyl; phenylsulfonyl; phenylsulfonyloxy, tetrazole, thiazole, thienyl, furyl, pyrrole, pyridine, whereby any phenyl moiety may be substituted by one or more halogen, alkyl, haloalkyl, alkoxy, nitro, amino, and/or phenyl; most preferably methyl, ethyl, propyl, isopropyl, butyl, or isobutyl.

X is preferably —COOH or —COOMe or —COOEt or —$CONH_2$; most preferably —$CONH_2$.

A further particular group of compounds of formula I (Compounds 1B) comprises those wherein, X is —$CA^1NH_2$, —$CA^1NHCH_3$ or —$CA^1N(CH_3)_2$;

$R^1$ is alkyl or phenyl;

$R^3$ is alkyl, alkenyl, alkynyl, cyano, isothiocyanato, ether, carboxyl, amido, aryl, heterocycle; or $R^3$ is $CH_2R^{10}$ wherein $R^{10}$ is hydrogen, cycloalkyl, oxyester, oxyalkylsulfonyl, oxyarylsufonyl, aminoalkylsulfonyl, aminoarylsulfonyl, nitrooxy, cyano, isothiocyanato, azido, alkylthio, arylthio, alkylsulfinyl, alkylsulfonyl, heterocycle, aryloxy, alkoxy or trifluoroethyl;

$R^{3a}$ is hydrogen, alkyl or aryl (especially with the proviso that when $R^{3a}$ is hydrogen, $R^3$ other than methyl);

or $R^3R^{3a}$ form a cycloalkyl;

and $R^2$, $R^{2a}$, $R^4$ and $R^{4a}$ are each hydrogen.

Within the compounds of formula I, $R^1$ is preferably alkyl especially C1-12- more particularly C1-6-alkyl and is most preferably ethyl;

$R^2$, $R^{2a}$, $R^{3a}$ and $R^{4a}$ are preferably hydrogen;

$R^3$ is preferably selected from hydrogen; C1-12-alkyl, especially C1-6-alkyl, each optionally substituted by one or more substituents selected from hydroxy, halogen, cyano, thiocyanato or alkoxy and attached to the ring either directly or via a thio, sulfinyl, sulfonyl, carbonyl or oxycarbonyl group and optionally additionally a C1-4-alkylene bridge, particularly methylene; C2-6-alkenyl or -alkynyl, especially C2-3-alkenyl or -alkynyl, each optionally substituted by one or more halogens; azido; cyano; amido; carboxy; triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl or piperazinyl each optionally substituted by one or more substituents selected from halogen, C1-6-alkyl and phenyl and attached to the ring either directly or via a carbonyl group or a C1-4-alkylene bridge, particularly methylene; naphthyl; or phenyl, phenylalkyl or phenylalkenyl each optionally substituted by one or more substituents selected from halogen, C1-6-alkyl, C1-6 haloalkyl, C1-6-alkoxy, C1-6-alkylthio, amino, azido, phenyl and nitro and each attached to the ring either directly or via an oxy, sulfonyl, sulfonyloxy, carbonyl or carbonyloxy group and optionally additionally a C1-4-alkylene bridge, particularly methylene;

$R^{3a}$ is preferably hydrogen or C1-4-alkyl;

$R^4$ and $R^{4a}$ are preferably, independently hydrogen, C1-4-alkyl, phenyl or benzyl.

A further group of compounds of formula I (Compounds 1C) comprises those in racemic form wherein, when X is —CONR$^5$R$^6$ and R$^1$ is hydrogen, methyl, ethyl or propyl, then substitution on the pyrrolidine ring is other than mono-, di-, or tri-methyl or mono-ethyl.

A further group of compound of formula I (Compounds 1D) comprises those in racemic form wherein, when X is —CONR$^5$R$^6$ and R$^1$ is hydrogen or C1-6-alkyl, C2-6-alkenyl or -alkynyl or cycloalkyl, each unsubstituted, then substitution in the ring is other than by alkyl, alkenyl or alkynyl, each unsubstituted.

A further particular group of compounds of formula I (Compounds IE) comprises those wherein, X is —CA$^1$NH$_2$;

R$^1$ is H;

R$^3$ is azidomethyl, iodomethyl, ethyl optionally substituted by 1 to 5 halogen atoms, n-propyl optionally substituted by 1 to 5 halogen atoms, vinyl optionally subsituted by one or two methyl, and/or 1 to 3 halogen atoms, acetylene optionally substituted by C1-4-alkyl, phenyl or halogen;

$R^{3a}$ is hydrogen or halogen, preferably fluorine;

and $R^2$, $R^{2a}$, $R^4$ and $R^{4a}$ are each hydrogen;

as their racemates or in enantiomerically enriched form, preferably the pure enantiomers.

A further particular group of compounds of formula I (Compounds 1F) comprises those wherein, X is —CA$^1$NH$_2$;

R$^1$ is H;

R$^3$ is C1-6-alkyl, C2-6-alkenyl or C2-6-alkynyl optionally substituted by azido, oxynitro, 1 to 6 halogen atoms;

$R^{3a}$ is hydrogen or halogen, preferably fluorine;

and $R^2$, $R^{2a}$, $R^4$ and $R^{4a}$ are each hydrogen; as their racemates or in enantiomerically enriched form, preferably the pure enantiomers.

In all the above mentioned scopes when the carbon atom to which R$^1$ is attached is asymmetric it is preferably in the "S"-configuration.

In some embodiments, compounds useful in the methods and compositions of this invention are selected from the group consisting of:

(2S)-2-[4-(bromomethyl)-2-oxo-1-pyrrolidinyl]butanamide;
(2S)-2-[(4R)-4-(iodomethyl)-2-oxopyrrolidinyl]butanamide;
(2S)-2-(2-oxo-4-phenyl-1-pyrrplidinyl)butanamide;
(2S)-2-[4-(iodomethyl)-2-oxo-1-pyrrolidinyl]butanamide;
(2S)-2-[4-(chloromethyl)-2-oxo-1-pyrrolidinyl]butanamide;
{1-[(1S)-1-(aminocarbonyl)propyl]-5-oxo-3-pyrrolidinyl}methyl 4-methylbenzenesulfonate;
(2S)-2-[(4R)-4-(azidomethyl)-2-oxopyrrolidinyl]butanamide;
2-[4-(2,2-dibromovinyl)-2-oxo-1-pyrrolidinyl]butanamide;
{1-[(1S)-1-(aminocarbonyl)propyl]-5-oxo-3-pyrrolidinyl}methyl nitrate;
(2S)-2-[2-oxo-4-(1H-tetraazol-1-ylmethyl)-1-pyrrolidinyl]butanamide;
2-(2-oxo-4-vinyl-1-pyrrolidinyl)butanamide;
2-{2-oxo-4-[(phenylsulfonyl)methyl]-1-pyrrolidinyl]butanamide;
(2S)-2-[(4R)-4-(2,2-dibromovinyl)-2-oxopyrrolidinyl]butanamide;
(2S)-2-[(4S)-4-(2,2-dibromovinyl)-2-oxopyrrolidinyl]butanamide;
(2S)-2-[4-(isothiocyanatomethyl)-2-oxo-1-pyrrolidinyl]butanamide;
2-[2-oxo-4-(1,3-thiazol-2-yl)-1-pyrrolidinyl]butanamide;
(2S)-2-[2-oxo-4-(2-thienyl)-1-pyrrolidinyl]butanamide;
(2S)-2-[4-(2-methoxyphenyl)-2-oxo-1-pyrrolidinyl]butanamide;
(2S)-2-[4-(3-methoxyphenyl)-2-oxo-1-pyrrolidinyl]butanamide;
(2S)-2-[4-(4-azidophenyl)-2-oxo-1-pyrrolidinyl]butanamide;
(2S)-2-[2-oxo-4-(3-thienyl)-1-pyrrolidinyl]butanamide;
(2S)-2-[4-(3-azidophenyl)-2-oxo-1-pyrrolidinyl]butanamide;
(2S)-2-[2-oxo-4-(3-thienyl)-1-pyrrolidinyl]butanamide;
(2S)-2-[(4S)-2-oxo-4-vinylpyrrolidinyl]butanamide;
(2S)-2-[(4R)-2-oxo-4-vinylpyrrolidinyl]butanamide;
2-[4-(2-bromophenyl)-2-oxo-1-pyrrolidinyl]butanamide;
2-[2-oxo-4-(3-pyridinyl)-1-pyrrolidinyl]butanamide;
(2S)-2-(4-[1,1'-biphenyl]-4-yl-2-oxo-1-pyrrolidinyl)butanamide;
(2S)-2-{4-[(methylsulfanyl)methyl]-2-oxo-1-pyrrolidinyl}butanamide;
2-[4-(iodomethyl)-2-oxo-1-pyrrolidinyl]butanamide;
(2S)-2-[(4R)-4-(iodomethyl)-2-oxo-1-pyrrolidinyl]pentanamide;
(2S)-2-[(4R)-4-(iodomethyl)-2-oxopyrrolidinyl]propanamide;
2-(2-oxo-4-propyl-1-pyrrolidinyl)propanamide;
2-(2-oxo-4-propyl-1-pyrrolidinyl)butanamide;
2-(2-oxo-4-pentyl-1-pyrrolidinyl)butanamide;
(2S)-2-[(4R)-4-(iodomethyl)-2-oxopyrrolidinyl]-N-methylbutanamide;
(2S)-2-(4-neopentyl-2-oxo-1-pyrrolidinyl)butanamide;
(2S)-2-(4-ethyl-2-oxo-1-pyrrolidinyl)butanamide;
2-[4-(2,2-difluorovinyl)-2-oxo-1-pyrrolidinyl]butanamide;
2-[4-(2,2-difluoroethyl)-2-oxo-1-pyrrolidinyl]butanamide;
(2S)-2-[(4S)-2-oxo-4-propylpyrrolidinyl]butanamide;
(2S)-2-[(4R)-2-oxo-4-propylpyrrolidinyl]butanamide;
2-{4-[(Z)-2-fluoroethenyl]-2-oxo-1-pyrrolidinyl}butanamide;
2-[4-(2-methyl-1-propenyl)-2-oxo-1-pyrrolidinyl]butanamide;
2-(4-butyl-2-oxo-1-pyrrolidinyl)butanamide;
2-[4-(cyclopropylmethyl)-2-oxo-1-pyrrolidinyl]butanamide;
2-(4-isobutyl-2-oxo-1-pyrrolidinyl)butanamide;
2-[4-(4-chlorophenyl)-2-oxo-1-pyrrolidinyl]butanamide;
2-[4-(3-chlorophenyl)-2-oxo-1-pyrrolidinyl]butanamide;
2-{2-oxo-4-[2-(trifluoromethyl)phenyl]-1-pyrrolidinyl}butanamide;
2-[4-(2-fluorophenyl)-2-oxo-1-pyrrolidinyl]butanamide;
2-[4-(3-methylphenyl)-2-oxo-1-pyrrolidinyl]butanamide;
(2S)-2-[2-oxo-4-(2-phenylethyl)-1-pyrrolidinyl]butanamide;
(2S)-2-[4-(3-bromophenyl)-2-oxo-1-pyrrolidinyl]butanamide;
2-{4-[3,5-bis(trifluoromethyl)phenyl]-2-oxo-1-pyrrolidinyl}butanamide;
2-[4-(3,4-dichlorophenyl)-2-oxo-1-pyrrolidinyl]butanamide;
2-[4-(2,4-dichlorophenyl)-2-oxo-1-pyrrolidinyl]butanamide;
2-[4-(2-furyl)-2-oxo-1-pyrrolidinyl]butanamide;
(2S)-2-[2-oxo-4-(3-phenylpropyl)-1-pyrrolidinyl]butanamide;

(2S)-2-[4-(3,5-dibromophenyl)-2-oxo-1-pyrrolidinyl]butanamide;
2-[4-(3,4-dichlorophenyl)-2-oxo-1-pyrrolidinyl]butanamide;
2-(2-oxo-4-propyl-1-pyrrolidinyl)butanamide;
2-[4-(3-chlorophenyl)-2-oxo-1-pyrrolidinyl]butanamide;
2-(4-ethynyl-2-oxo-1-pyrrolidinyl)butanamide;
2-[4-(2-fluorophenyl)-2-oxo-1-pyrrolidinyl]butanamide;
(2S)-2-[4-(cyclopropylmethyl)-2-oxo-1-pyrrolidinyl}butanamide;
(2S)-2-[(4S)-4-(2,2-difluorovinyl)-2-oxopyrrolidinyl]butanamide;
(2S)-2-[2-oxo-4-(3,3,3-trifluoropropyl)-1-pyrrolidinyl]butanamide;
2-[4-(3-methylphenyl)-2-oxo-1-pyrrolidinyl]butanamide;
(2S)-2-[4-(cyclopropylmethyl)-2-oxo-1-pyrrolidinyl]butanamide;
(2S)-2-[(4R)-4-(2,2-difluorovinyl)-2-oxopyrrolidinyl]butanamide;
(2S)-2-[2-oxo-4-(1H-pyrrol-1-yl)-1-pyrrolidinyl]butanamide;
(2S)-2-(4-allyl-2-oxo-1-pyrrolidinyl)butanamide;
(2S)-2-[4-(2-iodopropyl)-2-oxo-1-pyrrolidinyl}butanamide;
(2S)-2-(4-allyl-2-oxo-1-pyrrolidinyl)butanamide;
(2S)-2-[2-oxo-4-(2-oxopropyl)-1-pyrrolidinyl]butanamide;
(2S)-2-[4-(2-bromo-1H-pyrrol-1-yl)-2-oxo-1-pyrrolidinyl]butanamide;
(2S)-2-(4-methyl-2-oxo-4-propyl-1-pyrrolidinyl)butanamide;
(2R)-2-[4-(2,2-dichlorovinyl)-2-oxo-1-pyrrolidinyl]butanamide;
2-[4-(bromoethynyl)-2-oxo-1-pyrrolidinyl]butanamide;
2-[(4S)-4-(2,2-difluoropropyl)-2-oxopyrrolidinyl]butanamide;
(2S)-2-[4-(bromoethynyl)-2-oxo-1-pyrrolidinyl]butanamide;
2-(2-oxo-4-propyl-1-pyrrolidinyl)pentanamide;
3-cyclopropyl-2-(2-oxo-4-propyl-1-pyrrolidinyl)propanamide;
2-(2-oxo-4-propyl-1-pyrrolidinyl)-3-(1,3-thiazol-4-yl)propanamide;
2-(2-oxo-4-propyl-1-pyrrolidinyl)-4-pentenamide;
(2S)-2-[(4R)-2-oxo-4-vinylpyrrolidinyl]butanamide;
including all isomeric forms and mixtures thereof or a pharmaceutically acceptable salt thereof.

In some embodiments, compounds useful in the methods and compositions of this invention are selected from the group consisting of:
(2S)-2-[(4S)-4-(2,2-difluorovinyl)-2-oxopyrrolidinyl]butanamide;
(2S)-2-[(4S)-2-oxo-4-propylpyrrolidinyl]butanamide;
(2S)-2-[(4R)-2-oxo-4-propylpyrrolidinyl]butanamide.

ii) International Patent Application WO 2002/094787: Compounds of the formula I

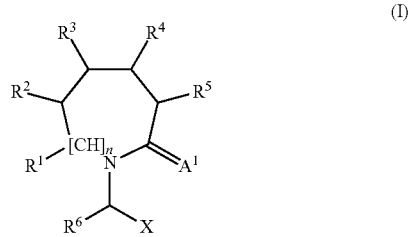

wherein n represents 0 or 1 whereby $R^1$ is not existent when n=0 and $R^1$ is existent when n=1;
$A^1$ represents an oxygen or a sulfur atom;
X is —$CONR^7R^8$, —$COOR^9$, —CO—$R^{10}$ or CN;
$R^1$ when existent, $R^2$, $R^3$, $R^4$ and $R^5$ are the same or different and each is independently hydrogen, halogen, hydroxy, thiol, amino, nitro, nitrooxy, cyano, azido, carboxy, amido, sulfonic acid, sulfonamide, alkyl, alkenyl, alkynyl, ester, ether, aryl, heterocycle, or an oxy derivative, thio derivative, amino derivative, acyl derivative, sulfonyl derivative or sulfinyl derivative,
provided that at least one of the substituents R chosen from $R^1$ when existent, $R^2$, $R^3$, $R^4$ or $R^5$ is not hydrogen;
$R^6$ is hydrogen, alkyl, aryl or —$CH_2$—$R^{6a}$ wherein $R^{6a}$ is aryl, heterocycle, halogen, hydroxy, amino, nitro or cyano;
$R^7$, $R^8$ and $R^9$ are the same or different and each is independently hydrogen, hydroxy, alkyl, aryl, heterocycle or an oxy derivative; and
$R^{10}$ is hydrogen, hydroxy, thiol, halogen, alkyl, aryl, heterocycle or a thio derivative;
their pharmaceutically acceptable salts, geometrical isomers (including cis and trans, Z and E isomers), enantiomers, diastereoisomers and mixtures thereof (including all possible mixtures of stereoisomers).

In the above formula, at least one substituent $R^1$ to $R^5$ is different from hydrogen. Some non-substituted compounds are referred to in U.S. Pat. Nos. 5,468,733 and 5,516,759. U.S. Pat. No. 5,468,733 refers to non-ring substituted 2-oxo-1-pyrrolidinyl and 2-oxo-1-piperidinyl derivatives as inhibitors of the oncogene Ras protein. In particular, these compounds block the ability of Ras to transform normal cells to cancer cells, and therefore can be included in several chemotherapeutic compositions for treating cancer.

U.S. Pat. No. 5,516,759 refers to non-ring substituted 2-oxo-1-pyrrolidinyl, 2-oxo-1-piperidinyl and azepanyl derivatives present at the N-terminus of dodecapeptides possessing LHRH (luteinizing hormone-releasing hormone) antagonistic activity. Such LHRH antagonists are useful in the treatment of a variety of conditions in which suppression of sex steroids plays a key role including contraception, delay of puberty, treatment of benign prostatic hyperplasia a. o.

In the definitions set forth below, unless otherwise stated, $R^{11}$ and $R^{12}$ are the same or different and each is independently amido, alkyl, alkenyl, alkynyl, acyl, ester, ether, aryl, aralkyl. heterocycle or an oxy derivative, thio derivative, acyl derivative, amino derivative, sulfonyl derivative, or sulfinyl derivative, each optionally substituted with any suitable group, including, but not limited to, one or more moieties selected from lower alkyl or other groups as described below as substituents for alkyl.

The term "oxy derivative", as used herein, is defined as including —O—$R^{11}$ groups wherein $R^{11}$ is as defined above except for "oxy derivative". Non-limiting examples are alkoxy, alkenyloxy, alkynyloxy, acyloxy, oxyester, oxyamido, alkylsulfonyloxy, alkylsulfinyloxy, arylsulfonyloxy, arylsulfinyloxy, aryloxy, aralkoxy or heterocyclooxy such as pentyloxy, allyloxy, methoxy, ethoxy, phenoxy, benzyloxy, 2-naphthyloxy, 2-pyridyloxy, methylenedioxy, carbonate.

The term "thio derivative", as used herein, is defined as including —S—$R^{11}$ groups wherein $R^{11}$ is as defined above except for "thio derivative". Non-limiting examples are alkylthio, alkenylthio, alkynylthio and arylthio.

The term "amino derivative", as used herein, is defined as including —$NHR^{11}$ or —$NR^{11}R^{12}$ groups wherein $R^{11}$ and $R^{12}$ are as defined above. Non-limiting examples are mono- or di-alkyl-, alkenyl-, alkynyl- and arylamino or mixed amino.

The term "acyl derivative", as used herein, represents a radical derived from carboxylic acid and thus is defined as including groups of the formula $R^{11}$—CO—, wherein $R^{11}$ is as defined above and may also be hydrogen. Preferred are acyl derivatives of formula —$COR^{11}$ wherein $R^{11}$ is selected from hydrogen, C1-12 alkyl, C2-12 alkenyl, C2-12 alkenyl, heterocyle and aryl. Non-limiting examples are formyl, acetyl, propionyl, isobutyryl, valeryl, lauroyl, heptanedioyl, cyclohexanecarbonyl, crotonoyl, fumaroyl, acryloyl, benzoyl, naphthoyl, furoyl, nicotinoyl, 4-carboxybutanoyl, oxalyl, ethoxalyl, cysteinyl, oxamoyl.

The term "sulfonyl derivative", as used herein, is defined as including a group of the formula —$SO_2$—$R^{11}$, wherein $R^{11}$ is as defined above except for "sulfonyl derivative". Non-limiting examples are alkylsulfonyl, alkenylsulfonyl, alkynylsulfonyl and arylsulfonyl.

The term "sulfinyl derivative", as used herein, is defined as including a group of the formula —SO—$R^{11}$, wherein $R^{11}$ is as defined above except for "sulfinyl derivative". Non-limiting examples are alkylsulfinyl, alkenylsulfinyl, alkynylsulfinyl and arylsulfinyl.

The term "alkyl", as used herein, is defined as including saturated, monovalent hydrocarbon radicals having straight, branched or cyclic moieties or combinations thereof and generally containing 1-20 carbon atoms, most often 1 to 12 carbon atoms, preferably 1-7 carbon atoms for non-cyclic alkyl and 3-7 carbon atoms for cycloalkyl (in these two preferred cases, unless otherwise specified, "lower alkyl"), each optionally substituted by, preferably 1 to 5, substituents independently selected from the group consisting of halogen, hydroxy, thiol, amino, nitro, cyano, thiocyanato, acyl, acyloxy, sulfonyl derivative, sulfinyl derivative, alkylamino, carboxy, ester, ether, amido, azido, cycloalkyl, sulfonic acid, sulfonamide, thio derivative, alkylthio, oxyester, oxyamido, heterocycle, vinyl, alkoxy (preferably C1-5), aryloxy (preferably C6-10) and aryl (preferably C6-10).

Preferred are alkyl groups containing 1 to 7 carbon atoms, each optionally substituted by one or more substituents selected from hydroxy, halogen, cyano, thiocyanato, alkoxy, azido, alkylthio, cyclopropyl, acyl and phenyl. Most preferred are C1-4 alkyl and C3-7 cycloalkyl, each optionally substituted by one or more hydroxy, halogen, lower alkyl or/and azido.

Most preferred alkyl groups are hydroxymethyl, propyl, butyl, 2,2,2-trifluoroethyl, 2-bromo-2,2-difluoroethyl, 2-chloro-2,2-difluoroethyl, 3,3,3-trifluoropropyl, cyclopropylmethyl, iodomethyl, azidomethyl, 2,2-difluoropropyl, 2-iodo-2,2-difluoroethyl.

The term "lower alkyl", as used herein, and unless otherwise specified, refers to $C_1$ to $C_7$ saturated straight, branched or cyclic hydrocarbon. Non limiting examples are methyl, ethyl, propyl, isopropyl, butyl, tertiobutyl, pentyl, cyclopropyl, cyclopentyl, isopentyl, neopentyl, hexyl, isohexyl, cyclohexyl, 3-methypentyl, 2,2-dimethylbutyl, optionally substituted with any suitable group, including but not limited to one or more moieties selected from groups as described above for the alkyl groups. Preferably, lower alkyl is methyl.

The term "alkenyl", as used herein, is defined as including both branched and unbranched, unsaturated hydrocarbon radicals having at least one double bond, and being optionally substituted by at least one substituent selected from the group consisting of halogen, hydroxy, thiol, amino, thiocyanato, azido, alkylthio, cycloalkyl, acyl, nitro, cyano, aryl and heterocycle.

Prefered alkenyl groups are C2-C12 alkenyls, especially C2-6 alkenyls, such as ethenyl (=vinyl), 1-methyl-1-ethenyl, 2,2-dimethyl-1-ethenyl, 1-propenyl, 2-propenyl (=allyl), 1-butenyl, 2-butenyl, 3-butenyl, 4-pentenyl, 1-methyl-4-pentenyl, 3-methyl-1-pentenyl, 1-hexenyl, 2-hexenyl and the like, optionally being substituted by one or more substituents selected from halogen, cyano, thiocyanato, azido, alkylthio, cycloalkyl, phenyl and acyl. Most prefered is vinyl, optionally substituted by one or more halogen or/and lower alkyl, and especially 2,2-difluorovinyl, 2,2-dibromovinyl and 2,2-dichlorovinyl.

The term "alkynyl" as used herein, is defined as including a monovalent branched or unbranched hydrocarbon radical containing at least one carbon-carbon triple bond, for example ethynyl, 2-propynyl (=propargyl), and the like, and being optionally substituted by at least one substituent selected from the group consisting of halogen, hydroxy, thiol, amino, nitro, cyano, aryl, heterocycle, thiocyanato, azido, alkylthio, alkyl and acyl.

Preferred alkynyl groups are C2-12 alkynyl, especially C2-6 alkynyl, optionally being substituted by one or more substituents selected from halogen, cyano, thiocyanato, azido, alkylthio, acyl, aryl such as phenyl and alkyl, preferably cycloalkyl.

Most preferred are ethynyl, propynyl and butynyl, optionally substituted by lower alkyl or/and halogen, and especially 1-propynyl, cyclopropylethynyl, 3-methyl-1-butynyl and 3,3,3-trifluoro-1-propynyl.

When present as bridging groups, alkyl, alkenyl and alkynyl represent straight- or branched chains, C1-12, preferably C1-4-alkylene or C2-12-, preferably C2-4-alkenylene or -alkynylene moieties respectively.

Groups where branched derivatives are conventionally qualified by prefixes such as "n", "sec", "iso" and the like (e.g. "n-propyl", "sec-butyl") are in the n-form unless otherwise stated.

The term "aryl", as used herein, is defined as including an organic radical derived from an aromatic hydrocarbon consisting of at least one ring, most often 1 to 3 rings and generally containing 6-30 carbon atoms by removal of one hydrogen, such as phenyl and naphthyl, each optionally substituted by one or more substituents independently selected from halogen, hydroxy, thiol, amino, nitro, cyano, acyl, acyloxy, sulfonyl, sulfinyl, alkylamino, carboxy, ester, ether, amido, azido, sulfonic acid, sulfonamide, alkylsulfonyl, alkylsulfinyl, C1-6-alkylthio, oxyester, oxyamido, aryl, C1-6-alkoxy, C6-10-aryloxy, C1-6-alkyl, C1-6-haloalkyl. Aryl radicals are preferably monocyclic or bicyclic containing 6-10 carbon atoms. Preferred aryl groups are phenyl and naphthyl each optionally substituted by one or more substituents independently selected from halogen, nitro, amino, azido, C1-6-alkoxy, C1-6-alkyl, C1-6-haloalkyl, sulfonyl and phenyl.

Preferred aryl is phenyl, optionally substituted by one or more halogen, lower alkyl, azido or nitro, such as 3-chlorophenyl and 3-azidophenyl.

The term "halogen", as used herein, includes an atom of Cl, Br, F, I.

The term "hydroxy", as used herein, represents a group of the formula —OH.

The term "thiol", as used herein, represents a group of the formula —SH.

The term "cyano", as used herein, represents a group of the formula —CN.

The term "nitro", as used herein, represents a group of the formula —$NO_2$.

The term "nitrooxy", as used herein, represents a group of the formula —$ONO_2$.

The term "amino", as used herein, represents a group of the formula —$NH_2$.

The term "azido", as used herein, represents a group of the formula —N₃.

The term "carboxy", as used herein, represents a group of the formula —COOH.

The term "sulfonic acid", as used herein, represents a group of the formula —SO₃H.

The term "sulfonamide", as used herein, represents a group of the formula —SO₂NH₂.

The term "ester", as used herein, is defined as including a group of formula —COO—$R^{11}$ wherein $R^{11}$ is as defined above except oxy derivative, thio derivative or amino derivative. Preferred are esters of formula —COOR$^{11}$ wherein $R^{11}$ is selected from C1-12 alkyl, C2-12 alkenyl, C2-12 alkynyl and aryl. Most preferred are esters where $R^{11}$ is a lower alkyl, especially methyl.

The term "ether" is defined as including a group selected from C1-50-straight or branched alkyl, or C2-50-straight or branched alkenyl or alkynyl groups or a combination of the same, interrupted by one or more oxygen atoms.

The term "amido" is defined as including a group of formula —CONH₂ or —CONHR$^{11}$ or —CONR$^{11}$R$^{12}$ wherein $R^{11}$ and $R^{12}$ are as defined above.

The term "heterocycle", as used herein, is defined as including an aromatic or non aromatic cyclic alkyl, alkenyl, or alkynyl moiety as defined above, having at least one O, S and/or N atom interrupting the carbocyclic ring structure and optionally, one of the carbon of the carbocyclic ring structure may be replaced by a carbonyl, and optionally being substituted with any suitable group, including but not limited to one or more moieties selected from lower alkyl, or other groups as described above for the alkyl groups. Non-limiting examples of heterocycles are pyridyl, furyl, pyrrolyl, thienyl, isothiazolyl, triazolyl, imidazolyl, benzimidazolyl, tetrazolyl, quinazolinyl, quinolizinyl, naphthyridinyl, pyridazinyl, pyrimidinyl, pyrazinyl, quinolyl, isoquinolyl, isobenzofuranyl, benzothienyl, pyrazolyl, indolyl, indolizinyl, purinyl, isoindolyl, carbazolyl, thiazolyl, 1,2,4-thiadiazolyl, thiomorpholinyl, thieno(2,3-b)furanyl, furopyranyl, benzofuranyl, benzoxepinyl, isooxazolyl, oxazolyl, thianthrenyl, benzothiazolyl, or benzoxazolyl, cinnolinyl, phthalazinyl, quinoxalinyl, 1-oxidopyridyl, phenanthridinyl, acridinyl, perimidinyl, phenanthrolinyl, phenothiazinyl, furazanyl, benzodioxolyl, isochromanyl, indolinyl, xanthenyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, tetrahydrofuranyl, tetrahydropyranyl, piperidinyl, piperidyl, piperazinyl, imidazolidinyl, morpholino, morpholinyl, 1-oxaspiro(4.5)dec-2-yl, pyrrolidinyl, 2-oxo-pyrrolidinyl, sugar moieties (i. e. glucose, pentose, hexose, ribose, fructose, which may also be substituted) optionally substituted by alkyl or as described above for the alkyl groups. The term "heterocycle" also includes bicyclic, tricyclic and tetracyclic, spiro groups in which any of the above heterocyclic rings is fused to one or two rings independently selected from an aryl ring, a cyclohexane ring, a cyclohexene ring, a cyclopentane ring, a cyclopentene ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1)heptanyl, 8-azabicyclo(3.2.1)octanyl.

The heterocycle is preferably selected from triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl and piperazinyl, each optionally substituted by one or more substituents selected from halogen, alkyl, substituted alkyl, alkoxy, nitro, amino, acyl and phenyl.

More preferably the heterocycle is selected from tetrazolyl, pyrrolidinyl, pyridyl, furyl, pyrrolyl, thiazolyl and thienyl, each optionally substituted by one or more substituents selected from halogen, alkyl, halogen substituted alkyl, acyl, alkoxy, nitro, amino and phenyl, and especially from 2- and 3-thienyl, optionally substituted by one or more halogen, acyl such as formyl, cyano and/or lower alkyl, such as methyl.

In the above definitions it is to be understood that when a substituent such as $R^1$, $R^2$, $R^3$, $R^4$, $R^5$, $R^7$, $R^8$, $R^9$, $R^{10}$ is attached to the rest of the molecule via a heteroatom or a carbonyl, a straight- or branched chain, C1-12-, preferably C1-4-alkylene or C2-12, preferably C2-4-alkenylene or -alkynylene bridge may optionally be interposed between the heteroatom or the carbonyl and the point of attachment to the rest of the molecule.

The term "R substituent" refers to $R^1$, $R^2$, $R^3$, $R^4$ or $R^5$, independently.

According to a preferred embodiment, a compound of formula I is as defined above wherein n represents 0. The compound is a 6-ring structure (2-thioxo- or 2-oxo-piperidinyl derivative) wherein $R^1$ is not existent since n=0, and is depicted by the formula (I-A).

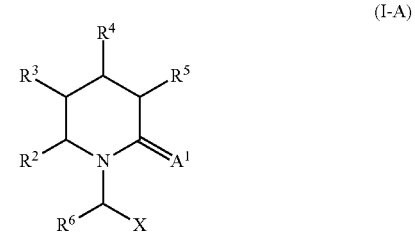

(I-A)

According to a following embodiment, the compound of formula I is as defined above wherein n represents 1. The compound is a 7-ring structure (2-thioxo- or 2-oxo-azepanyl derivative) wherein $R^1$ is existent since n=1 and depicted by the formula (I-B).

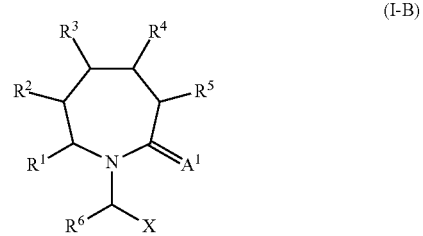

(I-B)

According to a more preferred embodiment, said compound is as defined above wherein n=0, $R^3$ and/or $R^4$ are different from hydrogen and $R^2$ and $R^5$ represent hydrogen.

According to another more preferred embodiment, said compound is as defined above wherein n=1, $R^2$, $R^3$ and/or $R^4$ are different from hydrogen and wherein $R^1$ and $R^5$ represent hydrogen.

According to a yet more preferred embodiment, said compound is as defined above wherein only one R substituent chosen from $R^3$ or $R^4$ when n=0 or from $R^2$, $R^3$ or $R^4$ when n=1, is different from hydrogen and the remaining R substituent(s) is/are hydrogen. We hereby refer to a mono-substituted 2-thioxo- or 2-oxo-piperidinyl or 2-thioxo- or 2-oxo-azepanyl derivatives.

According to another preferred embodiment, compounds of formula I are as defined above wherein $A^1$ represents an oxygen atom. We hereby refer to 2-oxo-piperidinyl or 2-oxo-azepanyl derivatives.

According to another preferred embodiment, compounds of formula I are as defined above wherein X is $CONR^7R^8$, especially $CONH_2$. We hereby refer to amido derivatives of 2-oxo (or thioxo)-piperidinyl or 2-oxo (or thioxo) -azepanyl.

According to another preferred embodiment, compounds of formula I are as defined above wherein $R^6$ represents hydrogen, C1-4 alkyl, or a $CH_2$—$R^{6a}$ group wherein $R^{6a}$ represents a heterocycle. Most preferably $R^6$ is a C1-4 alkyl, especially ethyl. When $R^6$ is ethyl we refer to 2-(2-oxo (or thioxo)-1-piperidinyl)butanamide or 2-(2-oxo (or thioxo)-1-azepanyl)butanamide derivatives.

According to another preferred embodiment, compounds of formula I are as defined above wherein the carbon atom to which $R^6$ is attached is of the S configuration. In case where $R^6$ is ethyl, A is oxygen and X is $CONR^7R^8$ we refer then to (2S)-2-(2-oxo-1-piperidinyl)butanamide or (2S)-2-(2-oxo-1-azepanyl)butanamide derivatives.

According to a prefered embodiment, the compound is as defined above wherein $R^2$ when n=1, $R^3$ and $R^4$ are the same or different and each is independently hydrogen, halogen, nitro, nitrooxy, cyano, carboxy, amido, sulfonic acid, sulfonamide, alkyl, alkenyl, alkynyl, ester, ether, aryl, heterocycle, acyl derivative, sulfonyl derivative or sulfinyl derivative;

$R^1$ when existent, $R^2$ when n=0 and $R^5$ are hydrogen;

$R^6$ is hydrogen, alkyl, aryl or —$CH_2$—$R^{6a}$ wherein $R^{6a}$ is aryl, heterocycle, halogen, hydroxy, amino, nitro or cyano;

According to this preferred embodiment, the compound is generally such that when $R^6$ is benzyl, X is —$COOCH_3$ and n=1, $R^2$ is different from methyl when $R^3$ and $R^4$ are both hydrogen and $R^4$ is different from methyl when $R^2$ and $R^3$ are both hydrogen.

According to another preferred embodiment, the compound is as defined above wherein $R^2$ when n=1, $R^3$ and $R^4$ are the same or different and each is independently hydrogen; cyano; carboxy; amido;

C1-12 alkyl, each optionally substituted by one or more substituents selected from hydroxy, halogen, cyano, thiocyanato, alkoxy, azido, alkyltio, cycloalkyl, acyl, aryl and heterocycle;

C2-12 alkenyl, each optionally substituted by one or more substituents selected from halogen, cyano, thiocyanato, azido, alkylthio, alkyl, aryl and acyl;

C2-12 alkynyl, each optionally substituted by one or more substituents selected from halogen, cyano, thiocyanato, azido, alkylthio, alkyl, aryl and acyl; acyl derivative of formula —CO—$R^{11}$, wherein $R^{11}$ is selected from C1-12 alkyl, C2-12 alkenyl, C2-12 alkynyl, heterocycle and aryl;

ester of formula —CO—O—$R^{11}$ wherein $R^{11}$ is selected from C1-12 alkyl, C2-12 alkenyl, C2-12 alkynyl and aryl;

heterocycle selected from triazolyl, tetrazolyl, pyrrolidinyl, pyridyl, 1-oxidopyridyl, thiomorpholinyl, benzodioxolyl, furyl, oxazolyl, pyrimidinyl, pyrrolyl, thiadiazolyl, thiazolyl, thienyl and piperazinyl, each optionally substituted by one or more substituents selected from halogen, alkyl, substituted alkyl, alkoxy, nitro, amino, acyl and phenyl;

aryl, each optionally substituted by one or more substituents selected from C1-6 alkyl, C1-6 haloalkyl, C1-6 alkoxy, C1-6 alkylthio, amino, azido, sulfonyl, aryl and nitro.

According to another preferred embodiment, the compound is as defined above, wherein $R^2$ when n=1, $R^3$ and $R^4$ are the same or different and each is independently hydrogen;

C1-7 alkyl, each optionally substituted by one or more substituents selected from hydroxy, halogen, cyano, thiocyanato, alkoxy, azido, alkyltio, cyclopropyl, acyl and phenyl;

C2-6 alkenyl, each optionally substituted by one or more substituents selected from halogen, cyano, thiocyanato, azido, alkylthio, cycloalkyl, phenyl and acyl;

C2-6 alkynyl, each optionally substituted by one or more substituents selected from halogen, cyano, thiocyanato, azido, alkylthio, cycloalkyl, phenyl and acyl;

heterocycle selected from tetrazolyl, pyrrolidinyl, pyridyl, furyl, pyrrolyl, thiazolyl and thienyl, each optionally substituted by one or more substituents selected from halogen, alkyl, halogen substituted alkyl, acyl, alkoxy, nitro, amino and phenyl;

phenyl, each optionally substitued by one or more substituents selected from C1-6 alkyl, halogen substituted alkyl, halogen, alkoxy, amino, azido, sulfonyl, phenyl and nitro.

According to another preferred embodiment, the compound is as defined above wherein at least one of the R substituents chosen from the group $R^2$, $R^3$ and $R^4$ when n=1 or from the group $R^3$ and $R^4$ when n=0, represents independently C1-4-alkyl or C3-7-cycloalkyl, optionally substituted by one or more halogen, hydroxy, lower alkyl and/or azido.

According to another preferred embodiment, the compound is as defined above wherein at least one of the R substituents chosen from the group $R^2$, $R^3$ and $R^4$ when n=1 or from the group $R^3$ and $R^4$ when n=0, represents independently vinyl, optionally substituted by one or more halogen or/and lower alkyl.

According to another preferred embodiment, the compound is as defined above wherein at least one of the R substituents chosen from the group $R^2$, $R^3$ and $R^4$ when n=1 or from the group $R^3$ and $R^4$ when n=0, represents independently ethynyl, propynyl or butynyl, optionally substituted by one or more halogen and/or lower alkyl.

According to another preferred embodiment, the compound is as defined above wherein at least one of the R substituents chosen from the group $R^2$, $R^3$ and $R^4$ when n=1 or from the group $R^3$ and $R^4$ when n=0, represents independently phenyl, optionally substituted by one or more halogen, lower alkyl, azido and/or nitro.

According to another preferred embodiment, the compound is as defined above wherein at least one of the R substituents chosen from the group $R^2$, $R^3$ and $R^4$ when n=1 or from the group $R^3$ and $R^4$ when n=0, represents independently 2- or 3-thienyl, optionally substituted by one or more halogen, acyl, cyano or/and lower alkyl.

According to a particular preferred embodiment, the compound is as defined above wherein at least one of the R substituents chosen from the group $R^3$, $R^4$ and $R^2$ when n=1 or from the group $R^3$ and $R^4$ when n=0, is hydroxymethyl, propyl, butyl, 3,3,3-trifluoropropyl, 2,2,2-trifluoroethyl, cyclopropylmethyl, iodomethyl, azidomethyl, 2-thienyl, 3-thienyl, phenyl, 3-chlorophenyl, 3-azidophenyl, 2,2-difluorovinyl, 2,2-dibromovinyl, 2,2-dichlorovinyl, 2-ethynyl, 5-methyl-2-thienyl, 5-formyl-2-ethynyl, 5-cyano-2-thienyl, 3-bromo-2-thienyl, 4-methyl-2-thienyl, 3,3,3-trifluoro-1-propynyl, 1-propynyl, cyclopropylethynyl, 3-methyl-1-butynyl, 1-butynyl, 2,2-difluoropropyl, 2-chloro-2,2-difluoroethyl, 2-bromo-2,2-difluoroethyl and 2-iodo-2,2-difluoroethyl.

According to yet another preferred embodiment, the compound is as defined above wherein $R^1$, $R^2$, $R^4$ and $R^5$ are hydrogen.

According to even another preferred embodiment, the compound is as defined above wherein $R^1$, $R^2$, $R^3$ and $R^5$ are hydrogen.

According to even another preferred embodiment, the compound is as defined above wherein n=1 and $R^1$, $R^3$, $R^4$ and $R^5$ are hydrogen.

In all the above-mentioned scopes when the carbon atom to which $R^6$ is attached is asymmetric it is preferably in the "S"-configuration.

Representative compounds useful in the methods and compositions of this invention as defined above are selected from the group consisting of
2-[5-(hydroxymethyl)-2-oxo-1-piperidinyl]butanamide,
2-(2-oxo-5-propyl-1-piperidinyl)butanamide,
2-[2-oxo-5-(3,3,3-trifluoropropyl)-1-piperidinyl]butanamide,
2-[5-(cyclopropylmethyl)-2-oxo-1-piperidinyl]butanamide,
2-[5-(iodomethyl)-2-oxo-1-piperidinyl]butanamide,
2-[5-(azidomethyl)-2-oxo-1-piperidinyl]butanamide,
2-(2-oxo-5-phenyl-1-piperidinyl)butanamide,
2-[2-oxo-5-(2-thienyl)-1-piperidinyl]butanamide,
2-[2-oxo-5-(3-thienyl)-1-piperidinyl]butanamide,
2-[5-(3-chlorophenyl)-2-oxo-1-piperidinyl]butanamide,
2-[5-(3-azidophenyl)-2-oxo-1-piperidinyl]butanamide,
2-[5-(2,2-difluorovinyl)-2-oxo-1-piperidinyl]butanamide,
2-[5-(2,2-dibromovinyl)-2-oxo-1-piperidinyl]butanamide,
2-[5-(2,2-dichlorovinyl)-2-oxo-1-piperidinyl]butanamide,
2-(5-ethynyl-2-oxo-1-piperidinyl)butanamide,
2[5-(5-methyl-2-thienyl)-2-oxo-1-piperidinyl]butanamide,
2-[5-(5-formyl-2-thienyl)-2-oxo-1-piperidinyl]butanamide,
2-[5-(5-cyano-2-thienyl)-2-oxo-1-piperidinyl]butanamide,
2-[5-(3-bromo-2-thienyl)-2-oxo-1-piperidinyl]butanamide,
2-[5-(4-methyl-2-thienyl)-2-oxo-1-piperidinyl]butanamide,
2-[2-oxo-5-(3,3,3-trifluoro-1-propynyl)-1-piperidinyl]butanamide,
2-[2-oxo-5-(1-propynyl)-1-piperidinyl]butanamide,
2-[5-(cyclopropylethynyl)-2-oxo-1-piperidinyl]butanamide,
2-[5-(3-methyl-1-butynyl)-2-oxo-1-piperidinyl]butanamide,
2-[5-(1-butynyl)-2-oxo-1-piperidinyl]butanamide,
2-[5-(2,2-difluoropropyl)-2-oxo-1-piperidinyl]butanamide,
2-[5-(2-chloro-2,2-difluoroethyl)-2-oxo-1-piperidinyl]butanamide,
2-[5-(2-bromo-2,2-difluoroethyl)-2-oxo-1-piperidinyl]butanamide,
2-[4-(hydroxymethyl)-2-oxo-1-piperidinyl]butanamide,
2-(2-oxo-4-propyl-1-piperidinyl)butanamide,
2-[2-oxo-4-(3,3,3trifluoropropyl)-1-piperidinyl]butanamide,
2-[4-(cyclopropylrnethyl)-2-oxo-1-piperidinyl]butanamide,
2-[4-(iodomethyl)-2-oxo-1-piperidinyl]butanamide,
2-[4-(azidomethyl)-2-oxo-1-piperidinyl]butanamide,
2-(2-oxo-4-phenyl-1-piperidinyl)butanamide,
2-[2-oxo-4-(2-thienyl)-1-piperidinyl]butanamide,
2-[2-oxo-4-(3-thienyl)-1-piperidinyl]butanamide,
2-[4-(3-chlorophenyl)-2-oxo-1-piperidinyl]butanamide,
2-[4-(3-azidophenyl)-2-oxo-1-piperidinyl]butanamide,
2-[4-(2,2-difluorovinyl)-2-oxo-1-piperidinyl]butanamide,
2-[4-(2,2-dibromovinyl)-2-oxo-1-piperidinyl]butanamide,
2-[4-(2,2-dichlorovinyl)-2-oxo-1-piperidinyl]butanamide,
2-(4-ethynyl-2-oxo-1-piperidinyl)butanamide,
2-[4-(5-methyl-2-thienyl)-2-oxo-1-piperidinyl]butanamide,
2-[4-(5-formyl-2-thienyl)-2-oxo-1-piperidinyl]butanamide,
2-[4-(5-cyano-2-thienyl)-2-oxo-1-piperidinyl]butanamide,
2-[4-(3-bromo-2-thienyl)-2-oxo-1-piperidinyl]butanamide,
2-[4-(4-methyl-2-thienyl)-2-oxo-1-piperidinyl]butanamide,
2-[2-oxo-4-(3,3,3-trifluoro-1-propynyl)-1-piperidinyl]butanamide,
2-[2-oxo-4-(1-propynyl)-1-piperidinyl]butanamide,
2-[4-(cyclopropylethynyl)-2-oxo-1-piperidinyl]butanamide,
2-[4-(3-methyl-1-butynyl)-2-oxo-1-piperidinyl]butanamide,
2-[4-(1-butynyl)-2-oxo-1-piperidinyl]butanamide,
2-[4-(2,2-difluoropropyl)-2-oxo-1-piperidinyl]butanamide,
2-[4-(2-chloro-2,2-difluoroethyl)-2-oxo-1-piperidinyl]butanamide,
2-[4-(2-bromo-2,2-difluoroethyl)-2-oxo-1-piperidinyl]butanamide,
2[4-(2,2,2-trifluoroethyl)-2-oxo-1-piperidinyl]butanamide,
2-[5-(hydroxymethyl)-2-oxo-1-azepanyl]butanamide,
2-(2-oxo-5-propyl-1-azepanyl)butanamide,
2-[2-oxo-5-(3,3,3-trifluoropropyl)-1-azepanyl]butanamide,
2-[5-(cyclopropylmethyl)-2-oxo-1-azepanyl]butanamide,
2-[5-(iodomethyl)-2-oxo-1-azepanyl]butanamide,
2-[5-(azidomethyl)-2-oxo-1-azepanyl]butanamide,
2-(2-oxo-5-phenyl-1-azepanyl)butanamide,
2-[2-oxo-5-(2-thienyl)-1-azepanyl]butanamide,
2-[2-oxo-5-(3-thienyl)-1-azepanyl]butanamide,
2-[5-(3-chlorophenyl)-2-oxo-1-azepanyl]butanamide,
2-[5-(3-azidophenyl)-2-oxo-1-azepanyl]butanamide,
2-[5-(2,2-difluorovinyl)-2-oxo-1-azepanyl]butanamide,
2-[5-(2,2-dibromovinyl)-2-oxo-1-azepanyl]butanamide,
2-[5-(2,2-dichlorovinyl)-2-oxo-1-azepanyl]butanamide,
2-(5-ethynyl-2-oxo-1-azepanyl)butanamide,
2-[5-(5-methyl-2-thienyl)-2-oxo-1-azepanyl]butanamide,
2-[5-(5-formyl-2-thienyl)-2-oxo-1-azepanyl]butanamide,
2-[5-(5-cyano-2-thienyl)-2-oxo-1-azepanyl]butanamide,
2-[5-(3-bromo-2-thienyl)-2-oxo-1-azepanyl]butanamide,
2-[5-(4-methyl-2-thienyl)-2-oxo-1-azepanyl]butanamide,
2-[2-oxo-5-(3,3,3-trifluoro-1-propynyl)-1-azepanyl]butanamide,
2-[2-oxo-5-(1-propynyl)-1-azepanyl]butanamide,
2-[5-(cyclopropylethynyl)-2-oxo-1-azepanyl]butanamide,
2-[5-(3-methyl-1-butynyl)-2-oxo-1-azepanyl]butanamide,
2-[5-(1-butynyl)-2-oxo-1-azepanyl]butanamide,
2-[5-(2,2-difluoropropyl)-2-oxo-1-azepanyl]butanamide,
2-[5-(2-chloro-2,2-difluoroethyl)-2-oxo-1-azepanyl]butanamide,
2-[5-(2-bromo-2,2-difluoroethyl)-2-oxo-1-azepanyl]butanamide,
2-[5-(2,2,2-trifluoroethyl)-2-oxo-1-azepanyl]butanamide,
2-[6-(hydroxymethyl)-2-oxo-1-azepanyl]butanamide,
2-(2-oxo-6-propyl-1-azepanyl)butanamide,
2-[2-oxo-6-(3,3,3-trifluoropropyl)-1-azepanyl]butanamide,
2-[6-(cyclopropylmethyl)-2-oxo-1-azepanyl]butanamide,
2-[6-(iodomethyl)-2-oxo-1-azepanyl]butanamide,
2-[6-(azidomethyl)-2-oxo-1-azepanyl]butanamide,
2-(2-oxo-6-phenyl-1-azepanyl)butanamide,
2-[2-oxo-6-(2-thienyl)-1-azepanyl]butanamide,
2-[2-oxo-6-(3-thienyl)-1-azepanyl]butanamide,
2-[6-(3-chlorophenyl)-2-oxo-1-azepanyl]butanamide,
2-[6-(3-azidophenyl)-2-oxo-1-azepanyl]butanamide,
2-[6-(2,2-difluorovinyl)-2-oxo-1-azepanyl]butanamide,
2-[6-(2,2-dibromovinyl)-2-oxo-1-azepanyl]butanamide,
2-[6-(2,2-dichlorovinyl)-2-oxo-1-azepanyl]butanamide,
2-(6-ethynyl-2-oxo-1-azepanyl)butanamide,
2-[6-(5-methyl-2-thienyl)-2-oxo-1-azepanyl]butanamide,
2-[6-(5-formyl-2-thienyl)-2-oxo-1-azepanyl]butanamide,
2-[6-(5-cyano-2-thienyl)-2-oxo-1-azepanyl]butanamide,
2-[6-(3-bromo-2-thienyl)-2-oxo-1-azepanyl]butanamide,
2-[6-(4-methyl-2-thienyl)-2-oxo-1-azepanyl]butanamide,
2-[2-oxo-6-(3,3,3-trifluoro-1-propynyl)-1-azepanyl]butanamide,
2-[2-oxo-6-(1-propynyl)-1-azepanyl]butanamide,
2-[6-(cyclopropylethynyl)-2-oxo-1-azepanyl]butanamide,
2-[6-(3-methyl-1-butynyl)-2-oxo-1-azepanyl]butanamide,
2-[6-(1-butynyl)-2-oxo-1-azepanyl]butanamide,
2-[6-(2,2-difluoropropyl)-2-oxo-1-azepanyl]butanamide,
2-[6-(2-chloro-2,2-difluoroethyl)-2-oxo-1-azepanyl]butanamide, 2-[6-(2-bromo-2,2-difluoroethyl)-2-oxo-1-azepanyl]butanamide,
2-[6-(2,2,2-trifluoroethyl)-2-oxo-1-azepanyl]butanamide,
2-[4-(hydroxymethyl)-2-oxo-1-azepanyl]butanamide,
2-(2-oxo-4-propyl-1-azepanyl)butanamide,
2-[2-oxo-4-(3,3,3-trifluoropropyl)-1-azepanyl]butanamide,
2-[4-(cyclopropylmethyl)-2-oxo-1-azepanyl]butanamide,
2-[4-(iodomethyl)-2-oxo-1-azepanyl]butanamide,
2-[4-(azidomethyl)-2-oxo-1-azepanyl]butanamide,
2-(2-oxo-4-phenyl-1-azepanyl)butanamide,
2-[2-oxo-4-(2-thienyl)-1-azepanyl]butanamide,
2-[2-oxo-4-(3-thienyl)-1-azepanyl]butanamide,
2-[4-(3-chlorophenyl)-2-oxo-1-azepanyl]butanamide,
2-[4-(3-azidophenyl)-2-oxo-1-azepanyl]butanamide,
2-[4-(2,2-difluorovinyl)-2-oxo-1-azepanyl]butanamide,
2-[4-(2,2-dibromovinyl)-2-oxo-1-azepanyl]butanamide,
2-[4-(2,2-dichlorovinyl)-2-oxo-1-azepanyl]butanamide,
2-(4-ethynyl-2-oxo-1-azepanyl)butanamide,
2-[4-(5-methyl-2-thienyl)-2-oxo-1-azepanyl]butanamide,
2-[4-(5-formyl-2-thienyl)-2-oxo-1-azepanyl]butanamide,
2-[4-(5-cyano-2-thienyl)-2-oxo-1-azepanyl]butanamide,
2-[4-(3-bromo-2-thienyl)-2-oxo-1-azepanyl]butanamide,
2-[4-(4-methyl-2-thienyl)-2-oxo-1-azepanyl]butanamide,
2-[2-oxo-4-(3,3,3-trifluoro-1-propynyl)-1-azepanyl]butanamide,
2-[2-oxo-4-(1-propynyl)-1-azepanyl]butanamide,
2-[4-(cyclopropylethynyl)-2-oxo-1-azepanyl]butanamide,
2-[4-(3-methyl-1-butynyl)-2-oxo-1-azepanyl]butanamide,
2-[4-(1-butynyl)-2-oxo-1-azepanyl]butanamide,
2-[4-(2,2-difluoropropyl)-2-oxo-1-azepanyl]butanamide,
2-[4-(2-chloro-2,2-difluoroethyl)-2-oxo-1-azepanyl]butanamide,
2-[4-(2-bromo-2,2-difluoroethyl)-2-oxo-1-azepanyl]butanamide,
2-[4-(2,2,2-trifluoroethyl)-2-oxo-1-azepanyl]butanamide.

In some embodiments, compounds useful in the methods and compositions of this invention are selected from the group consisting of:
(2S)-2-[5-(iodomethyl)-2-oxo-1-piperidinyl]butanamide,
(2S)-2-[5-(azidomethyl)-2-oxo-1-piperidinyl]butanamide,
2-(2-oxo-5-phenyl-1-piperidinyl)butanamide,
(2S)-2-[4-(iodomethyl)-2-oxo-1-piperidinyl]butanamide,
2-[5-(iodomethyl)-2-oxo-1-azepanyl]butanamide.

iii) International Patent Application WO 2004/087658:

A compound having the formula I or a pharmaceutically acceptable salt thereof or stereoisomeric forms thereof,

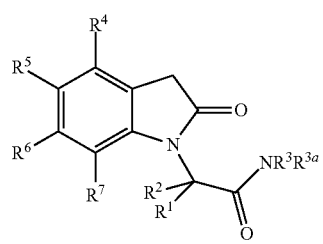

(I)

wherein
$R^1$ is hydrogen,
$R^2$ is hydrogen or C1-20-alkyl,
$R^3$ is hydrogen, C1-20-alkyl, C4-8-cycloalkyl, C5-8-cycloalkenyl, aryl, aromatic or non aromatic heterocycle, C1-20-alkoxy, or a group of formula —W—$R^8$, $R^{3a}$ is hydrogen, C1-20-alkyl or a group of formula:

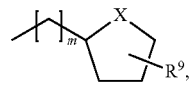

or $NR^3R^{3a}$ is a group of formula

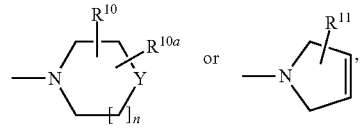

$R^4$ is hydrogen,
$R^5$ is hydrogen; nitro; halogen; azido; cyano; —S—C1-4-alkyl; —SO—C1-4-alkyl; —SO$_2$—C1-4-alkyl; —SONH$_2$; C1-20-alkyl unsubstituted or substituted by halogen; or C1-20-alkoxy unsubstituted or substituted by halogen,
$R^6$ is hydrogen, C1-20-alkyl or halogen,
$R^7$ is hydrogen, C1-20-alkyl or halogen,
W is C1-12-alkylene, —NH— or —NHC(=O)—,
X is O, S or NH,
Y is O, S, —CR$^{12}$R$^{13}$—, —NR$^{14}$— or —C(=O)—,
$R^8$ is aryl or heterocycle,
$R^9$, $R^{10}$, $R^{10a}$ and $R^{11}$ are independently selected from hydrogen, C1-4-alkyl, halogen, hydroxy or methoxycarbonyl,
or $R^{10}$ and $R^{10a}$ together form a C3-6-alkylene,
$R^{12}$ is hydrogen, C1-4-alkyl, halogen or hydroxy,
$R^{13}$ is hydrogen,
or CR$^{12}$R$^{13}$ is dioxolanyl,
$R^{14}$ is aryl, heterocycle or a group of formula —V—$R^{15}$,
V is $C_{1-12}$-alkylene,
$R^{15}$ is aryl or heterocycle,
m is 1 to 4,
n is 0 or 1,
and at least one of $R^5$, $R^6$ or $R^7$ is different from hydrogen when $R^2$ is hydrogen, $R^3$ is H or 2,6-diisopropylphenyl, and $R^{3a}$ is H.

In another aspect, the compound has the formula I or a pharmaceutically acceptable salt thereof or stereoisomeric forms thereof,

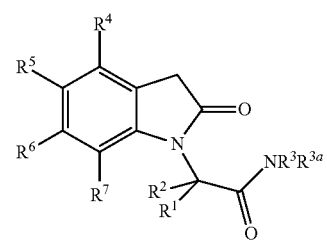

(I)

wherein
$R^1$ is hydrogen,
$R^2$ is hydrogen or C1-20-alkyl,
$R^3$ is hydrogen, C1-20-alkyl, C4-8-cycloalkyl, C5-8-cycloalkenyl, aryl, aromatic or non aromatic heterocycle, C1-20-alkoxy, or a group of formula —W—$R^8$, $R^{3a}$ is hydrogen, C1-20-alkyl or a group of formula:

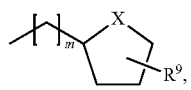

or $NR^3R^{3a}$ is a group of formula

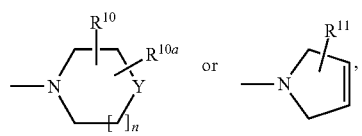

$R^4$ is hydrogen,
$R^5$ is hydrogen; nitro; halogen; C1-20-alkyl unsubstituted or substituted by halogen; or C1-20-alkoxy unsubstituted or substituted by halogen,
$R^6$ is hydrogen, C1-20-alkyl or halogen,
$R^7$ is hydrogen, C1-20-alkyl or halogen,
W is C1-12-alkylene, —NH— or —NHC(=O)—,
X is O, S or NH,
Y is O, S, —$CR^{12}R^{13}$—, —$NR^{14}$— or —C(=O)—,
$R^8$ is aryl or heterocycle,
$R^9$, $R^{10}$, $R^{10a}$ and $R^{11}$ are independently selected from hydrogen, C1-4-alkyl, halogen, hydroxy or methoxycarbonyl,
or $R^{10}$ and $R^{10a}$ together form a C3-6-alkylene,
$R^{12}$ is hydrogen, C1-4-alkyl, halogen or hydroxy,
$R^{13}$ is hydrogen,
or $CR^{12}R^{13}$ is dioxolanyl,
$R^{14}$ is aryl, heterocycle or a group of formula —V—$R^{15}$,
V is C1-12-alkylene,
$R^{15}$ is aryl or heterocycle,
m is 1 to 4,
n is 0 or 1,
and at least one of $R^5$, $R^6$ or $R^7$ is different from hydrogen when $R^2$ is hydrogen, $R^3$ is H or 2,6-diisopropylphenyl, and $R^{3a}$ is H.

The term "alkyl", as used herein, is defined as including saturated, monovalent hydrocarbon radicals having straight, branched or cyclic moieties or combinations thereof and containing 1-20 carbon atoms, preferably 1-6 carbon atoms and more preferably 1-4 carbon atoms for non-cyclic alkyl and 3-8 carbon atoms for cycloalkyl. Alliyl moieties may optionally be substituted by 1 to 5 substituents independently selected from halogen, hydroxy, alkoxy, alkoxycarbonyl, ester or alkylamino. Preferred alkyl groups are methyl, ethyl, n-propyl, isopropyl, trifluoromethyl, n-butyl, 2-fluoroethyl, 3-hydroxypropyl, 3-hydroxy-2,2-dimethylpropyl, 1-(hydroxymethyl)propyl, 3,3,3-trifluoro-2-hydroxypropyl, 3-ethoxypropyl, 2-ethoxy-2-oxoethyl and 3-(dimethylamino)propyl.

The term "cycloalkyl", as used herein, refers to a monovalent group of 3 to 18 carbon atoms, preferably 4-8 carbon atoms, derived from a saturated cyclic or polycyclic hydrocarbon which may be substituted by any suitable group including but not limited to one or more moieties selected from groups as described above for the alkyl groups. Preferred cycloalkyl group is cycloheptyl.

The term "alkylene", as used herein, represents a divalent alkyl group, having straight or branched moieties, containing 1-12 carbon atoms, preferably 1-6 carbon atoms, and being optionally substituted with any suitable group, including but not limited to one or more moieties selected from groups as described above for the alkyl groups. Preferred alkylene groups are methylene, ethylene, hydroxyethylene, trimethylene or propylene.

The term "cycloalkenyl", as used herein, is defined as a cyclic unsaturated hydrocarbon radical having at least one double bond, containing 4-20 carbon atoms, preferably 5-8 carbon atoms, and being optionally substituted with any suitable group, including but not limited to one or more moieties selected from groups as described above for the alkyl groups. Preferred cycloalkenyl group is 6-(hydroxymethyl)cyclohex-3-en-1-yl.

The term "aryl", as used herein, is defined as including an organic radical derived from an aromatic hydrocarbon consisting of 1-3 rings and containing 6-30 carbon atoms by removal of one hydrogen, such as phenyl and naphthyl each optionally substituted by 1 to 5 substituents independently selected from halogen, hydroxy, nitro, C1-6-alkyl, C1-6-alkoxy, C1-6-alkylsulfonyl, trifluoromethylthio or pyridinylalkyl. Aryl radicals are preferably phenyl radicals. Preferred aryl groups are phenyl, 3-hydroxyphenyl, 3-fluorophenyl, 3-methylphenyl, 4-methylphenyl, 4-hydroxyphenyl, 4-hydroxy-3-methoxyphenyl, 3-(2-pyridin-2-ylethyl)phenyl, 3,4-dimethylphenyl, 4-tert-butylphenyl, 4-methylsulfonylphenyl, 2-nitrophenyl, 2-chloro-6-fluorophenyl, 2-[(trifluoromethyl)thio]phenyl, 2-chlorophenyl or 4-bromophenyl.

The term "halogen", as used herein, includes an atom of Cl, Br, F, I.

The term "nitro", as used herein, represents a group of the formula —$NO_2$.

The term "hydroxy", as used herein, represents a group of the formula —OH.

The term "alkoxy", as used herein, represents a group of formula —$OR^b$ wherein $R^b$ is an alkyl group, as defined above.

The term "ester", as used herein, represents a group of formula, —$COOR^C$ wherein $R^c$ is an alkyl group or an aryl group, as defined above.

The term "alkoxycarbonyl", as used herein, represents a group of formula —$COOR^d$ wherein $R^d$ is an alkyl group, as defined above.

The term "amino", as used herein, represents a group of the formula —$NH_2$.

The term "alkylamino", as used herein, represents a group of formula —$NHR^e$ or —$NR^eR^f$ wherein $R^e$ and $R^f$ are alkyl group as defined above.

The term alkylsulfonyl, as used herein is defined as representing a group of formula —$SO_2$—$R^g$, wherein $R^g$ is C1-4-alkyl.

The term "heterocycle", as used herein is defined as including an aromatic or non aromatic cycloalkyl or cycloalkenyl moiety as defined above, having at least one O, S and/or N atom interrupting the carbocyclic ring structure and optionally, one of the carbon of the carbocyclic ring structure may be replaced by a carbonyl.

Non-limiting examples of aromatic heterocycles are pyrazolyl, furyl, imidazolyl, triazolyl, oxazolyl, pyridinyl, pyrrolyl, thienyl, isothiazolyl, benzimidazolyl, tetrazolyl, isooxazolyl, oxazolyl, thiazolyl, 1,2,4-thiadiazolyl, oxadiazole, pyridazinyl, pyrimidinyl, pyrazinyl, isoindolyl, triazolopyridinyl, imidazolopyridinyl, pyrrolopyrimidinyl, pyrazolopyrimidinyl, quinazolinyl, quinolizinyl, naphthyridinyl, quinolyl, isoquinolyl, isobenzofuranyl, benzothienyl, indolyl, indolizinyl, purinyl, carbazolyl, thieno (2,3-b), furanyl, thianthrenyl, benzothiazolyl, benzoxazolyl, cinnolinyl, quinoxalinyl, phenothiazinyl, isochromanyl and xanthenyl, optionally substituted by 1 to 5 substituents independently selected from halogen, hydroxy, thiol, amino, nitro, cyano, azido, C1-6-alkoxy, C1-6-alkylthio, C1-6-alkyl, C1-6-haloalkyl, formyl or ester. More preferred aromatic heterocycles are pyrazolyl, furyl, imidazolyl, triazolyl, oxazolyl and pyridinyl.

Non-limiting examples of non aromatic heterocycles are tetrahydrofuranyl, piperidinyl, piperidyl, piperazinyl, imidazolidinyl, morpholinyl, thiomorpholinyl, pyrrolidinyl, thiazolidinyl, indolinyl, tetrahydrobenzazocinyl, dihydroisochromenyl, tetrahydropyranyl, oxooctahydroquinolinyl, dioxolanyl, 1-oxaspiro(4.5)dec-2-yl, pyrrolidinyl, 2-oxopyrrolidinyl, 8-thiabicyclo[3.2.1]cyclooctanyl, 1,4-dithiepanyl, tetrahydro-2H-thiopyranyl, azepanyl and azocanyl, optionally substituted by 1 to 5 substituents independently selected from halogen, hydroxy, thiol, amino, nitro, cyano, azido, C1-6-alkoxy, C1-6-alkylthio, C1-6-alkyl, C1-6-haloalkyl, formyl or ester. More preferred non aromatic heterocycles are tetrahydrofuranyl, piperidinyl, piperidyl, piperazinyl, imidazolidinyl, morpholinyl, thiomorpholinyl, pyrrolidinyl, thiazolidinyl, indolinyl, tetrahydro-1-benzazocin-1 (2H)-yl, 3,4-dihydro-1H-isochromen-1-yl, tetrahydropyranyl, oxooctahydroquinolinyl and dioxolanyl. The term "heterocycle" also includes bicyclic, tricyclic and tetracyclic, Spiro groups in which any of the above heterocyclic rings is fused to one or two rings independently selected from an aryl ring, a cycloalkyl ring, a cycloalkenyl ring or another monocyclic heterocyclic ring or where a monocyclic heterocyclic group is bridged by an alkylene group, such as quinuclidinyl, 7-azabicyclo(2.2.1)heptanyl, 7-oxabicyclo(2.2.1)heptanyl and 8-azabicyclo(3.2.1)octanyl.

The term "pyridinylalkyl", as used herein, represents a group of formula —$R^h$-pyridinyl in which $R^h$ is C1-4-alkylene.

The term "azido" as used herein, represents a group of the formula —$N_3$.

The term "cyano" as used herein, represents a group of the formula —CN.

Generally, $R^2$ is hydrogen or C1-4-alkyl.

Preferably, $R^2$ is hydrogen, methyl or ethyl. More preferably, $R^2$ is hydrogen or methyl.

Generally, $R^3$ is hydrogen; C1-6-alkyl unsubstituted or substituted by 1 to 5 substituents selected from halogen, hydroxy, alkoxy, alkoxycarbonyl or alkylamino; C5-7-cycloalkyl; (hydroxymethyl)cyclohexenyl; phenyl unsubstituted or substituted by 1 to 5 substituents selected from halogen, C1-4-alkyl, hydroxy, methoxy, nitro, methylsulfonyl, trifluoromethylthio or pyridinylalkyl; pyridinyl unsubstituted or substituted by methoxy; triazolyl; C1-4-alkoxy; or a group of formula —W—$R^8$ wherein:

Generally, W is C1-4-alkylene unsubstituted or substituted by halogen, hydroxy, C1-4-alkyl or alkoxy; —NH—; or —NHC(=O)—; and $R^8$ is phenyl unsubstituted or substituted by 1 to 5 substituents selected from halogen, C1-4-alkyl, hydroxy, methoxy, nitro, methylsulfonyl or trifluoromethylthio; furyl unsubstituted or substituted by methyl; pyrazolyl; pyridinyl; morpholinyl; tetrahydrobenzazocinyl; piperidinyl unsubstituted or substituted by methyl; dihydroisochromenyl or dihydroimidazolyl.

Preferably, $R^3$ is hydrogen, n-butyl, cycloheptyl, 2-fluoroethyl, 3-hydroxypropyl, 3-hydroxy-2,2-dimethylpropyl, 1-(hydroxymethyl)propyl, 3,3,3-trifluoro-2-hydroxypropyl, 3-ethoxypropyl, 2-ethoxy-2-oxoethyl, 3-(dimethylamino) propyl, 6-(hydroxymethyl)cyclohex-3-en-1-yl, 3-hydroxyphenyl, 3-fluorophenyl, 3-(2-pyridin-2-ylethyl)phenyl, 3,4-dimethylphenyl, 4-tert-butylphenyl, benzyl, 4-hydroxy-3-methoxybenzyl, 4-methylsulfonylbenzyl, 2-nitrobenzyl, 2-chloro-6-fluorobenzyl, 2-[(trifluoromethyl)thio]benzyl, 2-hydroxy-2-phenylethyl, 2-(3,4-dimethoxyphenyl)ethyl, 2-(2-chlorophenyl)ethyl, 2-(4-methylphenyl)ethyl, (4-bromophenyl)amino, pyridin-3-yl, 6-methoxypyridin-3-yl, 4H-1,2,4-triazol-3-yl, pyridin-4-ylmethyl, (5-methyl-2-furyl)methyl, 3-(1H-pyrazol-1-yl)propyl, 2-morpholin-4-ylethyl, 2-((3,4,5,6-tetrahydro-1-benzazocin-1(2H)-yl)propyl, 2-(2-methylpiperidin-1-yl)ethyl, 3,4-dihydro-1H-isochromen-1-ylmethyl, methoxy, (4-pyridinylcarbonyl)amino or 4,5-dihydro-1H-imidazol-2-ylamino. More preferably, $R^3$ is hydrogen.

Generally, $R^{3a}$ is hydrogen, C1-4-alkyl or a group of formula

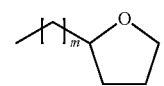

wherein m is 1 to 4.

Preferably, $R^{3a}$ is hydrogen, methyl or tetrahydrofuran-2-ylmethyl. More preferably, $R^{3a}$ is hydrogen.

In another embodiment, $NR^3R^{3a}$ is piperidinyl unsubstituted or substituted by hydroxy; thiomorpholinyl; thiazolidinyl unsubstituted or substituted by C1-4-alkoxycarbonyl; 2,5-dihydro-1H-pyrrol-1-yl; 1,4-dioxa-8-azaspiro[4.5]dec-8-yl; 4-oxooctahydro-1(2H)-quinolinyl; or a group of formula

wherein $R^{14}$ is pyridinyl; phenyl unsubstituted or substituted by halogen, hydroxy, C1-4-alkyl; or a group of formula —V—$R^{15}$ wherein V is unsubstituted C1-4-alkylene and $R^{15}$ is phenyl or morpholinyl.

In a preferred embodiment, $NR^3R^{3a}$ is 4-pyridin-2-ylpiperazin-1-yl, 4-(3-methylphenyl)piperazin-1-yl, 4-(4-hydroxyphenyl)piperazin-1-yl, 4-(2-phenylethyl)piperazin-1-yl, 4-(2-morpholin-4-ylethyl)piperazin-1-yl, 3-hydroxypiperidin-1-yl, thiomorpholin-4-yl, 4-methoxycarbonyl-1,3-thiazolidin-3-yl, 2,5-dihydro-1H-pyrrol-1-yl, 1,4-dioxa-8-azaspiro[4.5]dec-8-yl or 4-oxooctahydro-1(2H)-quinolinyl.

Generally, $R^5$ is hydrogen, nitro, halogen, C1-4-alkyl, unsubstituted or substituted by halogen, or C1-4-alkoxy unsubstituted or substituted by halogen.

Preferably, $R^5$ is hydrogen, methyl, ethyl, trifluoromethyl, trifluoromethoxy, n-propyl, isopropyl, nitro, or halogen. More preferably, $R^5$ is halogen or trifluoromethyl.

Generally, $R^6$ is hydrogen, C1-6-alkyl or halogen.

Preferably, $R^6$ is hydrogen, methyl or Cl. More preferably, $R^6$ is hydrogen.

Generally, $R^7$ is hydrogen, methyl or halogen.

Preferably, $R^7$ is hydrogen, methyl, Br, F or Cl. More preferably, $R^7$ is hydrogen, Br or F.

Combinations of one or more of these preferred compound groups are especially preferred.

In a preferred embodiment, the compound has the formula I or a pharmaceutically acceptable salt thereof or stereoisomeric forms thereof,

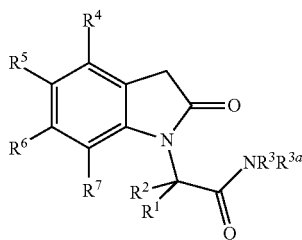

(I)

wherein R¹ is hydrogen,
R² is hydrogen or C1-4-alkyl,
R³ is hydrogen; C1-6-alkyl unsubstituted or substituted by 1 to 5 substituents selected from halogen, hydroxy, alkoxy, alkoxycarbonyl or alkylamino; C5-7-cycloalkyl; (hydroxymethyl)cyclohexenyl; phenyl unsubstituted or substituted by 1 to 5 substituents selected from halogen, C1-4-alkyl, hydroxy, methoxy, nitro, methylsulfonyl, trifluoromethylthio or pyridinylalkyl; pyridinyl unsubstituted or substituted by methoxy; triazolyl; C1-4-alkoxy; or a group of formula —W—R⁸,
R³ᵃ is hydrogen, C1-4-alkyl or a group of formula

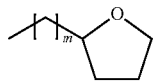

or NR³R³ᵃ is piperidinyl unsubstituted or substituted by hydroxy; thiomorpholinyl; thiazolidinyl unsubstituted or substituted by C1-4-alkoxycarbonyl; 2,5-dihydro-1H-pyrrol-1-yl; 1,4-dioxa-8-azaspiro[4.5]dec-8-yl; 4-oxooctahydro-1(2H)-quinolinyl; or a group of formula

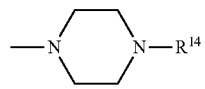

R⁴ is hydrogen,
R⁵ is hydrogen; nitro; halogen; C1-4-alkyl, unsubstituted or substituted by halogen; or C1-4-alkoxy unsubstituted or substituted by halogen,
R6 is hydrogen, C1-6-allyl or halogen,
R7 is hydrogen, methyl or halogen,
W is C1-4-alkylene unsubstituted or substituted by halogen, hydroxy, C1-4-alkyl or alkoxy; —NH—; or —NHC(=O)—,
R8 is phenyl unsubstituted or substituted by 1 to 5 substituents selected from halogen, C1-4-alkyl, hydroxy, methoxy, nitro, methylsulfonyl or trifluoromethylthio; furyl unsubstituted or substituted by methyl; pyrazolyl; pyridinyl; morpholinyl; tetrahydrobenzocinyl; piperidinyl unsubstituted or substituted by methyl; dihydroisochromenyl or dihydroimidazolyl,
R¹⁴ is pyridinyl; phenyl unsubstituted or substituted by halogen, hydroxy, C1-4-alkyl; or a group of formula —V—R¹⁵,
V is unsubstituted C1-4-alkylene,
R¹⁵ is phenyl or morpholinyl,
m is 1 to 4,
and at least one of R⁵, R⁶ or R⁷ is different from hydrogen when R² is hydrogen, R³ is H or 2,6-diisopropylphenyl, and R³ᵃ is H.

In a more preferred embodiment, the compound has the formula I or a pharmaceutically acceptable salt thereof or stereoisomeric forms thereof,

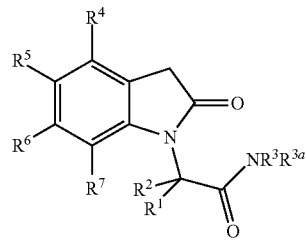

(I)

wherein
R¹ is hydrogen,
R² is hydrogen, methyl or ethyl,
R³ is hydrogen, n-butyl, cycloheptyl, 2-fluoroethyl, 3-hydroxypropyl, 3-hydroxy-2,2-dimethylpropyl, 1-(hydroxymethyl)propyl, 3,3,3-trifluoro-2-hydroxypropyl, 3-ethoxypropyl, 2-ethoxy-2-oxoethyl, 3-(dimethylamino)propyl, 6-(hydroxymethyl)cyclohex-3-en-1-yl, 3-hydroxyphenyl, 3-fluorophenyl, 3-(2-pyridin-2-ylethyl)phenyl, 3,4-dimethylphenyl, 4-tert-butylphenyl, benzyl, 4-hydroxy-3-methoxybenzyl, 4-methylsulfonylbenzyl, 2-nitrobenzyl, 2-chloro-6-fluorobenzyl, 2-[(trifluoromethyl)thio]benzyl, 2-hydroxy-2-phenylethyl, 2-(3,4-dimethoxyphenyl)ethyl, 2-(2-chlorophenyl)ethyl, 2-(4-methylphenyl)ethyl, (4-bromophenyl)amino, pyridin-3-yl, 6-methoxypyridin-3-yl, 4H-1,2,4-triazol-3-yl, pyridin-4-ylmethyl, (5-methyl-2-furyl)methyl, 3-(1H-pyrazol-1-yl)propyl, 2-morpholin-4-ylethyl, 2-((3,4,5,6-tetrahydro-1-benzazocin-1(2H)-yl)propyl, 2-(2-methylpiperidin-1-yl)ethyl, 3,4-dihydro-1H-isochromen-1-ylmethyl, methoxy, (4-pyridinylcarbonyl)amino or 4,5-dihydro-1H-imidazol-2-ylamino,
R³ᵃ is hydrogen, methyl or tetrahydrofuran-2-ylmethyl, or NR³R³ᵃ 4-pyridin-2-ylpiperazin-1-yl, 4-(3-methylphenyl)piperazin-1-yl, 4-(4-hydroxyphenyl)piperazin-1-yl, 4-(2-phenylethyl)piperazin-1-yl, 4-(2-morpholin-4-ylethyl)piperazin-1-yl, 3-hydroxypiperidin-1-yl, thiomorpholin-4-yl, 4-methoxycarbonyl-1,3-thiazolidin-3-yl, 2,5-dihydro-1H-pyrrol-1-yl, 1,4-dioxa-8-azaspiro[4.5]dec-8-yl or 4-oxooctahydro-1(2H)-quinolinyl,
R⁴ is hydrogen,
R5 is hydrogen, methyl, ethyl, trifluoromethyl, trifluoromethoxy, n-propyl, isopropyl, nitro or halogen,
R⁶ is hydrogen, methyl or Cl,
R⁷ is hydrogen, methyl, Br, F or Cl,
and at least one of R⁵, R⁶ or R⁷ is different from hydrogen when R² is hydrogen, R³ is H or 2,6-diisopropylphenyl, and R³ᵃ is H.
More preferably, R² is hydrogen or methyl, R³ is hydrogen, R³ᵃ is hydrogen, R⁵ is halogen or trifluoromethyl, R⁶ is hydrogen and R⁷ is hydrogen, Br or F.
In all the above-mentioned scopes, when R² is C1-20-alkyl, the carbon atom to which R² is attached is preferably in the"S"-configuration.
In some embodiments, compounds useful in the methods and compositions of this invention are selected from the group consisting of: 2-(5-iodo-2-oxo-2,3-dihydro-1H-indol-1-yl)acetamide; 2-(5-chloro-2-oxo-2,3-dihydro-1H-indol-1-yl)acetamide; 2-(5,7-dibromo-2-oxo-2,3-dthydro-1H-indol-1-yl)acetamide; 2-(5-nitro-2-oxo-2,3-dihydro-1H-indol-1-yl)acetamide; 2-(5-methyl-2-oxo-2,3-dihydro-1H-indol-1- yl) acetamide; 2-(5-chloro-2-oxo-2,3-dihydro-1H-indol-1-yl) propanamide; (2R)-2-(5-chloro-2-oxo-2,3-dihydro-1H-indol-1-yl) propanamide; (2S)-2-(5-chloro-2-oxo-2,3-dihydro-1H-indol-1-yl)propanamide; 2-[2-oxo-5-(trifluoromethoxy)-2,3-dihydro-1H-indol-1-yl]acetamide; 2-(5-isopropyl-2-oxo-2,3-dihydro-1H-indol-1-yl)acetamide; 2-(5-ethyl-2-oxo-2,3-dihydro-1H-indol-1-yl) acetamide; 2-(5-fluoro-2-oxo-2,3-dihydro-1H-indol-1-yl) acetamide; 2-(5,7-dimethyl-2-oxo-2,3-dihydro-1H-indol-1-yl) acetamide; 2-(5-bromo-2-oxo-2,3-dihydro-1H-indol-1-yl) acetamide; 2-(2-oxo-5-propyl-2,3-dihydro-1H-indol-1-yl) acetamide; 2-[2-oxo-5-(trifluoromethyl)-2,3-dihydro-1H-indol-1-yl]acetamide; 2-(5,6-dimethyl-2-oxo-2,3-dihydro-1H-indol-1-yl)acetamide; 2-(7-chloro-2-oxo-2,3-dihydro-1H-indol-1-yl)acetamide; 2-(6-chloro-2-oxo-2,3-dihydro-1H-indol-1-yl)acetamide; 2-(5-chloro-2-oxo-2,3-dihydro-1H-indol-1-yl)butanamide; (+)-2-(5-chloro-2-oxo-2,3-dihydro-1H-indol-1-yl)butanamide; (−)-2-(5-chloro-2-oxo-2,3-dihydro-1H-indol-1-yl)butanamide; 2-(5-methyl-2-oxo-2,3-dihydro-1H-indol-1-yl)propanamide; (+)-2-(5-methyl-2-oxo-2,3-dihydro-1H-indol-1-yl)propanamide; (−)-2-(5-methyl-2-oxo-2,3-dihydro-1H-indol-1-yl)propanamide; 2-(5-bromo-2-oxo-2,3-dihydro-1H-indol-1-yl)propanamide; (−)-2-(5-bromo-2-oxo-2,3-dihydro-1H-indol-1-yl)propanamide; (+)-2-(5-bromo-2-oxo-2,3-dihydro-1H-indol-1-yl)propanamide; 2-(5-chloro-7-fluoro-2-oxo-2,3-dihydro-1H-indol-1-yl)acetamide; 2-(5-chloro-2-oxo-2,3-dihydro-1H-indol-1-yl)-N-(3-hydroxyphenyl)acetamide; 2-(5-chloro-2-oxo-2,3-dihydro-1H-indol-1-yl)-N-(3-fluorophenyl)acetamide; 2-(5-chloro-2-oxo-2,3-dihydro-1H-indol-1-yl)-N-[3-(2-pyridin-2-ylethyl)phenyl]acetamide; 2-(5-chloro-2-oxo-2,3-dihydro-1H-indol-1-yl)-N-[6-(hydroxymethyl)cyclohex-3-en-1-yl]acetamide; 5-chloro-1-[2-oxo-2-(4-pyridin-2-ylpiperazin-1-yl)ethyl]-1,3-dihydro-2H-indol-2-one; 5-chloro-1-{2-[4-(3-methylphenyl)piperazin-1-yl]-2-oxoethyl}-1,3-dihydro-2H-indol-2-one; 2-(5-chloro-2-oxo-2,3-dihydro-1H-indol-1-yl)-N-(4-hydroxy-3-methoxybenzyl)acetamide; 2-(5-chloro-2-oxo-2,3-dihydro-1H-indol-1-yl)-N-(pyridin-4-ylmethyl)-N-(tetrahydrofuran-2-ylmethyl)acetamide; 5-chloro-1-[2-(3-hydroxypiperidin-1-yl)-2-oxoethyl]-1,3-dihydro-2H-indol-2-one; 2-(5-chloro-2-oxo-2,3-dihydro-1H-indol-1-yl)-N'-isonicotinoylacetohydrazide; 5-chloro-1-(2-oxo-2-thiomorpholin-4-ylethyl)-1,3-dihydro-2H-indol-2-one; 2-(5-chloro-2-oxo-2,3-dihydro-1H-indol-1-yl)-N-(4H-1,2,4-triazol-3-yl)acetamide; 2-(5-chloro-2-oxo-2,3-dihydro-1H-indol-1-yl)-N-[4-(methylsulfonyl)benzyl]acetamide; 1-[(5-chloro-2-oxo-2,3-dihydro-1H-indol-1-yl)acetyl]octahydroquinolin-4 (1H)-one; N'-(4-bromophenyl)-2-(5-chloro-2-oxo-2,3-dihydro-1H-indol-1-yl)acetohydrazide; 2-(5-chloro-2-oxo-2,3-dihydro-1H-indol-1-yl)-N-(6-methoxypyridin-3-yl)acetamide; N-butyl-2-(5-chloro-2-oxo-2,3-dihydro-1H-indol-1-yl)acetamide; 2-(5-chloro-2-oxo-2,3-dihydro-1H-indol-1-yl)-N-(3-hydroxypropyl)acetamide; 2-(5-chloro-2-oxo-2,3-dihydro-1H-indol-1-yl)-N-[3-(dimethylamino)propyl]acetamide; 5-chloro-1-{2-oxo-2[4-(2-phenylethyl)piperazin-1-yl]ethyl}-1,3-dihydro-2H-indol-2-one; ethyl{[(5-chloro-2-oxo-2,3-dihydro-1H-indol-1-yl)acetyl]amino}acetate; 2-(5-chloro-2-oxo-2,3-dihydro-1H-indol-1-yl)-N-(3-ethoxypropyl)acetamide; 2-(5-chloro-2-oxo-2,3-dihydro-1H-indol-1-yl)-N-(2-fluoroethyl)acetamide; 2-(5-chloro-2-oxo-2,3-dihydro-1H-indol-1-yl)-N-methoxy-N-methylacetamide; 2-(5-chloro-2-oxo-2,3-dihydro-1H-indol-1-yl)-N-(3,4-dimethylphenyl)acetamide; N-(4-tert-butylphenyl)-2-(5-chloro-2-oxo-2,3-dihydro-1H-indol-1-yl)acetamide; 2-(5-chloro-2-oxo-2,3-dihydro-1H-indol-1-yl)-N-(3-hydroxy-2,2-dimethylpropyl)acetamide; 2-(5-chloro-2-oxo-2,3-dihydro-1H-indol-1-yl)-N-[1-(hydroxymethyl)propyl]acetamide; 2-(5-chloro-2-oxo-2,3-dihydro-1H-indol-1-yl)-N-(3,3,3-trifluoro-2-hydroxypropyl)acetamide; 2-(5-chloro-2-oxo-2,3-dihydro-1H-indol-1-yl)-N-(2-hydroxy-2-phenylethyl)acetamide; 5-chloro-1-{2-[4-(4-hydroxyphenyl)piperazin-1-yl]-2-oxoethyl}-1,3-dihydro-2H-indol-2-one; 2-(5-chloro-2-oxo-2,3-dihydro-1H-indol-1-yl)-N-(pyridin-4-ylmethyl)acetamide; 2-(5-chloro-2-oxo-2,3-dihydro-1H-indol-1-yl)-N-[(5-methyl-2-furyl)methyl]acetamide; 2-(5-chloro-2-oxo-2,3-dihydro-1H-indol-1-yl)-N-[3-(1H-pyrazol-1-yl)propyl]acetamide; methyl 3-[(5-chloro-2-oxo-2,3-dihydro-1H-indol-1-yl]acetyl]-1,3-thiazolidine-4-carboxylate; 5-chloro-1-[2-(2,5-dihydro-1H-pyrrol-1-yl)-2-oxoethyl]-1,3-dihydro-2H-indol-2-one; 2-(5-chloro-2-oxo-2,3-dihydro-1H-indol-1-yl)-N'-(4,5-dihydro-1H-imidazol-2-yl)acetohydrazide; 2-(5-chloro-2-oxo-2,3-dihydro-1H-indol-1-yl)-N-[2-(3,4-dimethoxyphenyl)ethyl]acetamide; 2-(5-chloro-2-oxo-2,3-dihydro-1H-indol-1-yl)-N-[2-(2-chlorophenyl)etlyllacetaniide; 2-(5-chloro-2-oxo-2,3-dihydro-1H-indol-1-yl)-N-[2-(4-methylphenyl)ethyl]acetamide; 2-(5-chloro-2-oxo-2,3-dihydro-1H-indol-1-yl)-N-(2-morpholin-4-ylethyl)acetamide; 2-(5-chloro-2-oxo-2,3-dihydro-1H-indol-1-yl)-N-[2-(3,4,5,6-tetrahydro-1-benzazocin-1 (2H)-yl)propyl]acetamide; 2-(5-chloro-2-oxo-2,3-dihydro-1H-indol-1-yl)-N-[2-(2-methylpiperidin-1-yl)ethyl]acetamide; 2-(5-chloro-2-oxo-2,3-dihydro-1H-indol-1-yl)-N-(2-nitrobenzyl)acetamide; 2-(5-chloro-2-oxo-2,3-dihydro-1H-indol-1-yl)-N-(3,4-dihydro-1H-isochromen-1-ylinethyl)acetamide; N-(2-chloro-6-fluorobenzyl)-2-(5-chloro-2-oxo-2,3-dihydro-1H-indol-1-yl)acetamide; N-benzyl-2-(5-chloro-2-oxo-2,3-dihydro-1H-indol-1-yl)-N-methylacetamide; 2-(5-chloro-2-oxo-2,3-dthydro-1H-indol-1-yl)-N-{2-[(trifluoromethyl)thio]benzyl}acetamide; 5-chloro-1-[2-(1,4-dioxa-8-azaspiro[4.5]dec-8-yl)-2-oxoethyl]-1,3-dihydro-2H-indol-2-one; 2-(5-chloro-2-oxo-2,3-dihydro-1H-indol-1-yl)-N-cycloheptylacetamide; 5-chloro-1-{2-[4-(2-morpholin-4-ylethyl)piperazin-1-yl]-2-oxoethyl}-1,3-dihydro-2H-indol-2-one; and 2-(5-chloro-2-oxo-2,3-dihydro-1H-indol-1-yl)-N-pyridin-3-ylacetamide.

In some embodiments, compounds useful in the methods and compositions of this invention are selected from the group consisting of: 2-(5-iodo-2-oxo-2,3-dihydro-1H-indol-1-yl)acetamide; 2-(5-chloro-2-oxo-2,3-dihydro-1H-indol-1-yl)acetamide; 2-(5,7-dibromo-2-oxo-2,3-dihydro-1H-indol-1-yl)acetamide; (2S)-2-(5-chloro-2-oxo-2,3-dihydro-1H-indol-1-yl)propanamide; 2-[2-oxo-5-(trifluoromethyl)-2,3-dihydro-1H-indol-1-yl]acetamide and 2-(5-chloro-7-fluoro-2-oxo-2,3-dihydro-1H-indol-1-yl)acetamide.

In another embodiment, compounds useful in the methods and compositions of this invention are selected from the group consisting of: 2-(5-chloro-2-oxo-2,3-dihydro-1H-indol-1-yl)acetamide and (2S)-2-(5-chloro-2-oxo-2,3-dihydro-1H-indol-1-yl)propanamide.

iv) U.S. Pat. No. 7,244,747:

A compound having the formula I or a pharmaceutically acceptable salt thereof,

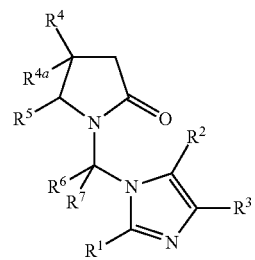

(I)

wherein $R^1$ is hydrogen, $C_{1-20}$ alkyl, $C_{3-8}$ cycloalkyl, halogen, hydroxy, alkoxy, aryloxy, ester, amido, cyano, nitro, amino, guanidine, amino derivative, alkylthio, arylthio, alkylsulfonyl, arylsulfonyl, alkylsulfinyl, arylsulfinyl, aryl or heterocycle;

$R^2$ is hydrogen, $C_{1-20}$ alkyl, alkoxy, amino, halogen, hydroxy, ester, amido, nitro, cyano, carbamate, or aryl;

$R^3$ is hydrogen, $C_{1-20}$ alkyl, alkoxy, amino, halogen, hydroxy, ester, amido, nitro, cyano, carbamate, or aryl;

or $R^2$ and $R^3$ can form together with the imidazole ring the following 1H-benzimidazole cycle

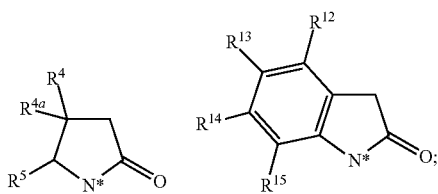

$R^4$ is hydrogen, $C_{1-20}$ alkyl, $C_{2-12}$ alkenyl, $C_{2-12}$ alkynyl, aryl, azido, alkoxycarbonylamino, arylsulfonyloxy or heterocycle;

$R^{4a}$ is hydrogen or $C_{1-20}$ alkyl;

or $R^4$ and $R^{4a}$ can form together a $C_{3-8}$ cycloalkyl;

$R^5$ is hydrogen;

or $R^4$, $R^{4a}$ and $R^5$ can form together with the 2-oxo-1-pyrrolidine ring the following 1,3-dihydro-2H-indol-2-one cycle $R^6$ is hydrogen or $C_{1-20}$ alkyl;

$R^7$ is hydrogen;

or $R^6$ and $R^7$ are linked together to form a $C_{3-6}$ cycloalkyl;

$R^8$ is hydrogen, halogen, nitro, cyano, $C_{1-20}$ alkyl or alkoxy;

$R^9$ is hydrogen, $C_{1-20}$ alkyl, halogen, hydroxy, alkoxy, aryloxy, ester, amido, cyano, nitro, amino, amino derivative, alkylthio, arylthio, alkylsulfonyl, arylsulfonyl, alkylsulfinyl or arylsulfinyl;

$R^{10}$ is hydrogen, $C_{1-20}$ alkyl, halogen, hydroxy, alkoxy, aryloxy, ester, amido, cyano, nitro, amino, amino derivative, alkylthio, arylthio, alkylsulfonyl, arylsulfonyl, alkylsulfinyl or arylsulfinyl;

$R^{11}$ is hydrogen, halogen, nitro, cyano, $C_{1-20}$ alkyl or alkoxy;

$R^{12}$ is hydrogen or halogen;

$R^{13}$ is hydrogen, nitro, halogen, heterocycle, amino, aryl, $C_{1-20}$ alkyl unsubstituted or substituted by halogen, or alkoxy unsubstituted or substituted by halogen;

$R^{14}$ is hydrogen, $C_{1-20}$ alkyl or halogen;

$R^{15}$ is hydrogen, $C_{1-20}$ alkyl or halogen;

with the proviso that $R^4$ is different from hydrogen when represents a group of formula

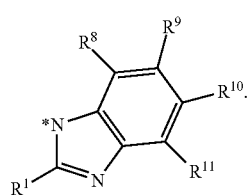

The asterisk * indicates the point of attachment of the substituents.

In a preferred embodiment, the compounds have the formula I, their tautomers, geometrical isomers (including cis and trans, Z and E isomers), enantiomers, diastereoisomers and mixtures thereof (including all possible mixtures of stereoisomers), or pharmaceutically acceptable salts thereof,

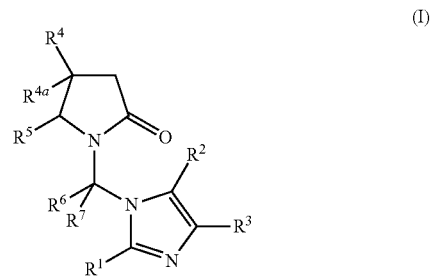

(I)

wherein $R^1$ is hydrogen, $C_{1-20}$ alkyl, $C_{3-8}$ cycloalkyl, halogen, hydroxy, ester, amido, cyano, nitro, amino, guanidine, alkylthio, alkylsulfonyl, alkylsulfinyl, aryl or heterocycle;

$R^2$ is hydrogen, $C_{1-20}$ alkyl, halogen, cyano, ester, carbamate or amido;

$R^3$ is hydrogen, cyano, $C_{1-20}$ alkyl, halogen or ester;

or $R^2$ and $R^3$ can form together with the imidazole ring the following 1H-benzimidazole cycle

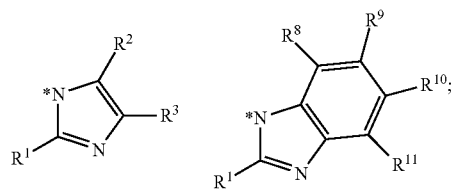

$R^4$ is hydrogen, $C_{1-20}$ alkyl, $C_{2-12}$ alkenyl or aryl;

$R^{4a}$ is hydrogen;

$R^5$ is hydrogen;

or $R^4$, $R^{4a}$ and $R^5$ can form together with the 2-oxo-1-pyrrolidine ring the following 1,3-dihydro-2H-indol-2-one cycle

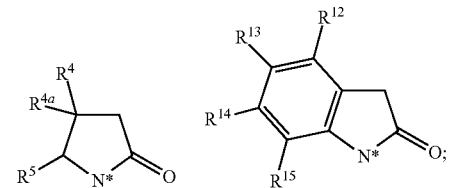

$R^6$ is hydrogen or $C_{1-20}$ alkyl;

$R^7$ is hydrogen; or $R^6$ and $R^7$ are linked together to form a $C_{3-6}$ cycloalkyl;

$R^8$ is hydrogen;

$R^9$ is hydrogen, $C_{1-20}$ alkyl, halogen or alkoxy;

$R^{10}$ is hydrogen, $C_{1-20}$ alkyl, halogen or cyano;

$R^{11}$ is hydrogen;

$R^{12}$ is hydrogen or halogen;

$R^{13}$ is hydrogen, halogen, heterocycle or $C_{1-20}$ alkyl;

$R^{14}$ is hydrogen;

$R^{15}$ is hydrogen;

with the proviso that $R^4$ is different from hydrogen when

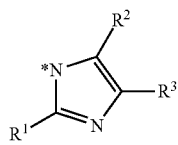

represents a group of formula

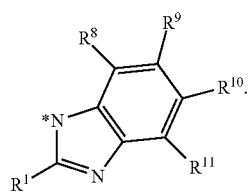

The term "alkyl", as used herein, represents saturated, monovalent hydrocarbon radicals having straight (unbranched) or branched or cyclic or combinations thereof and containing 1-20 carbon atoms, preferably 1-10 carbon atoms, more pre preferred alkyl groups have 1-3 carbon atoms. Alkyl moieties may optionally be substituted by 1 to 5 substituents independently selected from the group consisting of halogen, hydroxy, cyano, azido, aryloxy, alkoxy, alkythio, alkanoylamino, arylcarbonylamino, aminocarbonyl, methylaminocarbonyl, dimethylaminocarbonyl or aryl. Usually alkyl groups, in the present case, are methyl, ethyl, n-propyl, i-propyl, n-butyl, i-butyl, t-butyl, 1-ethylpropyl, n-heptyl, 2,4,4-trimethylpentyl, n-decyl, chloromethyl, trifluoromethyl, 2-bromo-2,2-difluoroethyl, 2,2,2-trifluoroethyl, 3,3,3-trifluoropropyl, hydroxymethyl, cyanomethyl, azidomethyl, (acetylamino)methyl, (propionylamino)methyl, (benzoylamino)methyl, (4-chlorophenoxy)methyl, benzyl, 2-phenylethyl or 2-(methylthio)ethyl. Preferred alkyl groups are methyl, ethyl, n-propyl, i-propyl, n-butyl, i-butyl, t-butyl, 1-ethylpropyl, 2,4,4-trimethylpentyl, chloromethyl, trifluoromethyl, 2,2,2-trifluoroethyl, hydroxymethyl, cyanomethyl, azidomethyl, (acetylamino)methyl, (propionylamino)methyl, (benzoylamino)methyl or 2-(methylthio)ethyl. More preferred alkyl groups are methyl, ethyl, n-propyl, i-propyl, n-butyl, azidomethyl or trifluoromethyl. Most preferred alkyl groups are methyl or n-propyl.

The term "cycloalkyl", as used herein, represents a monovalent group of 3 to 8 carbon atoms, usually 3-6 carbon atoms derived from a saturated cyclic hydrocarbon, which may be substituted by any suitable group including but not limited to one or more moieties selected from groups as described above for the alkyl groups. Preferred cycloalkyl groups are cyclopropyl and cyclohexyl.

The term "alkenyl" as used herein, represents straight, branched or cyclic unsaturated hydrocarbon radicals or combinations thereof having at least one carbon-carbon double bond, containing 2-12 carbon atoms, preferably usually 2-4 carbon atoms. Alkenyl groups are being optionally substituted with any suitable group, including but not limited to one or more moieties selected from groups as described above for the alkyl groups. Usually an alkenyl group is ethenyl(vinyl) optionally substituted by 1 to 3 halogens. Preferred alkenyl group, in the present case, is 2,2-difluorovinyl.

The term a "alkynyl" as used herein, represents straight, branched or cyclic hydrocarbon radicals or combinations thereof containing at least one carbon-carbon triple bond, containing 2-12 carbon atoms, preferably 2-6 carbon atoms, and being optionally substituted by any suitable group, including but not limited to one or more moieties selected from groups as described above for the alkyl groups. Preferably an alkynyl group is a halogenoalkynyl group (haloalkynyl group).

Groups qualified by prefixes such as "s", "i", "t" and the like (e.g. "i-propyl", "s-butyl") are branched derivatives.

The term "aryl" as used herein, is defined as phenyl optionally substituted by 1 to 4 substituents independently selected from halogen, cyano, alkoxy, alkylthio, $C_{1-3}$ alkyl or azido, preferably halogen or azido. Usually aryl groups, in the present case are phenyl, 3-chlorophenyl, 3-fluorophenyl, 4-chlorophenyl, 4-fluorophenyl, 3,4-difluorophenyl, 3,5-difluorophenyl, 3-chloro-4-fluorophenyl, 2,3,4-trifluorophenyl, 2,4,5-trifluorophenyl, 2,3,5-trifluorophenyl, 3,4,5-trifluorophenyl, 3-azido-2,4-difluorophenyl or 3-azido-2,4,6-trifluorophenyl. Preferably, aryl groups are phenyl, 3-chlorophenyl, 3-fluorophenyl, 4-chlorophenyl, 4-fluorophenyl, 3,4-difluorophenyl, 3,5-difluorophenyl, 3-chloro-4-fluorophenyl, 2,3,4-trifluorophenyl, 2,4,5-trifluorophenyl, 2,3,5-trifluorophenyl, 3,4,5-trifluorophenyl or 3-azido-2,4-difluorophenyl. Most preferred aryl groups are phenyl, 3-chlorophenyl, 3-fluorophenyl, 3,5-difluorophenyl, 2,3,4-trifluorophenyl, 2,4,5-trifluorophenyl, 2,3,5-trifluorophenyl, 3,4,5-trifluorophenyl or 3-azido-2,4-difluorophenyl.

The term "heterocycle", as used herein, is defined as including an aromatic or non aromatic cycloalkyl moiety as defined above, having at least one O, S and/or N atom interrupting the carbocyclic ring structure. Heterocyclic ring moieties can be optionally substituted by alkyl groups or halogens and optionally, one of the carbon of the carbocyclic ring structure may be replaced by a carbonyl. Usually heterocycles are 2-pyridyl, 3-pyridyl, 4-pyridyl, 2-furyl, 3-furyl, 2-thienyl, 3-thienyl, 2-tetrahydrofuranyl, 1H-pyrrol-2-yl, 1-methyl-1H-pyrrol-2-yl, 1H-pyrazol-2-yl, 1H-pyrazol-3-yl, 4-chloro-1-methyl-1H-pyrazol-3-yl, 5-chloro-1,3-dimethyl-1H-pyrazol-4-yl, 1,2,3-thiadiazol-4-yl, 3,5-dimethyl-4-isothiazyl, 1H-imidazol-2-yl, 1-methyl-1H-imidazol-2-yl, 4-methyl-1H-imidazol-5-yl, or 2-methyl-1,3-thiazol-4-yl. Preferred heterocycles are 1H-imidazol-2-yl, 1,2,3-thiadiazol-4-yl, 1H-pyrazol-3-yl, 2-furyl, 3-furyl, 2-thienyl, 1-methyl-1H-pyrrol-2-yl, 1H-pyrrol-2-yl.

The term "halogen", as used herein, includes an atom of chlorine, bromine, fluorine, iodine. Usually halogens are chlorine, bromine and fluorine. Preferred halogens are fluorine, bromine and chlorine.

The term "hydroxy", as used herein, represents a group of formula —OH.

The term "alkoxy", as used herein, represents a group of formula —OR$^a$
wherein R$^a$ is an alkyl group, as defined above. Preferred alkoxy group is methoxy.

The term "aryloxy", as used herein, represents a group of formula —OR$^b$ wherein R$^b$ is an aryl group, as defined above. Preferred aryloxy group is phenoxy.

The term "ester", as used herein, represents a group of formula —COOR$^c$ wherein R$^c$ is an alkyl group or aryl group, as defined above. Preferred ester group is methoxycarbonyl.

The term "amido", as used herein, represents a group of formula —CONH$_2$.

The term "amino", as used herein, represents a group of formula —NH$_2$.

The term "aminoderivative", as used herein, represents an alkylamino or an arylamino group, wherein the terms "alkyl" and "aryl" are defined as above.

The term "cyano", as used herein, represents a group of formula —CN.

The term "nitro", as used herein, represents a group of formula —NO$_2$.

The term "azido", as used herein, represents a group of formula —N$_3$.

The term "guanidine", as used herein, represents a group of formula —NHC(=NH)NH$_2$.

The term "alkylthio", as used herein, represents a group of formula —SR$^d$ wherein R$^d$ is an alkyl group, as defined above. Preferred alkylthio group is methylthio.

The term "alkylsulfonyl", as used herein, represents a group of formula —S(=O)$_2$R$^e$ wherein R$^e$ is an alkyl group, as defined above. Preferred alkylsulfonyl group is methylsulfonyl.

The term "alkylsulfinyl", as used herein, represents a group of formula —S(=O)R$^f$ wherein R$^f$ is an alkyl group, as defined above. Preferred alkylsulfinyl group is methylsulfinyl.

The term "arylthio", as used herein, represents a group of formula —SR$^g$ wherein R$^g$ is an aryl group, as defined above.

The term "arylsulfonyl", as used herein, represents a group of the formula —S(=O)$_2$R$^h$ wherein R$^h$ is an aryl group, as defined above.

The term "arylsulfinyl", as used herein, represents a group of the formula —S(=O)R$^i$ wherein R$^i$ is an aryl group, as defined above.

The term "carbamate" as used herein, represents a group of formula —N(H)C(O)OR$^j$, wherein R$^j$ is an alkyl or an aryl, as defined above. Usually carbamate groups are (propoxycarbonyl)amino or (benzyloaxycarbonyl)amino. Preferred carbamate group is (benzyloaxycarbonyl)amino.

The term "alkanoylamino" as used herein, represents a group of the formula —NHC(=O)R$^k$ wherein R$^k$ is an alkyl group, as defined above.

The term "(arylcarbonyl)amino" as used herein, represents a group of the formula —NHC(=O)R$^m$ wherein R$^m$ is an aryl group, as defined above. Preferred (arylcarbonyl)amino is benzoylamino.

Usually, R$^1$ is hydrogen; C$_{1-10}$ alkyl unsubstituted or substituted by halogen, hydroxy, cyano, methylthio, phenyl or 4-chlorophenoxy; hydroxy; C$_{3-6}$ cycloalkyl; halogen; ester; amido; nitro; cyano; amino; phenyl; alkylthio; alkylsulfonyl; alkylsulfinyl; heterocycle unsubstituted or substituted by alkyl groups; or guanidine. Preferably, R$^1$ is hydrogen; methyl; ethyl; i-propyl; n-propyl; cyclopropyl; n-butyl; i-butyl; t-butyl; 1-ethylpropyl; 2,4,4-trimethylpentyl; hydroxymethyl; chloromethyl; trifluoromethyl; 2,2,2-trifluoroethyl; cyanomethyl; 2-(methylthio)ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2-thienyl; 1H-pyrazol-3-yl; 1,2,3-thiadiazol-4-yl or 1H-imidazol-2-yl. More preferably, R$^1$ is hydrogen; methyl; ethyl; i-propyl; n-propyl; n-butyl; methylthio; nitro; cyano; amino; chloro or 1H-pyrrol-2-yl. Most preferably, R$^1$ is hydrogen; methyl; methylthio; nitro; cyano; amino or chloro.

Usually, R$^2$ is hydrogen; C$_{1-4}$ alkyl unsubstituted or substituted by hydroxy, alkanoylamino or benzoylamino; halogen; ester; cyano; alkyl carbamate; [(N-methoxy-N-methyl)amino]carbonyl. Preferably, R$^2$ is hydrogen; methyl; hydroxymethyl; (acetylamino)methyl; (propionylamino)methyl; (benzoylamino)methyl; [(benzyloxy)carbonyl]amino; chloro or cyano. More preferably, R$^2$ is hydrogen; chloro or cyano.

Usually, R$^3$ is hydrogen; C$_{1-4}$ alkyl unsubstituted or substituted by hydroxy; halogen; ester or cyano. Preferably, R$^3$ is hydrogen; hydroxymethyl; chloro; cyano. More preferably, R$^3$ is hydrogen or cyano. Most preferred R$^3$ is hydrogen.

Usually, R$^4$ is hydrogen; C$_{1-4}$ alkyl unsubstituted or substituted by halogens; C$_{2-4}$ alkenyl substituted by halogens or phenyl group unsubstituted or substituted by azido or/and halogens. Preferably, R$^4$ is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl or 3-azido-2,4,6-trifluorophenyl. More preferably, R$^4$ is hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl or 3-azido-2,4-difluorophenyl. Most preferably, R$^4$ is n-propyl; 2,2-difluorovinyl; phenyl; 3-chlorophenyl; 3-fluorophenyl; 3,5-difluorophenyl; 2,3,4-trifluorophenyl; 2,4,5-trifluorophenyl; 2,3,5-trifluorophenyl; 3,4,5-trifluorophenyl or 3-azido-2,4-difluorophenyl.

Usually, R$^{4a}$ is hydrogen.

Usually, R$^5$ is hydrogen.

Usually, R$^6$ is hydrogen or C$_{1-10}$ alkyl unsubstituted or substituted by hydroxy or azido. Preferably, R$^6$ is hydrogen or azidomethyl. More preferably R$^6$ is hydrogen.

Usually R$^7$ is hydrogen.

In other preferred embodiments, R$^6$ and R$^7$ are linked to form a cyclopropyl.

In other preferred embodiments, R$^2$ and R$^3$ can form together with the imidazole ring the following 1H-benzimidazole cycle

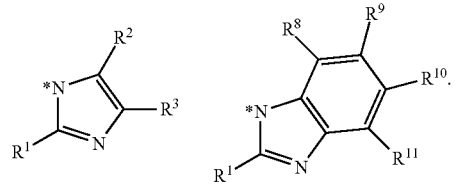

Usually, R$^8$ is hydrogen.

Usually, R$^9$ is hydrogen; halogen; C$_{1-3}$ alkyl or alkoxy. Preferably, R$^9$ is hydrogen; methyl; chloro or methoxy. More preferred R$^9$ is hydrogen.

Usually, R$^{10}$ is hydrogen; halogen; cyano; C$_{1-3}$ alkyl unsubstituted or substituted by halogens; or alkoxy. Preferably, R$^{10}$ is methyl; hydrogen; trifluoromethyl; fluoro; cyano or methoxy. More preferred R$^{10}$ is hydrogen; trifluoromethyl; fluoro or cyano.

Usually, R$^{11}$ is hydrogen.

In other preferred embodiments, R$^4$, R$^{4a}$ and R$^5$ can form together with the 2-oxo-1-pyrrolidine ring the following 1,3-dihydro-2H-indol-2-one cycle

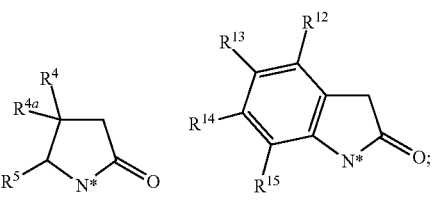

Usually, $R^{12}$ is hydrogen or halogen. Preferably $R^{12}$ is hydrogen; chloro or fluoro. More preferred $R^{12}$ is hydrogen.

Usually, $R^{13}$ is hydrogen; $C_{1-3}$ alkyl; halogen or thiazolyl unsubstituted or substituted by alkyl groups, such as methylthiazolyl. Preferably $R^{13}$ is hydrogen; chloro; bromo or methyl. Most preferred $R^{13}$ is chloro; bromo or methyl.

Usually $R^{14}$ is hydrogen.

Usually, $R^{15}$ is hydrogen.

Combinations of one or more of these preferred compound groups are especially preferred.

Generally, among the embodiments, the compounds of formula I, or pharmaceutically acceptable salts thereof, are those wherein $R^1$ is selected from hydrogen; $C_{1-10}$ alkyl unsubstituted or substituted by halogen, hydroxy, cyano, methylthio, phenyl or 4-chlorophenoxy; $C_{3-6}$ cycloalkyl; halogen; ester; amido; nitro; cyano; amino; phenyl; alkylthio; alkylsulfonyl; alkylsulfinyl; heterocycle unsubstituted or substituted by alkyl group; or guanidine;

$R^2$ is selected from hydrogen; $C_{1-4}$ alkyl unsubstituted or substituted by hydroxy, alkanoylamino or benzoylamino; halogen; ester; cyano; alkyl carbamate or [(N-methoxy-N-methyl)amino]carbonyl.

$R^3$ is selected from hydrogen; $C_{1-4}$ alkyl unsubstituted or substituted by hydroxy; halogen; ester or cyano;

$R^4$ is selected from hydrogen; $C_{1-4}$ alkyl unsubstituted or substituted by halogens; $C_{2-4}$ alkenyl substituted by halogens or phenyl group unsubstituted or substituted by azido or/and halogens;

$R^{4a}$ is hydrogen;

$R^5$ is hydrogen;

$R^6$ is selected from hydrogen or $C_{1-10}$ alkyl unsubstituted or substituted by hydroxy or azido;

$R^7$ is hydrogen;

or $R^6$ and $R^7$ can be linked to form a cyclopropyl;

or $R^2$ and $R^3$ can form together with the imidazole ring the following 1H-benzimidazole cycle

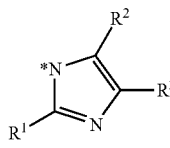 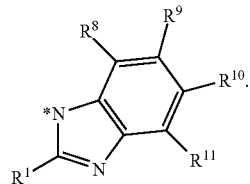

$R^8$ is hydrogen;

$R^9$ is selected from hydrogen; halogen; $C_{1-3}$ alkyl; alkoxy;

$R^{10}$ is selected from hydrogen; halogen; cyano or $C_{1-3}$ alkyl unsubstituted or substituted by halogens; or alkoxy;

$R^{11}$ is hydrogen;

or $R^4$, $R^{4a}$ and $R^5$ can form together with the 2-oxo-1-pyrrolidine ring the following 1,3-dihydro-2H-indol-2-one cycle

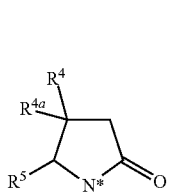 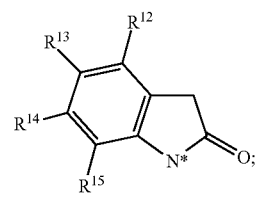

$R^{12}$ is selected from hydrogen or halogen;

$R^{13}$ is selected from hydrogen; $C_{1-3}$ alkyl; halogen; thiazolyl unsubstituted or substituted by alkyl groups, such as methylthiazolyl;

$R^{14}$ is hydrogen;

$R^{15}$ is hydrogen;

with the proviso that $R^4$ is different from hydrogen when

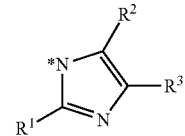

represents a group of formula

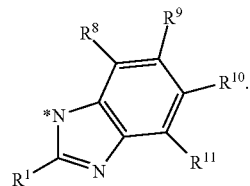

In a preferred embodiment, the compounds of formula I, or pharmaceutically acceptable salt thereof, are those wherein $R^1$ is selected from hydrogen; methyl; ethyl; i-propyl; n-propyl; cyclopropyl; n-butyl; i-butyl; t-butyl; 1-ethylpropyl; 2,4,4-trimethylpentyl; trifluoromethyl; 2,2,2-trifluoroethyl; hydroxymethyl; chloromethyl; cyanomethyl; 2-(methylthio)ethyl; chloro; bromo; nitro; cyano; amino; aminocarbonyl; methoxycarbonyl; methylthio; methylsulfinyl; methylsulfonyl; phenyl; 2-furyl; 3-furyl; 1H-pyrrol-2-yl; 1-methyl-1H-pyrrol-2-yl; 2-thienyl; 1H-pyrazol-3-yl; 1,2,3-thiadiazol-4-yl; or 1H-imidazol-2-yl;

$R^2$ is selected from hydrogen; methyl; hydroxymethyl; (acetylamino)methyl; (propionylamino)methyl; (benzoylamino)methyl; (benzyloxycarbonyl)amino; chloro; or cyano;

$R^3$ is selected from hydrogen; hydroxymethyl; chloro; cyano;

or $R^2$ and $R^3$ can form together with the imidazole ring the following 1H-benzimidazole cycle

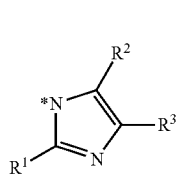 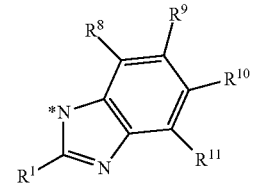

$R^8$ is hydrogen;

$R^9$ is selected from hydrogen; methyl; choro; methoxy;

$R^{10}$ is selected from methyl; hydrogen; trifluoromethyl; fluoro; cyano; or methoxy;

$R^{11}$ is hydrogen;

$R^4$ is selected from hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; 3-azido-2,4-difluorophenyl; or 3-azido-2,4,6-trifluorophenyl.

$R^{4a}$ is hydrogen; $R^5$ is hydrogen;
or $R^4$, $R^{4a}$ and $R^5$ can form together with the 2-oxo-1-pyrrolidine ring the following 1,3-dihydro-2H-indol-2-one cycle

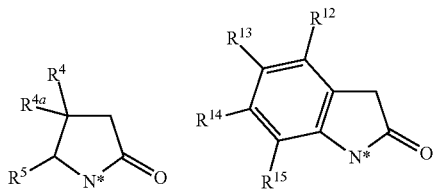

$R^{12}$ is selected from hydrogen; chloro; fluoro;
$R^{13}$ is selected from hydrogen; chloro; bromo; methyl;
$R^{14}$ is hydrogen;
$R^{15}$ hydrogen;
$R^6$ is selected from hydrogen; azidomethyl;
$R^7$ is hydrogen;
or $R^6$ and $R^7$ are linked to form a cyclopropyl;
with the proviso that $R^4$ is different from hydrogen when

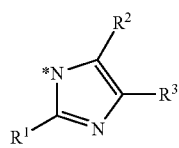

represents a group of formula

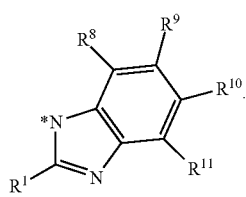

In a more preferred embodiment, the compounds of formula I, or pharmaceutically acceptable salt thereof, are those wherein
$R^1$ is selected from hydrogen; methyl; ethyl; i-propyl; n-propyl; n-butyl; methylthio; nitro; cyano; amino; chloro; or 1H-pyrrol-2-yl;
$R^2$ is selected from hydrogen; chloro; cyano;
$R^3$ is selected from hydrogen; cyano;
or $R^2$ and $R^3$ can form together with the imidazole ring the following 1H-benzimidazole cycle

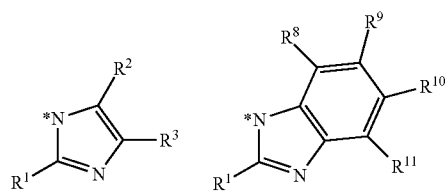

$R^8$ is hydrogen;
$R^9$ is hydrogen;
$R^{10}$ is selected from hydrogen; trifluoromethyl; fluoro; cyano;
$R^{11}$ is hydrogen;
$R^4$ is selected from hydrogen; n-propyl; 2,2-difluorovinyl; phenyl; 3-chlorophenyl; 3-fluorophenyl; 4-chlorophenyl; 4-fluorophenyl; 3,5-difluorophenyl; 3,4-difluorophenyl; 3-chloro-4-fluorophenyl; 2,3,4-trifluorophenyl; 2,4,5-trifluorophenyl; 2,3,5-trifluorophenyl; 3,4,5-trifluorophenyl; or 3-azido-2,4-difluorophenyl;
$R^{4a}$ is hydrogen;
$R^5$ is hydrogen;
or $R^4$, $R^{4a}$ and $R^5$ can form together with the 2-oxo-1-pyrrolidine ring the following 1,3-dihydro-2H-indol-2-one cycle

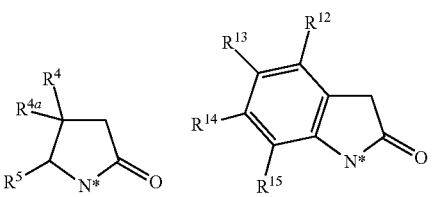

wherein
$R^{12}$ is hydrogen;
$R^{13}$ is selected from methyl; chloro; bromo;
$R^{14}$ is hydrogen;
$R^{15}$ hydrogen;
$R^6$ is hydrogen;
$R^7$ is hydrogen;
with the proviso that $R^4$ is different from hydrogen when

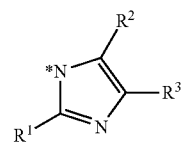

represents a group of formula

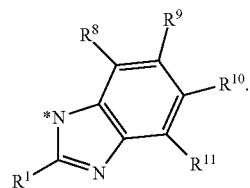

In a most preferred embodiment, the compounds of formula I, or pharmaceutically acceptable salt thereof, are those wherein
$R^1$ is selected from hydrogen; methyl; methylthio; nitro; cyano; amino; chloro;
$R^2$ is selected from hydrogen; chloro; cyano;
$R^3$ is hydrogen;
$R^4$ is selected from n-propyl; 2,2-difluorovinyl; phenyl; 3-chlorophenyl; 3-fluorophenyl; 3,5-difluorophenyl; 2,3,4-trifluorophenyl; 2,4,5-trifluorophenyl; 2,3,5-trifluorophenyl; 3,4,5-trifluorophenyl; 3-azido-2,4-difluorophenyl;
$R^{4a}$ is hydrogen;
$R^5$ is hydrogen;
or $R^4$, $R^{4a}$ and $R^5$ can form together with the 2-oxo-1-pyrrolidine ring the following 1,3-dihydro-2H-indol-2-one cycle

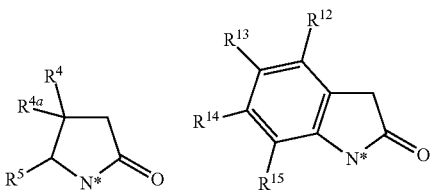

R$^{12}$ is hydrogen;
R$^{13}$ is selected from chloro; bromo; methyl;
R$^{14}$ is hydrogen;
R$^{15}$ hydrogen;
R$^6$ is hydrogen;
R$^7$ is hydrogen.

In some embodiments, compounds useful in the methods and compositions of this invention are selected from the group consisting of: 1-(1H-imidazol-1-ylmethyl)pyrrolidin-2-one; 1-(1H-imidazol-1-ylmethyl)-4-phenylpyrrolidin-2-one; 4-(3-azido-2,4,6-trifluorophenyl)-1-(1H-imidazol-1-ylmethyl)pyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl) pyrrolidin-2-one; 1-[(2-ethyl-1H-imidazol-1-yl)methyl]-4-propylpyrrolidin-2-one; 1-[(2-isopropyl-1H-imidazol-1-yl)methyl]-4-propylpyrrolidin-2-one; 1-[(2-methyl-1H-imidazol-1-yl)methyl]-4-propylpyrrolidin-2-one; 1-[(2-phenyl-1H-imidazol-1-yl)methyl]-4-propylpyrrolidin-2-one; 4-propyl-1-[(2-propyl-1H-imidazol-1-yl)methyl]pyrrolidin-2-one; (+)-1-(1H-imidazol-1-ylmethyl)-4-propylpyrrolidin-2-one; (−)-1-(1H-imidazol-1-ylmethyl)-4-propylpyrrolidin-2-one; 4-(2,2-difluorovinyl)-1-(1H-imidazol-1-ylmethyl)pyrrolidin-2-one; 4-(3-chlorophenyl)-1-(1H-imidazol-1-ylmethyl)pyrrolidin-2-one; 1-{[2-(methylthio)-1H-imidazol-1-yl]methyl}-4-propylpyrrolidin-2-one; 1-{[2-(methylsulfinyl)-1H-imidazol-1-yl]methyl}-4-propylpyrrolidin-2-one; 1-[(2-tert-butyl-1H-imidazol-1-yl)methyl]-4-propylpyrrolidin-2-one; 1-[1-(1H-imidazol-1-yl)cyclopropyl]pyrrolidin-2-one; 1-[(2-methyl-1H-imidazol-1-yl)methyl]-4-phenylpyrrolidin-2-one; 1-{[2-(methylsulfonyl)-1H-imidazol-1-yl]methyl}-propylpyrrolidin-2-one; 1-[(2-oxo-4-propylpyrrolidin-1-yl)methyl]-1H-imidazole-2-carboxamide, 4-(4-fluorophenyl)-1-(1H-imidazol-1-ylmethyl)pyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylmethyl)pyrrolidin-2-one; 4-(3,5-difluorophenyl)-1-(1H-imidazol-1-ylmethyl)pyrrolidin-2-one; 4-(3,4-difluorophenyl)-1-(1H-imidazol-1-ylmethyl)pyrrolidin-2-one; 4-(3-chloro-4-fluorophenyl)-1-(1H-imidazol-1-ylmethyl)pyrrolidin-2-one; 4-(4-chlorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(1H-imidazol-1-ylmethyl)-4-(2,3,5-trifluorophenyl)pyrrolidin-2-one; 1-(1H-imidazol-1-ylmethyl)-4-(2,4,5-trifluorophenyl)pyrrolidin-2-one; 1-{[2-(hydroxymethyl)-1H-imidazol-1-yl]methyl}-4-propylpyrrolidin-2-one; methyl 1-[(2-oxo-4-propylpyrrolidin-1-yl)methyl]-1H-imidazole-2-carboxylate; 1-[(2-nitro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-2-carbonitrile; 1-[(2-amino-1H-imidazol-1-yl)methyl]-4-propylpyrrolidin-2-one; 1-[(2,4-dichloro-1H-imidazol-1-yl)methyl]-4-(3,4,5-trifluorophenyl)pyrrolidin-2-one; 1-[(5-chloro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-4-carbonitrile; 1-{[2-oxo-4-(3,4,5-trifluorophenyl)pyrrolidin-1-yl]methyl}-1H-imidazole-5-carbonitrile; (+)-1-(1H-imidazol-1-ylmethyl)-4-phenylpyrrolidin-2-one; (−)-1-(1H-imidazol-1-ylmethyl)-4-phenylpyrrolidin-2-one; 1-{[2-oxo-4-(2,3,5-trifluorophenyl)pyrrolidin-1-yl]methyl}-1H-imidazole-5-carbonitrile; (−)-1-{[2-oxo-4-(2,3,4-trifluorophenyl)pyrrolidin-1-yl]methyl}-1H-imidazole-5-carbonitrile; (+)-1-{[2-oxo-4-(2,3,4-trifluorophenyl)pyrrolidin-1-yl]methyl}-1H-imidazole-5-carbonitrile; (−)-1-{[2-oxo-4-(2,3,4-trifluorophenyl)pyrrolidin-1-yl]methyl}-1H-imidazole-4-carbonitrile; (+)-1-{[2-oxo-4-(2,3,4-trifluorophenyl)-1-pyrrolidinyl]methyl}-1H-imidazole-4-carbonitrile; (−)-1-{[2-oxo-4-(3,4,5-trifluorophenyl)pyrrolidin-1-yl]methyl}-1H-imidazole-4-carbonitrile; (+)-1-{[2-oxo-4-(3,4,5-trifluorophenyl)pyrrolidin-1-yl]methyl}-1H-imidazole-4-carbonitrile; (+)-1-{[2-oxo-4-(2,4,5-trifluorophenyl)pyrrolidin-1-yl]methyl}-1H-imidazole-4-carbonitrile; (−)-1-{[2-oxo-4-(2,4,5-trifluorophenyl)pyrrolidin-1-yl]methyl}-1H-imidazole-4-carbonitrile; (−)-1-{[2-oxo-4-(2,3,5-trifluorophenyl)pyrrolidin-1-yl]methyl}-1H-imidazole-4-carbonitrile; (−)-1-{[2-oxo-4-(3,4,5-trifluorophenyl)pyrrolidin-1-yl]methyl}-1H-imidazole-5-carbonitrile; 1-{[2-oxo-4-(2,3,5-trifluorophenyl)pyrrolidin-1-yl]methyl}-1H-imidazole-5-carbonitrile; 1-{[2-oxo-4-(2,3,5-trifluorophenyl)pyrrolidin-1-yl]methyl}-1H-imidazole-5-carbonitrile; 1-[(5-methyl-2-phenyl-1H-imidazol-1-yl)methyl]-4-propylpyrrolidin-2-one; 1-[(5-methyl-1H-imidazol-1-yl)methyl]-4-propylpyrrolidin-2-one; 1-[(5-phenyl-1H-imidazol-1-yl)methyl]-4-propylpyrrolidin-2-one; 1-[(2-ethyl-5-methyl-1H-imidazol-1-yl)methyl]-4-propylpyrrolidin-2-one; 1-[(2,5-dimethyl-1H-imidazol-1-yl)methyl]-4-propylpyrrolidin-2-one; 1-[(2-chloro-1H-imidazol-1-yl)methyl]-4-(3,4,5-trifluorophenyl)pyrrolidin-2-one; 1-[2-azido-1-(1H-imidazol-1-yl)ethyl]-4-propylpyrrolidin-2-one; 1-[(4-chloro-1H-imidazol-1-yl)methyl]-4-(3,4,5-trifluorophenyl)pyrrolidin-2-one; 1-[(2-bromo-4,5-dichloro-1H-imidazol-1-yl)methyl]-4-propylpyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 1-{[5-(hydroxymethyl)-1H-imidazol-1-yl]methyl}-4-propylpyrrolidin-2-one; 1-{[4-(hydroxymethyl)-1H-imidazol-1-yl]methyl}-4-propylpyrrolidin-2-one; benzyl 1-[(2-oxo-4-propylpyrrolidin-1-yl)methyl]-1H-imidazol-5-ylcarbamate; N-[(1-{[2-oxo-4-(3,4,5-trifluorophenyl)pyrrolidin-1-yl]methyl}-1H-imidazol-5-yl)methyl]acetamide; N-[(1-{[2-oxo-4-(3,4,5-trifluorophenyl)pyrrolidin-1-yl]methyl}-1H-imidazol-5-yl)methyl]benzamide; N-[(1-{[2-oxo-4-(3,4,5-trifluorophenyl)pyrrolidin-1-yl]methyl}-1H-imidazol-5-yl)methyl]propanamide; 1-(1H-benzimidazol-1-ylmethyl)-4-propylpyrrolidin-2-one; 1-[(2-methyl-1H-benzimidazol-1-yl)methyl]-4-propylpyrrolidin-2-one; 4-propyl-1-[(2-propyl-1H-benzimidazol-1-yl)methyl]pyrrolidin-2-one; 1-[(2-isopropyl-1H-benzimidazol-1-yl)methyl]-4-propylpyrrolidin-2-one; 4-propyl-1-{[2-(trifluoromethyl)-1H-benzimidazol-1-yl]methyl}pyrrolidin-2-one; 1-{[2-(methylthio)-1H-benzimidazol-1-yl]methyl}-4-propylpyrrolidin-2-one; 1-[(2-amino-1H-benzimidazol-1-yl)methyl]-4-propylpyrrolidin-2-one; 1-{[2-(chloromethyl)-1H-benzimidazol-1-yl]methyl}-4-propylpyrrolidin-2-on-e; {1-[(2-oxo-4-propylpyrrolidin-1-yl)methyl]-1H-benzimidazol-2-yl}acetonitrile; 1-[(5-methoxy-1H-benzimidazol-1-yl)methyl]-4-propylpyrrolidin-2-one-; 1-[(5-methyl-1H-benzimidazol-1-yl)methyl]-4-propylpyrrolidin-2-one; 1-[(5, 6-dimethyl-1H-benzimidazol-1-yl)methyl]-4-propylpyrrolidin-2-one; 1-{[2-isopropyl-5-(trifluoromethyl)-1H-benzimidazol-1-yl]methyl}-4-propyl-pyrrolidin-2-one; 1-[(6-chloro-1H-benzimidazol-1-yl)methyl]-4-propylpyrrolidin-2-one; 1-[(2-oxo-4-propylpyrrolidin-1-yl)methyl]-2-propyl-1H-benzimidazole-5-carbonitrile; 1-{[2-ethyl-5-(trifluoromethyl)-1H-benzimidazol-1-yl]methyl}-4-propylpyrrolidin-2-one; 4-propyl-1-{[2-(1H-pyrrol-2-yl)-1H-benzimidazol-1-yl]methyl}pyrrolidin-2-one; 1-[(5-fluoro-2-propyl-1H-benzimidazol-1-yl)methyl]-4-propylpyrrolidin-2-one; 1-{[6-methyl-2-(1H-pyrrol-2-yl)-1H-benzimidazol-1-yl]methyl}-4-propylpyrrolidin-2-one; 1-[(6-methoxy-2-propyl-1H-benzimidazol-1-yl)methyl]-4-propylpyrrolidin-2-one; 2-butyl-1-[(2-oxo-4-propylpyrrolidin-1-yl)methyl]-1H-benzimidazole-5-carbonitrile; 1-{[2-[2-(methylthio)ethyl]-5-(trifluoromethyl)-1H-benzimidazol-1-yl]methyl}-4-propylpyrrolidin-2-one; 1-[(5-fluoro-2-isobutyl-1H-benzimidazol-1-yl)methyl]-4-propylpyrrolidin-2-one; 1-{[5-fluoro-2-(2,4,4-trimethylpentyl)-1H-benzimidazol-1-yl]methyl}-4-propylpyrrolidin-2-one; 2-cyclopropyl-1-[(2-oxo-4-propylpyrrolidin-1-yl)methyl]-1H-benzimidazole-5-carbonitrile; 1-[(2-oxo-4-propylpyrrolidin-1-yl)methyl]-2-(1H-pyrazol-3-yl)-1H-benzimidazole-5-carbonitrile; 1-[(2-cyclopropyl-5-fluoro-1H-benzimidazol-1-yl)methyl]-4-propylpyrrolidin-2-one; 1-[(5-fluoro-2-isopropyl-1H-benzimidazol-1-yl)methyl]-4-propylpyrrolidin-2-one; 1-{[2-(3-furyl)-6-methoxy-1H-benzimidazol-1-yl]methyl}-4-propylpyrrolidin-2-one; 1-[(2-cyclopropyl-6-methoxy-1H-benzimidazol-1-yl)methyl]-4-propylpyrrolidin-2-one; 1-[(2-isopropyl-6-methoxy-1H-benzimidazol-1-yl)methyl]-4-propylpyrrolidin-2-one; 1-[(2-oxo-4-propylpyrrolidin-1-yl)methyl]-2-(1,2,3-thiadiazol-4-yl-)-1H-benzimidazole-5-carbonitrile; 1-{[2-(1H-imidazol-2-yl)-5-(trifluoromethyl)-1H-benzimidazol-1-yl]methyl}-4-propylpyrrolidin-2-one; 1-{[5-fluoro-2-(2,2,2-trifluoroethyl)-1H-benzimidazol-1-yl]methyl}-4-propylpyrrolidin-2-one; 1-{[2-(1-ethylpropyl)-6-methoxy-1H-benzimidazol-1-yl]methyl}-4-propylpyrrolidin-2-one; 1-{[6-methoxy-2-(1-methyl-1H-pyrrol-2-yl)-1H-benzimidazol-1-yl]methyl}-4-propylpyrrolidin-2-one; 1-{[2-(2-furyl)-5-(trifluoromethyl)-1H-benzimidazol-1-yl]methyl}-4-propyl-pyrrolidin-2-one; 4-propyl-1-{[2-thien-2-yl-5-(trifluoromethyl)-1H-benzimidazol-1-yl]methyl-}pyrrolidin-2-one; 1-{[2-(3-furyl)-5-(trifluoromethyl)-1H-benzimidazol-1-yl]methyl}-4-propyl-pyrrolidin-2-one; 1-{[2-cyclopropyl-5-(trifluoromethyl)-1H-benzimidazol-1-yl]methyl}-4-propylpyrrolidin-2-one; 4-propyl-1-{[2-(1H-pyrrol-2-yl)-5-(trifluoromethyl)-1H-benzimidazol-1-yl]methyl}pyrrolidin-2-one; 1-(1H-imidazol-1-ylmethyl)-1,3-dihydro-2H-indol-2-one; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 4-fluoro-1-(1H-imidazol-1-ylmethyl)-1,3-dihydro-2H-indol-2-one; 4-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(2-oxo-2,3-dihydro-1H-indol-1-yl)methyl]-1H-imidazole-5-carbonitrile; and 1-[(5-chloro-2-oxo-2,3-dihydro-1H-indol-1-yl)methyl]-1H-imidazole-5-carbonitrile.

In some embodiments, compounds useful in the methods and compositions of this invention are selected from the group consisting of: 1-(1H-imidazol-1-ylmethyl)pyrrolidin-2-one, 1-(1H-imidazol-1-ylmethyl)-4-phenylpyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 1-{[2-ethyl-1H-imidazol-1-yl)methyl]-4-propylpyrrolidin-2-one; 1-[(2-isopropyl-1H-imidazol-1-yl)methyl]-4-propylpyrrolidin-2-one; 1-[(2-methyl-1H-imidazol-1-yl)methyl]-4-propylpyrrolidin-2-one; 4-propyl-1-[(2-propyl-1H-imidazol-1-yl)methyl]pyrrolidin-2-one; (+)-1-(1H-imidazol-1-ylmethyl)-4-propylpyrrolidin-2-one; (−)-1-(1H-imidazol-1-ylmethyl)-4-propylpyrrolidin-2-one; 4-(2,2-difluorovinyl)-1-(1H-imidazol-1-ylmethyl)pyrrolidin-2-one; 4-(3-chlorophenyl)-1-(1H-imidazol-1-ylmethyl)pyrrolidin-2-one; 1-{[2-(methylthio)-1H-imidazol-1-yl]methyl}-4-propylpyrrolidin-2-one; 1-[(2-methyl-1H-imidazol-1-yl)methyl]-4-phenylpyrrolidin-2-one; 4-(4-fluorophenyl)-1-(1H-imidazol-1-ylmethyl)pyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylmethyl)pyrrolidin-2-one; 4-(3,5-difluorophenyl)-1-(1H-imidazol-1-ylmethyl)pyrrolidin-2-one; 4-(3,4-difluorophenyl)-1-(1H-imidazol-1-ylmethyl)pyrrolidin-2-one; 4-(3-chloro-4-fluorophenyl)-1-(1H-imidazol-1-ylmethyl)pyrrolidin-2-one; 4-(4-chlorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(11H-imidazol-1-ylmethyl)-4-(2,3,5-trifluorophenyl)pyrrolidin-2-one; 1-(1H-imidazol-1-ylmethyl)-4-(2,4,5-trifluorophenyl)pyrrolidin-2-one; 1-[(2-nitro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-2-carbonitrile; 1-[(2-amino-1H-imidazol-1-yl)methyl]-4-propylpyrrolidin-2-one; 1-[(5-chloro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-4-carbonitrile; 1-{[2-oxo-4-(3,4,5-trifluorophenyl)pyrrolidin-1-yl]methyl}-1H-imidazole-5-carbonitrile; (+)-1-(1H-imidazol-1-ylmethyl)-4-phenylpyrrolidin-2-one; (−)-1-(1H-imidazol-1-ylmethyl)-4-phenylpyrrolidin-2-one; (+); 1-{[2-oxo-4-(3,4,5-trifluorophenyl)pyrrolidin-1-yl]methyl}-1H-imidazole-4-carbonitrile; 1-[(2-chloro-1H-imidazol-1-yl)methyl]-4-(3,4,5-trifluorophenyl)pyrrolidin-2-one; 1-[2-azido-1-(1H-imidazol-1-yl)ethyl]-4-propylpyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 1-[(2-oxo-4-propylpyrrolidin-1-yl)methyl]-2-propyl-1H-benzimidazole-5-carbonitrile; 1-{[2-ethyl-5-(trifluoromethyl)-1H-benzimidazol-1-yl]methyl}-4-propylpyrrolidin-2-one; 4-propyl-1-{[2-(1H-pyrrol-2-yl)-1H-benzimidazol-1-yl]methyl}pyrrolidin-2-one; 1-[(5-fluoro-2-propyl-1H-benzimidazol-1-yl)methyl]-4-propylpyrrolidin-2-one; 2-butyl-1-[(2-oxo-4-propylpyrrolidin-1-yl)methyl]-1H-benzimidazole-5-carbonitrile; 1-[(5-fluoro-2-isopropyl-1H-benzimidazol-1-yl)methyl]-4-propylpyrrolidin-2-one; 1-(1H-imidazol-1-ylmethyl)-1,3-dihydro-2H-indol-2-one; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(5-chloro-2-oxo-2,3-dihydro-1H-indol-1-yl)methyl]-1H-imidazole-5-carbonitrile.

In some embodiments, compounds useful in the methods and compositions of this invention are selected from the group consisting of: 1-(1H-imidazol-1-ylmethyl)-4-phenylpyrrolidin-2-one; 1-(1H-imidazol-1-ylmethyl)-4-propylpyrrolidin-2-one; (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 4-(2,2-difluorovinyl)-1-(1H-imidazol-1-ylmethyl)pyrrolidin-2-on-e; 4-(3-chlorophenyl)-1-(1H-imidazol-1-ylmethyl)pyrrolidin-2-one; 1-{[2-(methylthio)-1H- imidazol-1-yl]methyl}-4-propylpyrrolidin-2-one; 1-[(2-methyl-1H-imidazol-1-yl)methyl]-4-phenylpyrrolidin-2-one; 1-(1H-imidazol-1-ylmethyl)-4-(3,4,5-trifluorophenyl)pyrrolidin-2-one; 4-(3-fluorophenyl)-1-(1H-imidazol-1-ylmethyl) pyrrolidin-2-one; 4-(3,5-difluorophenyl)-1-(1H-imidazol-1-ylmethyl)pyrrolidin-2-one; 1-(1H-imidazol-1-ylmethyl)-4-(2,3,4-trifluorophenyl)pyrrolidin-2-one; 1-(1H-imidazol-1-ylmethyl)-4-(2,3,5-trifluorophenyl)pyrrolidin-2-one; 1-(1H-imidazol-1-ylmethyl)-4-(2,4,5-trifluorophenyl)pyrrolidin-2-one; 1-[(2-nitro-1H-imidazol-1-yl)methyl]-4-(3,4,5-trifluorophenyl)pyrrolidin-2-one; 1-{[2-oxo-4-(3,4,5-trifluorophenyl)pyrrolidin-1-yl]methyl}-1H-imidazole-2-carbonitrile; 1-[(2-amino-1H-imidazol-1-yl)methyl]-4-propylpyrrolidin-2-one; 1-[(5-chloro-1H-imidazol-1-yl)methyl]-4-(3,4,5-trifluorophenyl)pyrrolidin-2-one; (+)-1-(1H-imidazol-1-ylmethyl)-4-phenylpyrrolidin-2-one; (−)-1-(1H-imidazol-1-ylmethyl)-4-phenylpyrrolidin-2-one; 1-[(2-chloro-1H-imidazol-1-yl)methyl]-4-(3,4,5-trifluorophenyl) pyrrolidin-2-one; 1-[(2-chloro-1H-imidazol-1-yl)methyl]-4-propylpyrrolidin-2-one; (+)-1-{[2-oxo-4-(3,4,5-trifluorophenyl)pyrrolidin-1-yl]methyl}-1H-imidazole-5-carbonitrile; 5-bromo-1-(1H-imidazol-1-ylmethyl)-1,3-dihydro-2H-indol-2-one; 5-chloro-1-(1H-imidazol-1-ylmethyl)-1,3-dihydro-2H-indol-2-one; 1-(1H-imidazol-1-ylmethyl)-5-methyl-1,3-dihydro-2H-indol-2-one; 1-[(5-chloro-2-oxo-2,3-dihydro-1H-indol-1-yl)methyl]-1H-imidazole-5-carbonitrile.

In some embodiments, compounds useful in the methods and compositions of this invention are selected from the group consisting of: (−)-4-(3-azido-2,4-difluorophenyl)-1-(1H-imidazol-1-ylmethyl)pyrrolidin-2-one; (+)-4-(3-azido-2,4-difluorophenyl)-1-(1H-imidazol-1-ylmethyl)pyrrolidin-2-one; 4-(3-azido-2,4-difluorophenyl)-1-(1H-imidazol-1-ylmethyl)pyrrolidin-2-one.

v) International Patent Application WO 2007/065595:

Compounds having formula I, their enantiomers, diastereoisomers and mixtures thereof (including all possible mixtures of stereoisomers), or pharmaceutically acceptable salts thereof,

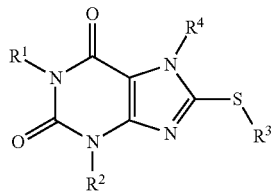

(I)

wherein
$R^1$ is hydrogen or $C_{1-6}$ alkyl;
$R^2$ is hydrogen or $C_{1-4}$ alkyl;
$R^3$ is a group of formula —$CHR^5R^6$ or a benzyl group;
$R^4$ is $C_{1-8}$ alkyl optionally substituted by alkoxycarbonyl, C3-6 cycloalkyl, aryl or heterocycle;
$R^5$ is C2-4 alkyl;
$R^6$ is C2-4 alkyl, amido or —$COOR^7$;
$R^7$ is C1-4 alkyl;

Usually when $R^3$ is a benzyl group, then $R^4$ is $C_{1-8}$ alkyl optionally substituted by alkoxycarbonyl.

Usually when $R^3$ is a group of formula —$CHR^5R^6$ then $R^4$ is $C_{1-8}$ alkyl optionally substituted by $C_{3-6}$ cycloalkyl, aryl or heterocycle.

The term "alkyl", as used herein, is a group which represents saturated, monovalent hydrocarbon radicals having straight (unbranched) or branched moieties, or combinations thereof, and containing 1-8 carbon atoms, preferably 1-6 carbon atoms; more preferably alkyl groups have 1-4 carbon atoms. Alkyl moieties may optionally be substituted by 1 to 5 substituents independently selected from the group consisting of hydroxy, alkoxy, cyano, ethynyl, alkoxycarbonyl, acyl, aryl or heterocycle. Alkyl moieties may be optionally substituted by a cycloalkyl as defined hereafter. Preferred alkyl groups are methyl, cyanomethyl, ethyl, 2-ethoxy-2-oxoethyl, 2-methoxyethyl, n-propyl, 2-oxopropyl, 3-hydroxypropyl, 2-propynyl, n-butyl, i-butyl, n-pentyl, 3-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl or (5-nitro-2-furyl)methyl. More preferred alkyl groups are methyl, ethyl, cyanomethyl, 2-methoxyethyl, n-propyl, 3-hydroxypropyl, 2-propynyl, n-butyl, 3-pentyl, n-hexyl, benzyl, 3-bromobenzyl, 3-methoxybenzyl, 3-nitrobenzyl, 3-aminobenzyl, (3,5-dimethylisoxazol-4-yl)methyl or (5-nitro-2-furyl)methyl. Most preferred alkyl groups are methyl, ethyl, 3-methoxybenzyl, 3-nitrobenzyl or (5-nitro-2-furyl)methyl.

The term "cycloalkyl", as used herein, represents a monovalent group of 3 to 8, preferably 3 to 6 carbon atoms derived from a saturated cyclic hydrocarbon, which may be substituted by any suitable group including but not limited to one or more moieties selected from groups as described above for the alkyl groups. Preferred cycloalkyl group is cyclohexyl.

The term "aryl" as used herein, is defined as a phenyl group optionally substituted by 1 to 4 substituents independently selected from halogen, amino, nitro, alkoxy or aminosulfonyl. Preferred aryl groups are phenyl, 2-bromophenyl, 3-bromophenyl, 4-bromophenyl, 3-methoxyphenyl, 3-nitrophenyl, 3-aminophenyl or 4-(aminosulfonyl)phenyl.

The term "phenyl", as used herein, represents an aromatic hydrocarbon group of formula —$C_6H_5$.

The term "benzyl group", as used herein, represents a group of formula —$CH_2$-aryl. Preferred benzyl groups are benzyl, 2-bromobenzyl, 3-bromobenzyl, 4-bromobenzyl, 3-methoxybenzyl, 3-nitrobenzyl, 3-aminobenzyl or 4-(aminosulfonyl)benzyl. More preferred benzyl groups are benzyl, 3-bromobenzyl, 3-methoxybenzyl, 3-nitrobenzyl or 3-aminobenzyl. Most preferred alkyl groups are 3-methoxybenzyl or 3-nitrobenzyl.

The term "halogen", as used herein, represents an atom of fluorine, chlorine, bromine, or iodine. Preferred halogen is bromine.

The term "hydroxy", as used herein, represents a group of formula —OH.

The term "cyano", as used herein, represents a group of formula —CN.

The term "amino", as used herein, represents a group of formula —$NH_2$.

The term "ethynyl", as used herein, represents a group of formula —C≡CH.

The term "alkoxy", as used herein, represents a group of formula —$OR^a$ wherein $R^a$ is an alkyl group, as defined above. Preferred alkoxy group is methoxy.

The term "nitro", as used herein, represents a group of formula —$NO_2$.

The term "amido", as used herein, represents a group of formula —C(=O)NH2.

The term "acyl", as used herein, represents a group of formula —C(=O)$R^b$ wherein $R^b$ is an alkyl group, as defined here above. Preferred acyl group is acetyl (—C(=O)Me).

The term "alkoxycarbonyl (or ester)", as used herein, represents a group of formula —COOR$^c$ wherein R$^c$ is an alkyl group; with the proviso that R$^c$ does not represent an alkyl alpha-substituted by hydroxy. Preferred alkoxycarbonyl group is ethoxycarbonyl.

The term "heterocycle", as used herein, represents a 5-membered ring containing one or two heteroatoms selected from O or N. The heterocycle may be substituted by one or two $C_{1-4}$ alkyl or nitro. Preferred heterocycles are (3,5-dimethylisoxazol-4-yl) or (5-nitro-2-furyl). Most preferred heterocycle is (5-nitro-2-furyl).

Generally R$^1$ is hydrogen or $C_{1-6}$ alkyl. Usually R$^1$ is hydrogen or $C_{1-6}$ alkyl optionally substituted by hydroxy, alkoxy, cyano, ethynyl, alkoxycarbonyl or acyl. Preferably R$^1$ is hydrogen, methyl, cyanomethyl, 2-ethoxy-2-oxoethyl, 2-methoxyethyl, n-propyl, 2-oxopropyl, 3-hydroxypropyl, 2-propynyl, n-pentyl or n-hexyl. More preferably R$^1$ is hydrogen, methyl, cyanomethyl, 2-methoxyethyl, n-propyl, 3-hydroxypropyl or 2-propynyl. Most preferably R$^1$ is hydrogen.

Generally R$^2$ is hydrogen or $C_{1-4}$ alkyl. Usually R$^2$ is hydrogen or unsubstituted $C_{1-4}$ alkyl. Preferably R$^2$ is hydrogen, methyl or n-butyl. More preferably, R$^2$ is methyl.

Generally R$^3$ is a group of formula —CHR$^5$R$^6$ or a benzyl group. Preferably R$^3$ is 3-pentyl, 1-(aminocarbonyl)propyl, 1-(ethoxycarbonyl)propyl or 3-bromobenzyl. Most preferably R$^3$ is 1-(ethoxycarbonyl)propyl.

Generally R$^4$ is $C_{1-8}$ alkyl optionally substituted by alkoxycarbonyl, $C_{3-6}$ cycloalkyl, aryl or heterocycle. Usually R$^4$ is $C_{1-8}$ alkyl optionally substituted by cyclohexyl, phenyl, bromophenyl, aminophenyl, methoxyphenyl, nitrophenyl, aminosulfonylphenyl, 3,5-dimethylisoxazol-4-yl, 5-nitro-2-furyl or ethoxycarbonyl. Preferably R$^4$ is n-butyl, i-butyl, n-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl, (5-nitro-2-furyl)methyl or 1-(ethoxycarbonyl)propyl. More preferably R$^4$ is n-butyl, n-hexyl, benzyl, 3-bromobenzyl, 3-methoxybenzyl, 3-nitrobenzyl, 3-aminobenzyl, (3,5-dimethylisoxazol-4-yl)methyl, (5-nitro-2-furyl)methyl or 1-(ethoxycarbonyl)propyl. Most preferably R$^4$ is 3-methoxybenzyl, 3-nitrobenzyl or (5-nitro-2-furyl)methyl.

Generally R$^5$ is $C_{2-4}$ alkyl. Usually R$^5$ is unsubstituted $C_{2-4}$ alkyl. Preferably R$^5$ is ethyl.

Generally R$^6$ is $C_{2-4}$ alkyl, amido or —COOR$^7$. Usually R$^6$ is unsubstituted $C_{2-4}$ alkyl, amido or —COOR$^7$. Preferably R$^6$ is ethyl, amido or ethoxycarbonyl. Most preferably R$^6$ is ethoxycarbonyl.

Generally R$^7$ is $C_{1-4}$ alkyl. Usually R$^7$ is unsubstituted $C_{1-4}$ alkyl. Preferably, R$^7$ is ethyl.

In some embodiments, the compounds are those having formula I, and their enantiomers, diastereoisomers and mixtures thereof (including all possible mixtures of stereoisomers), or pharmaceutically acceptable salts thereof,

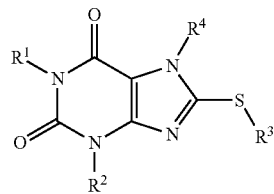

(I)

wherein
R$^1$ is hydrogen, $C_{1-6}$ alkyl optionally substituted by hydroxy, alkoxy, cyano, ethynyl, alkoxycarbonyl or acyl;
R$^2$ is hydrogen or unsubstituted $C_{1-4}$ alkyl;
R$^3$ is a group of formula —CHR$^5$R$^6$ or a benzyl group;
R$^4$ is $C_{1-8}$ alkyl optionally substituted by cyclohexyl, phenyl, bromophenyl, aminophenyl, methoxyphenyl, nitrophenyl, aminosulfonylphenyl, 3,5-dimethylisoxazol-4-yl, 5-nitro-2-furyl or ethoxycarbonyl;
R$^5$ is unsubstituted $C_{2-4}$ alkyl;
R$^6$ is unsubstituted $C_{2-4}$ alkyl, amido or —COOR$^7$;
R$^7$ is unsubstituted $C_{1-4}$ alkyl;
with the proviso that when R$^1$ is hydrogen, R$^2$ is methyl, R$^3$ is —CHR$^5$R$^6$, R$^6$ is ethoxycarbonyl and R$^5$ is ethyl, then R$^4$ is different from n-propyl, i-propyl, n-pentyl, n-heptyl, 3-bromobenzyl, 4-chlorobenzyl, 4-methylbenzyl or 2-phenylethyl.

In the above embodiment, preferably, when R$^3$ is a benzyl group, then R$^4$ is $C_{1-8}$ alkyl optionally substituted by alkoxycarbonyl.

In the above embodiment, preferably, when R$^3$ is a group of formula —CHR$^5$R$^6$, then R$^4$ is $C_{1-8}$ alkyl optionally substituted by $C_{36}$ cycloalkyl, aryl or heterocycle.

In a preferred embodiment,
R$^1$ is hydrogen, methyl, cyanomethyl, 2-ethoxy-2-oxoethyl, 2-methoxyethyl, n-propyl, 2-oxopropyl, 3-hydroxypropyl, 2-propynyl, n-pentyl or n-hexyl;
R$^2$ is hydrogen, methyl or n-butyl;
R$^3$ is 3-pentyl, 1-(aminocarbonyl)propyl, 1-(ethoxycarbonyl)propyl or 3-bromobenzyl;
R$^4$ is n-butyl, i-butyl, n-pentyl, n-hexyl, cyclohexylmethyl, benzyl, 2-bromobenzyl, 3-bromobenzyl, 4-bromobenzyl, 3-methoxybenzyl, 3-nitrobenzyl, 3-aminobenzyl, 4-(aminosulfonyl)benzyl, 1-phenylethyl, 2-phenylethyl, (3,5-dimethylisoxazol-4-yl)methyl, (5-nitro-2-furyl)methyl or 1-(ethoxycarbonyl)propyl;
with the proviso that when R$^1$ is hydrogen, R$^2$ is methyl and R$^3$ is 1-(ethoxycarbonyl)propyl, then R$^4$ is different from n-pentyl, 3-bromobenzyl or 2-phenylethyl.

In the above embodiment, preferably, when R$^3$ is 3-bromobenzyl, then R$^4$ is $C_{1-8}$ alkyl optionally substituted by alkoxycarbonyl.

In the above embodiment, preferably, when R$^3$ is 3-pentyl, 1-(aminocarbonyl)propyl or 1-(ethoxycarbonyl)propyl, then R$^4$ is different from 1-(ethoxycarbonyl)propyl.

In a more preferred embodiment,
R$^1$ is hydrogen, methyl, cyanomethyl, 2-methoxyethyl, n-propyl, 3-hydroxypropyl or 2-propynyl;
R$^2$ is methyl;
R$^3$ is 3-pentyl, 1-(aminocarbonyl)propyl, 1-(ethoxycarbonyl)propyl or 3-bromobenzyl;
R$^4$ is n-butyl, n-hexyl, benzyl, 3-bromobenzyl, 3-methoxybenzyl, 3-nitrobenzyl, 3-aminobenzyl, (3,5-dimethylisoxazol-4-yl)methyl, (5-nitro-2-furyl)methyl or 1-(ethoxycarbonyl)propyl;
with the proviso that when R$^1$ is hydrogen, R$^2$ is methyl and R$^3$ is 1-(ethoxycarbonyl)propyl, then R$^4$ is different from 3-bromobenzyl.

In the above embodiment, preferably, when R$^3$ is 3-bromobenzyl, then R$^4$ is 1-(ethoxycarbonyl)propyl;
In the above embodiment, preferably, when R$^3$ is 3-pentyl, 1-(aminocarbonyl)propyl or 1-(ethoxycarbonyl)propyl, then R$^4$ is different from 1-(ethoxycarbonyl)propyl.

In a most preferred embodiment, R$^1$ is hydrogen; R$^2$ is methyl; R$^3$ is 1-(ethoxycarbonyl)propyl; and R$^4$ is 3-methoxybenzyl, 3-nitrobenzyl or (5-nitro-2-furyl)methyl.

A further embodiment consists in compounds wherein $R^2$ is methyl, $R^3$ is a group of formula —$CHR^5R^6$ with $R^5$ being $C_{2-4}$ alkyl, $R^6$ being amido or —$COOR^7$ and $R^7$ being methyl or ethyl.

In some embodiments, compounds useful in the methods and compositions of this invention are selected from the group consisting of: ethyl 2-[(7-benzyl-1,3-dimethyl-2,6-dioxo-2,3,6,7-tetrahydro-1H-purin-8-yl)thio]butanoate; ethyl 2-{[7-(3-bromobenzyl)-1-(2-ethoxy-2-oxoethyl)-3-methyl-2,6-dioxo-2,3,6,7-tetrahydro-1H-purin-8-yl]thio}butanoate; ethyl 2-{[7-(3-bromobenzyl)-1-(2-methoxyethyl)-3-methyl-2,6-dioxo-2,3,6,7-tetrahydro-1H-purin-8-yl]thio}butanoate; ethyl 2-{[7-(3-bromobenzyl)-2,6-dioxo-2,3,6,7-tetrahydro-1H-purin-8-yl]thio}butanoate; ethyl 2-{[7-(3-bromobenzyl)-1,3-dimethyl-2,6-dioxo-2,3,6,7-tetrahydro-1H-purin-8-yl]thio}butanoate; ethyl 2-{[7-(2-bromobenzyl)-1,3-dimethyl-2,6-dioxo-2,3,6,7-tetrahydro-1H-purin-8-yl]thio}butanoate; ethyl 2-{[7-(3-bromobenzyl)-1-(cyanomethyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-propyl-2,3,6,7-tetrahydro-1H-purin-8-yl]thio}butanoate; ethyl 2-{[7-(3-bromobenzyl)-3-methyl-2,6-dioxo-1-(2-oxopropyl)-2,3,6,7-tetrahydro-1H-purin-8-yl]thio}butanoate; ethyl 2-{[7-(3-bromobenzyl)-1-(3-hydroxypropyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-(2-propynyl)-2,3,6,7-tetrahydro-1H-purin-8-yl]thio}butanoate; ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]thio}butanoate; ethyl 2-{[7-(3-aminobenzyl)-3-methyl-2,6-dioxo-2,3,6,7-tetrahydro-1H-purin-8-yl]thio}butanoate; ethyl 2-({7-[4-(aminosulfonyl)benzyl]-3-methyl-2,6-dioxo-2,3,6,7-tetrahydro-1H-purin-8-yl}thio)butanoate; ethyl 2-{[7-(4-bromobenzyl)-1,3-dimethyl-2,6-dioxo-2,3,6,7-tetrahydro-1H-purin-8-yl]thio}butanoate; ethyl 2-{[7-(cyclohexylmethyl)-1,3-dimethyl-2,6-dioxo-2,3,6,7-tetrahydro-1H-purin-8-yl]thio}butanoate; ethyl 2-{[1,3-dimethyl-2,6-dioxo-7-(1-phenylethyl)-2,3,6,7-tetrahydro-1H-purin-8-yl]thio}butanoate; ethyl 2-{[1,3-dimethyl-2,6-dioxo-7-(2-phenylethyl)-2,3,6,7-tetrahydro-1H-purin-8-yl]thio}butanoate; ethyl 2-({7-[(3,5-dimethylisoxazol-4-yl)methyl]-3-methyl-2,6-dioxo-2,3,6,7-tetrahydro-1H-purin-8-yl}thio)butanoate; ethyl 2-({3-methyl-7-[(5-nitro-2-furyl)methyl]-2,6-dioxo-2,3,6,7-tetrahydro-1H-purin-8-yl}thio)butanoate; ethyl 2-[(7-butyl-3-methyl-2,6-dioxo-2,3,6,7-tetrahydro-1H-purin-8-yl)thio]butanoate; ethyl 2-{[7-(3-bromobenzyl)-2,6-dioxo-2,3,6,7-tetrahydro-1H-purin-8-yl]thio}butanoate; ethyl 2-[(1,7-dihexyl-3-methyl-2,6-dioxo-2,3,6,7-tetrahydro-1H-purin-8-yl)thio]butanoate; ethyl 2-[(7-hexyl-3-methyl-2,6-dioxo-2,3,6,7-tetrahydro-1H-purin-8-yl)thio]butanoate; ethyl 2-[(3-methyl-2,6-dioxo-1,7-dipentyl-2,3,6,$_1$7-tetrahydro-1H-purin-8-yl)thio]butanoate; 2-{[7-(3-bromobenzyl)-3-methyl-2,6-dioxo-2,3,6,7-tetrahydro-1H-purin-8-yl]thio}butanamide; 2-[(7-butyl-3-methyl-2,6-dioxo-2,3,6,7-tetrahydro-1H-purin-8-yl)thio]butanamide; 7-(3-bromobenzyl)-8-[(1-ethylpropyl)thio]-3-methyl-3,7-dihydro-1H-purine-2,6-dione; ethyl 2-{8-[(3-bromobenzyl)thio]-1,3-dimethyl-2,6-dioxo-1,2,3,6-tetrahydro-7H-purin-7-yl}butanoate; and ethyl 2-[(7-isobutyl-3-methyl-2,6-dioxo-2,3,6,7-tetrahydro-1H-purin-8-yl)thio]butanoate.

In some embodiments, compounds useful in the methods and compositions of this invention are selected from the group consisting of: ethyl 2-[(7-benzyl-1,3-dimethyl-2,6-dioxo-2,3,6,7-tetrahydro-1H-purin-8-yl)thio]butanoate; ethyl 2-{[7-(3-bromobenzyl)-1-(2-methoxyethyl)-3-methyl-2,6-dioxo-2,3,6,7-tetrahydro-1H-purin-8-yl]thio}butanoate; ethyl 2-{[7-(3-bromobenzyl)-1,3-dimethyl-2,6-dioxo-2,3,6,7-tetrahydro-1H-purin-8-yl]thio}butanoate; ethyl 2-{[7-(3-bromobenzyl)-1-(cyanomethyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-propyl-2,3,6,7-tetrahydro-1H-purin-8-yl]thio}butanoate; ethyl 2-{[7-(3-bromobenzyl)-1-(3-hydroxypropyl)-3-methyl-2,6-dioxo-2,3,6,7-tetrahydro-1H-purin-8-yl]thio}butanoate; ethyl 2-{[7-(3-bromobenzyl)-3-methyl-2,6-dioxo-1-(2-propynyl)-2,3,6,7-tetrahydro-1H-purin-8-yl]thio}butanoate; ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]thio}butanoate; ethyl 2-{[7-(3-aminobenzyl)-3-methyl-2,6-dioxo-2,3,6,7-tetrahydro-1H-purin-8-yl]thio}butanoate; ethyl 2-({7-[(3,5-dimethylisoxazol-4-yl)methyl]-3-methyl-2,6-dioxo-2,3,6,7-tetrahydro-1H-purin-8-yl}thio)butanoate; ethyl 2-({3-methyl-7-[(5-nitro-2-furyl)methyl]-2,6-dioxo-2,3,6,7-tetrahydro-1H-purin-8-yl}thio)butanoate; ethyl 2-[(7-butyl-3-methyl-2,6-dioxo-2,3,6,7-tetrahydro-1H-purin-8-yl)thio]butanoate; ethyl 2-[(7-hexyl-3-methyl-2,6-dioxo-2,3,6,7-tetrahydro-1H-purin-8-yl)thio]butanoate; 2-{[7-(3-bromobenzyl)-3-methyl-2,6-dioxo-2,3,6,7-tetrahydro-1H-purin-8-yl]thio}butanamide; 7-(3-bromobenzyl)-8-[(1-ethylpropyl)thio]-3-methyl-3,7-dihydro-1H-purine-2,6-dione; and ethyl 2-{8-[(3-bromobenzyl)thio]-1,3-dimethyl-2,6-dioxo-1,2,3,6-tetrahydro-7H-purin-7-yl}butanoate.

In some embodiments, compounds useful in the methods and compositions of this invention are selected from the group consisting of: ethyl 2-{[7-(3-methoxybenzyl)-3-methyl-2,6-dioxo-2,3,6,7-tetrahydro-1H-purin-8-yl]thio}butanoate; ethyl 2-{[3-methyl-7-(3-nitrobenzyl)-2,6-dioxo-2,3,6,7-tetrahydro-1H-purin-8-yl]thio}butanoate; and ethyl 2-({3-methyl-7-[(5-nitro-2-furyl)methyl]-2,6-dioxo-2,3,6,7-tetrahydro-1H-purin-8-yl}thio)butanoate.

The compounds or agents or pharmaceutically acceptable salts thereof useful for the methods and compositions of this invention, also include those referred to in: i) US Patent Application 2008/0081832; ii) International Patent Application WO 2006/128692; iii) International Patent Application WO 2006/128693; iv) UK Patent No. 1,039,113; and v) UK Patent No. 1,309,692.

In one aspect of the invention, the SV2A inhibitor is levetiracetam. Levetiracetam refers to the International Union of Pure and Applied Chemistry (IUPAC) name of the compound (2S)-2-(2-oxopyrrolidin-1-yl) butanamide). Levetiracetam is a widely used antiepileptic drug. Levetiracetam binds to a specific site in the CNS: the synaptic vesicle protein 2A (SV2A) (See. e.g., Noyer et al. 1995; Fuks et al. 2003; Lynch et al. 2004; Gillard et al. 2006) and has further been shown to directly inhibit synaptic activity and neurotransmission by inhibiting presynaptic neurotransmitter release (Yang et al., 2007).

The term "prodrug" is art-recognized and is intended to encompass compounds or agents which, under physiological conditions, are converted into a SV2A inhibitor. A common method for making a prodrug is to select moieties which are hydrolyzed or metabolized under physiological conditions to provide the desired compound or agent. In other embodiments, the prodrug is converted by an enzymatic activity of the host animal to an inhibitor of SV2A.

"Analog" is used herein to refer to a compound which functionally resembles another chemical entity, but does not share the identical chemical structure. For example, an analog is sufficiently similar to a base or parent compound such that it can substitute for the base compound in therapeutic applications, despite minor structural differences. i.e., be a SV2A inhibitor.

"Derivative" is used herein to refer to the chemical modification of a compound. Chemical modifications of a compound can include, for example, replacement of hydrogen by an alkyl, acyl, or amino group. Many other modifications are also possible. A derivative of a SV2A inhibitor as used in the methods and compositions of this invention binds SV2A and reduces synaptic function by reducing pre-synaptic vesicle release, i.e., be a SV2A inhibitor.

"Pharmaceutically acceptable salts" is used herein to refer to an agent or a compound according to the invention that is a therapeutically active, non-toxic base and acid salt form of the compounds. The acid addition salt form of a compound that occurs in its free form as a base can be obtained by treating said free base form with an appropriate acid such as an inorganic acid, for example, a hydrohalic such as hydrochloric or hydrobromic, sulfuric, nitric, phosphoric and the like; or an organic acid, such as, for example, acetic, hydroxyacetic, propanoic, lactic, pyruvic, malonic, succinic, maleic, fumaric, malic, tartaric, citric, methanesulfonic, ethanesulfonic, benzenesulfonic, p-toluenesulfonic, cyclic, salicylic, p-aminosalicylic, pamoic and the like. See, e.g., WO 01/062726.

Compounds containing acidic protons may be converted into their therapeutically active, non-toxic base addition salt form, e. g. metal or amine salts, by treatment with appropriate organic and inorganic bases. Appropriate base salt forms include, for example, ammonium salts, alkali and earth alkaline metal salts, e. g. lithium, sodium, potassium, magnesium, calcium salts and the like, salts with organic bases, e. g. N-methyl-D-glucamine, hydrabamine salts, and salts with amino acids such as, for example, arginine, lysine and the like. Conversely, said salt forms can be converted into the free forms by treatment with an appropriate base or acid. Compounds and their salts can be in the form of a solvate, which is included within the scope of the present invention. Such solvates include for example hydrates, alcoholates and the like. See, e.g., WO 01/062726.

Many of the compounds useful in the methods and compositions of this invention have at least one stereogenic center in their structure. This stereogenic center may be present in a R or a S configuration, said R and S notation is used in correspondence with the rules described in Pure Appl. Chem. (1976), 45,11-30. The invention also relates to all stereoisomeric forms such as enantiomeric and diastereoisomeric forms of the compounds or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the invention includes both mixture and separate individual isomers. Multiple substituents on the piperidinyl or the azepanyl ring can also stand in either cis or trans relationship to each other with respect to the plane of the piperidinyl or the azepanyl ring. Some of the compounds may also exist in tautomeric forms. Such forms although not explicitly indicated in the above formula are intended to be included within the scope of the present invention. With respect to the methods and compositions of the present invention reference to a compound or compounds is intended to encompass that compound in each of its possible isomeric forms and mixtures thereof unless the particular isomeric form is referred to specifically. See, e.g., WO 01/062726.

This invention provides methods and compositions for treating age-related cognitive impairment or the risk thereof using an inhibitor of SV2A and analogs, derivatives, and pharmaceutically acceptable salts and solvates thereof. The methods and compositions may be used for human patients in clinical applications in the treating age-related cognitive impairment in conditions such as MCI, ARCD and AAMI or for the risk thereof. The dose of the composition and dosage interval for the method is, as described herein, one that is safe and efficacious in those ° applications.

In certain embodiments of the invention, the inhibitor of SV2A activity is levetiracetam or a pharmaceutically acceptable salt or solvate thereof or a composition containing such levetiracetam, and the invention relates to such levetiracetam or to a levetiracetam-containing compositions and a method of using such levetiracetam or that composition for improving cognitive function in patients suffering from age-related cognitive impairment or at risk thereof, the method comprising the step of administering to the subject a therapeutically effective amount of levetiracetam or a composition containing it. In other embodiments, analogs or derivatives of levetiracetam and pharmaceutically acceptable salt or solvate thereof are used.

In certain embodiments of the invention, the inhibitor of SV2A activity is brivaracetam or a pharmaceutically acceptable salt or solvate thereof or a composition containing such brivaracetam, and the invention relates to such brivaracetam or to a brivaracetam-containing compositions and a method of using such brivaracetam or that composition for improving cognitive function in patients suffering from age-related cognitive impairment or at risk thereof, the method comprising the step of administering to the subject a therapeutically effective amount of brivaracetam or a composition containing it. In other embodiments, analogs or derivatives of brivaracetam and pharmaceutically acceptable salt or solvate thereof are used.

The subject to be treated by the methods and compositions of this invention exhibits age-related cognitive impairment or is at risk of such impairment. In some embodiments, the age-related cognitive impairment includes, without limitation, MCI, ARCD and AAMI.

It will be appreciated that compounds and agents used in the compositions and methods of the present invention preferably should readily penetrate the blood-brain barrier-when peripherally administered. Compounds which cannot penetrate the blood-brain barrier, however, can still be effectively administered directly into the central nervous system, e.g., by an intraventricular route.

In some embodiments of this invention, the SV2A inhibitor is formulated with a pharmaceutically acceptable carrier. In other embodiments, no carrier is used. For example, the SV2A inhibitor can be administered alone or as a component of a pharmaceutical formulation (therapeutic composition). The SV2A inhibitor may be formulated for administration in any convenient way for use in human medicine.

In some embodiments, the therapeutic methods of the invention include administering the composition of a compound or agent topically, systemically, or locally. For example, therapeutic compositions of compounds or agents of the invention may be formulated for administration by, for example, injection (e.g., intravenously, subcutaneously, or intramuscularly), inhalation or insufflation (either through the mouth or the nose) or oral, buccal, sublingual, transdermal, nasal, or parenteral administration. The compositions of compounds or agents described herein may be formulated as part of an implant or device, or formulated for slow or extended release. When administered, the therapeutic composition of compounds or agents for use in this invention is in a pyrogen-free, physiologically acceptable form. Techniques and formulations generally may be found in Remington's Pharmaceutical Sciences, Meade Publishing Co., Easton, Pa.

In certain embodiments, pharmaceutical compositions suitable for parenteral administration may comprise the SV2A inhibitor in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

A composition comprising a SV2A inhibitor may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

In certain embodiments of the invention, compositions comprising a SV2A inhibitor can be administered orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and the like, each containing a predetermined amount of the SV2A inhibitor as an active ingredient.

In solid dosage forms for oral administration (capsules, tablets, pills, dragees, powders, granules, and the like), one or more compositions comprising the SV2A inhibitor may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the SV2A inhibitor, the liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

As described above, the compounds, agents, and compositions thereof may be administered for slow, controlled or extended release. The term "extended release" is widely recognized in the art of pharmaceutical sciences and is used herein to refer to a controlled release of an active compound or agent from a dosage form to an environment over (throughout or during) an extended period of time, e.g. greater than or equal to one hour. An extended release dosage form will release drug at substantially constant rate over an extended period of time or a substantially constant amount of drug will be released incrementally over an extended period of time. The term "extended release" used herein includes the terms "controlled release", "prolonged release", "sustained release", or "slow release", as these terms are used in the pharmaceutical sciences. In some embodiments, the extended release dosage is administered in the form of a patch or a pump.

A person of ordinary skill in the art, such as a physician, is readily able to determine the required amount of SV2A inhibitor(s) to treat the subject using the compositions and methods of this invention. It is understood that the dosage regimen will be determined for an individual, taking into consideration, for example, various factors that modify the action of inhibitors of SV2A, the severity or stage of the disease, route of administration, and characteristics unique to the individual, such as age, weight, size, and extent of cognitive impairment.

Furthermore, although the invention has been exemplified using levetiracetam, the results and the method of the instant invention are also applicable to other SV2A inhibitors. Therefore, the present invention also provides compositions of and methods for using other such SV2A inhibitors to improve cognitive function in patients suffering from age-related cognitive impairment or at risk thereof.

It is well-known in the art that normalization to body surface area is an appropriate method for extrapolating doses between species. To calculate the human equivalent dose (HED) from a dosage used in the treatment of age-dependent cognitive impairment in rats, the formula HED (mg/kg)=rat dose (mg/kg)×0.16 may be employed (see Estimating the Safe Starting Dose in Clinical Trials for Therapeutics in Adult Healthy Volunteers, December 2002, Center for Biologics Evaluation and Research). For example, using that formula, a dosage of 10 mg/kg in rats is equivalent to 1.6 mg/kg in humans. This conversion is based on a more general formula HED=animal dose in mg/kg×(animal weight in kg/human weight in kg)$^{0.33.}$ In certain embodiments of the invention, the dose of the SV2A inhibitor is 0.1 to 5 mg/kg/day (which, given a typical human subject of 70 kg, is 7 to 350 mg/day). Doses that may be used include, but are not limited to 0.1, 0.5, 1, 1.5, 2, 2.5, 3, 4, 5 mg/kg/day. In a embodiments, the dose is 1-2 mg/kg/day (which, given a typical human subject of 70 kg, is 70-140 mg/day). In other embodiments of the invention, the dose of the SV2A inhibitor is 0.1 to 0.2 mg/kg/day. Other doses higher than, intermediate to, or less than these doses may also be used and may be determined by one skilled in the art following the methods of this invention.

In certain embodiments of the invention, the dose of the SV2A inhibitor is 0.01 to 2.5 mg/kg/day (which, given a typical human subject of 70 kg, is about 0.7-180 mg/day). Doses that may be used include, but are not limited to 0.01, 0.02, 0.03, 0.04, 0.06, 0.08, 0.12, 0.14, 0.16, 0.18, 0.2, 0.4, 0.6, 0.8, 1.0, 1.2, 1.4, 1.6, 1.8, 2.0, 2.2, 2.4, 2.5 mg/kg/day. In some embodiments, the dose is 0.1-2.5 mg/kg/day (which, given a typical human subject of 70 kg, is about 7-180 mg/day). In some embodiments, the dose is 0.4-2.5 mg/kg/day (which, given a typical human subject of 70 kg, is about 25-180 mg/day). In some embodiments of the invention, the dose of the SV2A inhibitor is 0.6 to 1.8 mg/kg/day. In some embodiments of the invention, the dose of the SV2A inhibitor is 0.04 to 2.5 mg/kg/day. In some embodiments of the invention, the dose of the SV2A inhibitor is 0.06 to 1.8 mg/kg/day. Other doses higher than, intermediate to, or less than these doses may also be used and may be determined by one skilled in the art following the methods of this invention.

In certain embodiments of the invention, the interval of administration is 12 or 24 hours. Administration at less frequent intervals, such as once every 6 hours, may also be used. In some embodiments, the SV2A inhibitor is administered every 12 or 24 hours at a total daily dose of 0.1 to 5 mg/kg (e.g., in the case of administration every 12 hours of a daily dose of 2 mg/kg, each administration is 1 mg/kg). In some embodiments, the SV2A inhibitor is administered every 24 hours at a daily dose of 1 to 2 mg/kg. In another embodiment, the selective inhibitor of SV2A is administered every 24 hours at a daily dose of 0.1-0.2 mg/kg. In some embodiments, the SV2A inhibitor is administered every 12 or 24 hours at a daily dose of 0.01 to 2.5 mg/kg (e.g., in the case of administration every 12 hours of a daily dose of 0.8 mg/kg, each administration is 0.4 mg/kg). In some embodiments, the SV2A inhibitor is administered every 12 or 24 hours at a daily dose of 0.1 to 2.5 mg/kg. In some embodiments, the SV2A inhibitor is administered every 12 or 24 hours at a daily dose of 0.4 to 2.5 mg/kg. In some embodiments, the SV2A inhibitor is administered every 12 or 24 hours at a daily dose of 0.6 to 1.8 mg/kg. In some embodiments, the selective inhibitor of SV2A is administered every 12 or 24 hours at a daily dose of 0.04-2.5 mg/kg. In some embodiments, the selective inhibitor of SV2A is administered every 12 or 24 hours at a daily dose of 0.06-1.8 mg/kg.

If administered by an implant, a device or a slow or extended release formulation, the SV2A inhibitor can be administered one time, or one or more times periodically throughout the lifetime of the patient as necessary. Other administration intervals intermediate to or shorter than these dosage intervals for clinical applications may also be used and may be determined by one skilled in the art following the methods of this invention.

Desired time of administration can be determined by routine experimentation by one skilled in the art. For example, the SV2a inhibitor may be administered for a period of 1-4 weeks, 1-3 months, 3-6 months, 6-12 months, 1-2 years, or more, up to the lifetime of the patient.

In addition to inhibitors of SV2A, the compositions and methods of this invention can also include other therapeutically useful agents. These other therapeutically useful agents may be administered in a single formulation, simultaneously or sequentially with the SV2A inhibitors according to the methods of the invention.

In some embodiments, the present invention provides methods and compositions of treating age-related cognitive impairment, which method comprises administering to a subject in need or at risk thereof an inhibitor of SV2A, as described above, in combination with valproic acid (or salts, or solvates, or analogs or derivatives thereof).

Analogs and derivatives of valproic acid (VPA) useful for the methods and compositions of this invention include compounds of the formula:

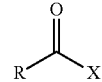

wherein, independently for each occurrence:
X is —OH, $C_{1-10}$ alkoxy, —O-alkali metal, —N(R$^1$)$_2$, —SH, or —S—$C_{1-10}$ alkyl;
R is a straight chain or branched $C_{1-30}$ alkyl; and
R$^1$ is H, $C_{1-10}$ alky, $C_{2-10}$ alkenyl, $C_{2-10}$ alkynyl, aryl, or aralkyl;
provided that R may be unsubstituted or substituted by one or more —OH, $C_{1-10}$ alkoxy, —N(R$^1$)$_2$, —SH, —S—$C_{1-10}$ alkyl, or aryl. Methods for making the compounds of formula may be found in, for example, U.S. Pat. Nos. 4,558,070; 4,595,695; 4,654,370; 4,895,873; 4,913,906; 5,017,613; 5,019,398; 5,049,586; 5,162,573; 5,440,023; 5,856,569; 6,131,106 and 6,610,326.

VPA refers to 2-propylpentanoate, an anticonvulsant drug that is reported to modify excitatory-inhibitory functions by increasing glutamate reuptake and γ-aminobutyric acid (GABA) concentrations (Hassel et al., 2001; Loscher, 1999; Owens and Nemeroff, 2003). Other names and descriptions of VPA are also envisioned herein, such as Depakote, Valrelease, valproate and sodium valproate. In addition to epilepsy, VPA has been prescribed for treatment of bipolar disorder, migraine, and post-traumatic stress disorder.

In addition to the indications above, valproate is reported to be effective in treating age-related cognitive impairment (Koh et al., 36th annual meeting of the Society for Neuroscience, Oct. 15, 2006, No. 273.14, D.3). Chronic subcutaneous administration to memory-impaired aged rats of 100 mg/kg/day sodium valproate treated their age-related cognitive impairment and their performance in a memory test was significantly improved. This dosage results in a blood total valproate level of 10 μg/ml plasma (10 μg/ml total VPA). Treatment with chronic subcutaneous administration of 50 mg/kg/day VPA, however, was not effective.

In certain embodiments, wherein a SV2A inhibitor is administered in combination with VPA or analogs or derivatives or pharmaceutically acceptable salts or solvates thereof, the dosage of both VPA or analogs or derivatives or pharmaceutically acceptable salts or solvates thereof and the SV2A inhibitor are each sub-therapeutic with respect to treating age-related cognitive impairment when administered alone. In certain embodiments, the daily dose of the SV2A inhibitor, when administered in combination with VPA or analogs or derivatives or pharmaceutically acceptable salts or solvates thereof, is 0.01 to 1 mg/kg. In certain embodiments, the daily dose of the SV2A inhibitor, when administered in combination with VPA or analogs or derivatives or pharmaceutically acceptable salts or solvates thereof, is 0.001 to 1.0 mg/kg. In certain embodiments, the dose of valproate when administered in combination with an SV2A inhibitor is 0.5 to 5 µg/ml total WA. The doses useful for analogs or derivatives of VPA, or pharmaceutically acceptable salts or solvates thereof are readily determined by those skilled in the art, using the methods of this invention.

It will be understood by one of ordinary skill in the art that the compositions and methods described herein may be adapted and modified as is appropriate for the application being addressed and that the compositions and methods described herein may be employed in other suitable applications, and that such other additions and modifications will not depart from the scope hereof.

This invention will be better understood from the Experimental Details which follow. However, one skilled in the art will readily appreciate that the specific methods and results discussed are merely illustrative of the invention as described more fully in the embodiments which follow thereafter.

EXAMPLES

Introduction and Models of Age-Related Cognitive Impairment

A variety of conditions characterized by cognitive impairment (e.g., Age-Associated Memory Impairment [AAMI], Mild Cognitive Impairment [MCI] and Age-related Cognitive Decline [ARCD]) are believed to be related to aging. Animal models serve as an important resource for developing and evaluating treatments for such age-related cognitive impairments. Features that characterize age-related cognitive impairment in animal models typically extend to age-related cognitive impairment in humans. Efficacy in such animal models is, thus, predictive of efficacy in humans.

Of available models, a Long-Evans rat model of cognitive impairment is particularly well suited for distinguishing the difference between cognitive impairment related to illness and that related to aging. Indeed, extensive behavioral characterization has identified a naturally occurring form of cognitive impairment in an outbred strain of aged Long-Evans rats (Charles River Laboratories; Gallagher et al., *Behav. Neurosci.* 107:618-626, (1993)). In a behavioral assessment with the Morris Water Maze (MWM), rats learn and remember the location of an escape platform guided by a configuration of spatial cues surrounding the maze. The cognitive basis of performance is tested in probe trials using measures of the animal's spatial bias in searching for the location of the escape platform. Aged rats in the study population have no difficulty swimming to a visible platform, but an age-dependent impairment is detected when the platform is camouflaged, requiring the use of spatial information. Performance for individual aged rats in the outbred Long-Evans strain varies greatly. For example, a proportion of those rats perform on a par with young adults. However, approximately 40-50% fall outside the range of young performance. This variability among aged rats reflects reliable individual differences. Thus, within the aged population some animals are cognitively impaired and designated aged-impaired (AI) and other animals are not impaired and are designated aged-unimpaired (AU). See, e.g., Colombo et al., *Proc. Natl. Acad. Sci.* 94: 14195-14199, (1997); Gallagher and Burwell, *Neurobiol. Aging* 10: 691-708, (1989); Rapp and Gallagher, *Proc. Natl. Acad. Sci.* 93: 9926-9930, (1996); Nicolle et al., *Neuroscience* 74: 741-756, (1996); and Nicolle et al., *J. Neurosci.* 19: 9604-9610, (1999).

We have used this rat model to identify genes implicated in age-related changes in cognitive function.

Example 1

Increased Gene Expression of SV2a in Aged-Impaired Rats

Behavioral Characterization of Young, Aged-Impaired and Aged-Unimpaired Rats in Morris Water Maze (MWM)

Behavioral tests were performed on young (4 months old) and aged (24 months old) pathogen-free male Long-Evans rats.

The MWM apparatus consists of a large, circular pool (diameter 1.83 m; height, 0.58 m) filled with water (27° C.) that is made opaque through the addition of non-toxic pigment or some other substance. In the typical "hidden platform" version of the test, rats are trained to find a camouflaged white escape platform (height, 34.5 cm) that is positioned in the center of one quadrant of the maze about 1.0 cm below the water surface. This platform can be retracted to the bottom of the tank or raised to its normal position from outside the maze during behavioral testing. The location of the platform remains constant from trial to trial. Because there are no local cues that mark the position of the platform, the rat's ability to locate it efficiently from any starting position at the perimeter of the pool depends on using information surrounding the maze. The maze is surrounded by black curtains to which white patterns are affixed to provide a configuration of spatial cues. A second platform (height 37.5 cm), with its surface painted black is elevated 2 cm above the water surface during cue training to control for factors unrelated to cognition. The behavior of a rat in the pool is recorded by a camera that is suspended 2.5 m above the center of the pool. The camera is connected to a video tracking system (HVS Image Advanced Tracker VP200) and a PC computer running HVS software developed by Richard Baker of HVS Image, Hampton, UK.

The MWM protocol is optimized for sensitivity to the effects of aging on cognition and for measures of reliable individual differences within the aged population of out-bred Long-Evans rats (Gallagher et al. *Behav. Neurosci.* 107:618-626, (1993)). Rats receive three trials per day for 8 consecutive days, using a 60 sec inter-trial interval. On each training trial, the rat is released into the maze from one of four equally spaced starting positions around the perimeter of the pool. The starting position varies from trial to trial, thus preventing the use of a response strategy (e.g., always turning left from the start location to locate the escape platform). If a rat does not locate the escape platform within 90 sec on any trial, the experimenter guides the rat to the platform, where it remains for 30 sec. Every sixth trial consists of a probe trial to assess the development of spatial bias in the maze. During these trials, the rat swims with the platform retracted to the bottom of the pool for 30 sec, at which time the platform is raised to its normal position for completion of the escape trial. At the completion of the protocol using the hidden platform, rats are assessed for cue learning using the visible platform. The location of this platform varies from trial to trial in a single session of 6 training trials.

The proximity of the animal's position with respect to the goal is used to analyze the training trial and probe trial performance. The proximity measure is obtained by sampling the position of the animal in the maze (10 times/sec) to provide a record of distance from the escape platform in 1 sec averages. For both probe trials and training trials, a correction procedure is implemented so that trial performance is relatively unbiased by differences in distance to the goal from the various start locations at the perimeter of the pool. In making this correction, the average swimming speed is calculated for each trial (path length/latency). Then, the amount of time required to swim to the goal at that speed from the start location used for the trial is removed from the record prior to computing trial performance, i.e., cumulative distance on training trials and average distance from the goal on probe trials. Thus, scores obtained using the proximity measure are designed to reflect search error, representing deviations from an optimal search, i.e. direct path to the goal and search in the immediate vicinity of that location during probe trials.

Computer records of video-tracking are compiled to provide data on each rat's performance in the maze. Measures on training trials and probe trials are analyzed by Analysis of Variance (ANOVA).

In one set of trials, the performance during training with the hidden, camouflaged platform differs between the groups of young and aged rats [$F(1, 23)=12.69$, $p<0.002$]. In this set of trials, no difference between the groups is observed for the cue training trials with a visible platform. In this set of trials, latencies to escape during cue training averaged 9.36 seconds for young and 10.60 seconds for the aged rats.

An average proximity measure on interpolated probe trials is used to calculate a spatial learning index for each individual subject as described in detail in Gallagher et al., *Behav. Neurosci.* 107:618-26, (1993). When a rat rapidly learns to search for the platform close to its position, its spatial learning index is low. Overall, in one set of trials aged rats differed from young rats [$F(1, 23)=15.18$, $p<0.001$]. Aged rats are classified as either unimpaired or impaired relative to the learning index profile of the young study population. Aged rats that fall within the normative range of young rats (index scores <241) are designated aged-unimpaired (AU). The remaining aged subjects that have index scores outside the range of young performance are designated aged-impaired (AI).

Preparation of RNA from Behaviorally Characterized Rats

Twenty-four outbred Long-Evans rats, behaviorally characterized as is described above, are killed by live decapitation to obtain fresh brain tissue. The brain is removed, and the dentate gyrus hippocampal region is microdissected from 500 micron sections taken through the transverse axis of the entire hippocampal formation (both left and right hippocampi) of 24 characterized rats. There are 8 animals in each group (AI, AU, and Y).

Total RNA is isolated using Trizol reagent (Invitrogen, Carlsbad, Calif.) according to the standard protocol (homogenization in Trizol reagent followed by chloroform extraction and isopropanol precipitation). Total RNA is further purified using the RNeasy mini kit (Qiagen, Valencia, Calif.). cRNA probes are then generated from the RNA samples at the Johns Hopkins Microarray Core Facility, generally according to Affymetrix specifications.

Briefly, 5 µg of total RNA is used to synthesize first strand cDNA using oligonucleotide probes with 24 oligo-dT plus T7 promoter as primer (Proligo LLC, Boulder, Calif.), and the SuperScript Choice System (Invitrogen). Following the double stranded cDNA synthesis, the product is purified by phenol-chloroform extraction, and biotinilated anti-sense cRNA is generated through in vitro transcription using the BioArray RNA High Yield Transcript Labeling kit (ENZO Life Sciences Inc., Farmingdale, N.Y.). 15 µg of the biotinilated cRNA is fragmented at 94° C. for 35 min (100 mM Trix-acetate, pH 8.2, 500 mM KOAC, 150 mM MgOAC). 10 µg of total fragmented cRNA is hybridized to the RAT genome 230-2 Affymetrix GeneChip array for 16 hours at 45° C. with constant rotation (60 rpm).

Affymetrix Fluidics Station 450 is then used to wash and stain the chips, removing the non-hybridized target and incubating with a streptavidin-phycoerythrin conjugate to stain the biotinilated cRNA. The staining is then amplified using goat immunoglobulin-G (IgG) as blocking reagent and biotinilated anti-streptavidin antibody (goat), followed by a second staining step with a streptavidin-phycoerythrin conjugate.

For quality control of the total RNA from the samples, the Agilent Bioanalyzer, Lab on a Chip technology, is used to confirm that all the samples had optimal rRNA ratios (1:2, for 18S and 28S, respectively) and clean run patterns.

For quality control of the hybridization, chip image, and comparison between chips, the following parameters are considered: Scaling factor: related to the overall intensity of the chip, to confirm the similar signal intensity and staining through out the samples; Background: estimation of unspecific or cross-hybridization; Percentage of present calls: percentage of transcripts that are considered significantly hybridized to the chip (present) by the algorithm; Glyseraldehyde-3-phosphate dehydrogenase (GAPDH) (3'/5'): representation of the RNA integrity by measuring the ratio of 3' to 5' regions for the housekeeping gene GAPDH, its presence in the chip and a ratio close to 1 advocates for a good integrity of the target (sample); Spikes (BioB/BioC) to confirm the detection level and sensitivity after hybridization.

Data Analysis of Microarray

Fluorescence is detected using the Affymetrix G3000 GeneArray Scanner and image analysis of each GeneChip is done through the GeneChip Operating System 1.1.1 (GCOS) software from Affymetrix, using the standard default settings. All of the GeneChip arrays use short oligonucleotides for genes in an RNA sample.

For comparison between different chips, global scaling is used, scaling all probe sets to target intensity (TGT) of 150. Total number of present calls and scaling factors are similar across all chips. Further analysis for presence/absence and statistical difference is performed on a region by region basis in the following manner. Probe sets are determined to be present in a region if it had a present call in four of eight animals in a single group.

Probe sets are annotated using the Affymetrix annotation of Jun. 20, 2005, and all probe sets representing a specific gene are identified.

An ANOVA is conducted on the probe set signal values for all present probe sets by combining two groups of animals and comparing them to the third group. An "AI ANOVA" is performed, where AU group are combined with Young group and compared to AI group.

Pearsons's correlations comparing probe set signal values to learning indices were calculated for the aged animals (excluding young) across all present probe sets. As shown in FIG. 1, expression of genes encoding SV2A was significantly increased in aged-impaired (AI) individuals relative to young individuals (Y) and aged-unimpaired individuals (AU) in a set of experiments performed as above. These results show that increased SV2A expression was correlated to the development of age-related cognitive impairment.

Example 2

Effect of Levetiracetam in Aged-Impaired Rats

Morris Water Maze Results

Six Age-Impaired (AI) Long-Evans rats (as characterized above) were tested for their memory of new spatial information in the MWM, under different drug/control treatment conditions (vehicle control and two different dosage levels of levetiracetam). The MWM protocol was substantially the same as the one described in Example 1. Specifically for this study, a retention trial was performed after the training trials, as described below.

AI rats were given six training trials per training day with a 60-sec inter-trial interval between each training trial for two consecutive days. On each training trial, the rat was released in the maze from one of four equally spaced starting positions around the perimeter of the pool. If the rat did not locate the escape platform within 90 sec on any trial, the experimenter guided the rat to the platform, where it remained for 30 sec. 30 minutes to 1 hour prior to all the training trials on each training day, AI rats were pretreated with one of three drug conditions: 1) vehicle control (0.9% saline solution); 2) levetiracetam (5 m/kg/day); and 3) levetiracetam (10 mg/kg/day); through intraperitoneal (i.p.) injection. The same six AI rats were used for the entire trials so that each treatment condition was tested on all six rats. Therefore, to counterbalance any potential bias, both the location of the escape platform and the spatial cues surrounding the water maze were different in the three treatment conditions. Therefore, using one set of locations and spatial cues, two rats were treated with saline control solution, two with levetiracetam (5 m/kg/day) and two with levetiracetam (10 mg/kg/day). Using the second set of locations and spatial cues, the two rats treated with saline control solution in the first test were treated with either levetiracetam (5 m/kg/day) or levetiracetam (10 mg/kg/day), and the two rats previously treated with levetiracetam (5 m/kg/day) were treated with either saline control solution or levetiracetam (10 mg/kg/day), and the two rats previously treated with levetiracetam (10 mg/kg/day) were treated with either saline control solution or levetiracetam (5 m/kg/day). Using the last set of locations and spatial cues, the rat groupings were again switched so that each group was treated with a different condition than they had been treated previously.

After the second training day and completion of the twelve training trials (over the two days), the rat was returned to its home cage and placed in the animal housing room. After a delay of 24 hours from the last training trial, the rat was given one testing trial (the "retention trial"), which was the same MWM task as the training trials, but with the escape platform removed.

Figure 2:
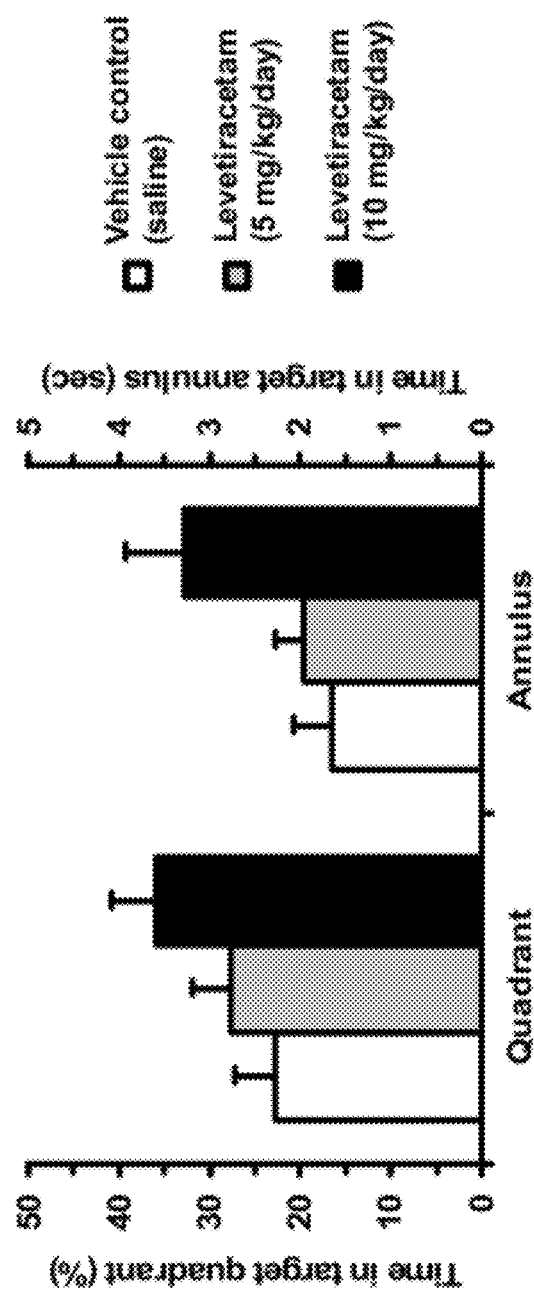
FIG. 2 depicts the effects of administering levetiracetam on the spatial memory retention of six aged-impaired rats (AI) in a Morris Water Maze (MWM) test. Three treatment conditions were employed: vehicle control, levetiracetam (5 mg/kg/day) and levetiracetam (10 mg/kg/day). The AI rats were trained for two consecutive days, with a one-time treatment prior to the training trials per day. 24 hours later, the AI rats were tested. The time the AI rats, 24 hours after treatment with the different conditions and two days of training, spent swimming in the target quadrant or the target annulus in a memory retention trial is used as a measure of spatial memory retention. The target quadrant refers to the quadrant of the maze (which is a circular pool) where the escape platform is placed during the training trials. The target annulus refers to the exact location of the escape platform during the training trials.

For the retention trial, the MWM circular pool was divided into 4 quadrants. The particular quadrant where the escape platform was placed in the training trials is referred as "target quadrant". The particular region where the platform was located in the training trials is referred as "target annulus". In the retention trial, the time the AI rats spent swimming in the target quadrant is measured and further plotted as a percentage of total swimming time. FIG. 2 displays the results of one such set of retention trials. The time the AI rats spend in the target annulus is also measured. FIG. 2 displays the results of one such set of retention trials. Time data are collected for all three drug treatment conditions.

In the retention trial, whose results are depicted in FIG. 2, the time the AI rats spent in the target quadrant was approximately 25%, which is a performance equivalent to them having no memory of the platfrom location. This performance did not significantly improve in the group treated with levetiractam at 5 mg/kg/day. However, the group treated with levetiractam at 10 mg/kg/day demonstrated significantly improved memory as compared to vehicle-treated controls, as indicated by a significant increase in the time spent in the target quadrant to approximately 35% of total swimming time (see FIG. 2). That level of performance is equivalent to young and age-unimpaired rats, indicating that treatment with 10 mg/kg/day levetiractam resulted in a significant recovery of the AI rats' ability to navigate this MWM. The effectivness of the 10 mg/kg/day levetiracetam treatment was also seen in the time spent in the target annulus (see FIG. 2).

Radial Arm Maze Results

The effects of levetiracetam on the spatial memory retention of aged-impaired (AI) rats were assessed in a Radial Arm Maze (RAM) behavioral task using vehicle control and five different dosage levels of levetiracetam (1.25 mg/kg/day, 2.5 mg/kg/day, 5 mg/kg/day, 10 mg/kg/day and 20 mg/kg/day). RAM behavioral tasks were preformed on ten AI rats. All six treatment conditions were tested on all ten rats, as described above for the MWM test.

The RAM apparatus used consisted of eight equidistantly-spaced arms. An elevated maze arm (7 cm width×75 cm length) projected from each facet of an octagonal center platform (30 cm diameter, 51.5 cm height). Clear side walls on the arms were 10 cm high and were angled at 65° to form a trough. A food well (4 cm diameter, 2 cm deep) was located at the distal end of each arm. Froot Loops™ (Kellogg Company) were used as rewards. Blocks constructed of Plexiglas™ (30 cm height×12 cm width) could be positioned to prevent entry to any arm. Numerous extra maze cues surrounding the apparatus were also provided.

The AI rats were initially subjected to a pre-training test (Chappell et al. Neuropharmacology 37: 481-487, 1998). The pre-training test consisted of a habituation phase (4 days), a training phase on the standard win-shift task (18 days) and another training phase (14 days) in which a brief delay was imposed between presentation of a subset of arms designated by the experimenter (e.g., 5 arms available and 3 arms blocked) and completion of the eight-arm win-shift task (i.e., with all eight arms available).

In the habituation phase, rats were familiarized to the maze for an 8-minute session on four consecutive days. In each of these sessions food rewards were scattered on the RAM, initially on the center platform and arms and then progressively confined to the arms. After this habituation phase, a standard training protocol was used, in which a food pellet was located at the end of each arm. Rats received one trial each day for 18 days. Each daily trial terminated when all eight food pellets had been obtained or when either 16 choices were made or 15 minutes had elapsed. After completion of this training phase, a second training phase was carried out in which the memory demand was increased by imposing a brief delay during the trial. At the beginning of each trial, three arms of the eight-arm maze were blocked. Rats were allowed to obtain food on the five arms to which access was permitted during this initial 'information phase' of the trial. Rats were then removed from the maze for 60 seconds, during which time the barriers on the maze were removed, thus allowing access to all eight arms. Rats were then placed back onto the center platform and allowed to obtain the remaining food rewards during this 'retention test' phase of the trial. The identity and configuration of the blocked arms varied across trials.

The number of "errors" the AI rats made during the retention test phase was tracked. An error occurred in the trial if the rats entered an arm from which food had already been retrieved in the pre-delay component of the trial, or if it re-visited an arm in the post-delay session that had already been visited.

After completion of the pre-training test, rats were subjected to trials with more extended delay intervals, i.e., a one-hour delay, between the information phase (presentation with some blocked arms) and the retention test (presentation of all arms). During the delay interval, rats remained off to the side of the maze in the testing room, on carts in their individual home cages. AI rats were pretreated 30-40 minutes before daily trials with a one-time shot of the following six conditions: 1) vehicle control (0.9% saline solution); 2) levetiracetam (1.25 mg/kg/day); 3) levetiracetam (2.5 mg/kg/day); 4) levetiracetam (5 mg/kg/day); 5) levetiracetam (10 mg/kg/day); 6) levetiracetam (20 mg/kg/day); through intraperitoneal (i.p.) injection. Injections were given every other day with intervening washout days. Each AI rat was treated with all six conditions within 23 days of testing. To counterbalance any potential bias, drug effect was assessed using ascending-descending dose series, i.e., the dose series was given first in an ascending order and then repeated in a descending order. Therefore, each dose had two determinations.

Figure 3:
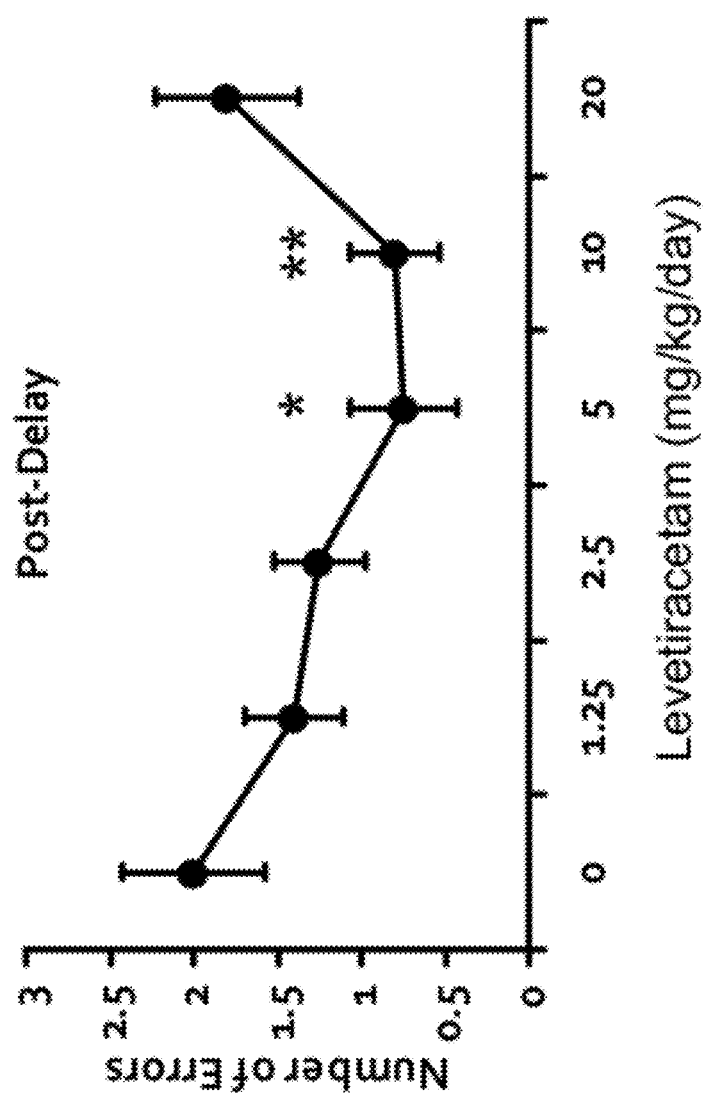
FIG. 3 depicts the effects of administering levetiracetam on the spatial memory retention of ten aged-impaired rats (AI) in an eight-arm Radial Arm Maze (RAM) test. Six treatment conditions were employed: vehicle control, levetiracetam (1.25 mg/kg/day), levetiracetam (2.5 mg/kg/day), levetiracetam (5 mg/kg/day), levetiracetam (10 mg/kg/day) and levetiracetam (20 mg/kg/day). In the RAM task used, there was a one-hour delay between presentation of a subset of arms (5 arms available and 3 arms blocked) and completion of the eight-arm win-shift task (eight arms available). Rats were pre-treated 30-40 minutes before daily trials with a one-time drug/control treatment. The number of errors made by the rats after the delay was used as a measure of spatial memory retention. Errors were defined as instances when rats entered an arm from which food had already been retrieved in the pre-delay component of the trial or when rats re-visited an arm in the post-delay session that had already been visited. Paired t-tests were used to compare the number of errors between different doses of levetiracetam and vehicle control.

Parametric statistics (paired t-tests) was used to compare the retention test performance of the AI rats in the one-hour delay version of the RAM task in the context of different doses of levetiracetam and vehicle control (see FIG. 3). The average numbers of errors that occurred in the trials were also significantly fewer with levetiracetam treatment of 5 mg/kg/day (average no. of errors±standard error of the mean (SEM)=0.75±0.32) and 10 mg/kg/day (average no. of errors±SEM=0.80±0.27) than using vehicle control (average no. of errors±SEM=2.00±0.42). Relative to vehicle control treatment, levetiracetam significantly improved memory performance at 5 mg/kg/day ($t(9)=2.18$, $p=0.057$) and 10 mg/kg/day ($t(9)=2.37$, $p=0.042$).

To calculate the human equivalent dose (HED) for levetiracetam dosage for treatment of age-dependent cognitive impairment in humans, we employed the formula HED (mg/kg)=rat dose (mg/kg)×0.16 (see Estimating the Safe Starting Dose in Clinical Trials for Therapeutics in Adult Healthy Volunteers, December 2002, Center for Biologics Evaluation and Research). Therefore, the dosage of 5 mg/kg/day in rats is equivalent to 0.8 mg/kg/day in humans and the dosage of 10 mg/kg/day in rats is equivalent to 1.6 mg/kg/day in humans.

What is claimed is:

1. A method for treating age-related cognitive impairment in a human subject in need thereof, the method comprising the step of administering to said human subject levetiracetam or a pharmaceutically acceptable salt thereof at a daily dose of 125-250 mg.

2. The method of claim 1, wherein the age-related cognitive impairment is selected from the group consisting of mild cognitive impairment, age-associated memory impairment, and age-related cognitive decline.

3. The method of claim 1, wherein the levetiracetam or the pharmaceutically acceptable salt thereof is administered once or twice daily.

4. The method of claim 1, wherein the effect of the treatment is measured by the Clinical Dementia Rating Scale.

5. The method of claim 1, wherein the daily dose is 125 mg.

6. The method of claim 1, wherein the daily dose is 250 mg.

7. A method for delaying or slowing the progression of cognitive impairment in a human subject suffering from age-related cognitive impairment, the method comprising the step of administering to said human subject levetiracetam or a pharmaceutically acceptable salt thereof at a daily dose of 125-250 mg.

8. The method of claim 7, wherein the age-related cognitive impairment is selected from the group consisting of mild cognitive impairment, age-associated memory impairment, and age-related cognitive decline.

9. The method of claim 7, wherein the progression of cognitive impairment is measured by the Clinical Dementia Rating Scale.

10. The method of claim 7, wherein the levetiracetam or the pharmaceutically acceptable salt thereof is administered once or twice daily.

11. The method of claim 7, wherein the daily dose is 125 mg.

12. The method of claim 7, wherein the daily dose is 250 mg.

13. A method for reducing the rate of decline of cognitive function in a human subject suffering from age-related cognitive impairment, the method comprising the step of administering to said human subject levetiracetam or a pharmaceutically acceptable salt thereof at a daily dose of 125-250 mg.

14. The method of claim 13, wherein the age-related cognitive impairment is selected from the group consisting of mild cognitive impairment, age-associated memory impairment, and age-related cognitive decline.

15. The method of claim 13, wherein the levetiracetam or the pharmaceutically acceptable salt thereof is administered once or twice daily.

16. The method of claim 13, wherein the rate of decline of cognitive function is measured by the Clinical Dementia Rating Scale.

17. The method of claim 13, wherein the daily dose is 125 mg.

18. The method of claim 13, wherein the daily dose is 250 mg.

* * * * *

UNITED STATES PATENT AND TRADEMARK OFFICE
CERTIFICATE OF CORRECTION

| | | |
|---|---|---|
| PATENT NO. | : 8,604,075 B2 | Page 1 of 1 |
| APPLICATION NO. | : 13/287531 | |
| DATED | : December 10, 2013 | |
| INVENTOR(S) | : Michela Gallagher, Rebecca Haberman and Ming Teng Koh | |

It is certified that error appears in the above-identified patent and that said Letters Patent is hereby corrected as shown below:

In the Specification

Column 1, Line 1, 3-6, please replace the second paragraph as follows:

STATEMENT OF GOVERNMENTAL INTEREST
This invention was made with government support under grant number AG009973, awarded by the National Institutes of Health. The government has certain rights in the invention.

Signed and Sealed this
Tenth Day of April, 2018

Andrei Iancu
*Director of the United States Patent and Trademark Office*